United States Patent [19]

Lo et al.

[11] Patent Number: 5,192,785
[45] Date of Patent: Mar. 9, 1993

[54] SULFAMATES AS ANTIGLAUCOMA AGENTS

[75] Inventors: Young S. Lo, Hockessin, Del.; Joseph C. Nolan, Midlothian; Dwight A. Shamblee, Richmond, both of Va.

[73] Assignee: A. H. Robins Company, Incorporated, Richmond, Va.

[21] Appl. No.: 712,855

[22] Filed: Jun. 10, 1991

Related U.S. Application Data

[63] Continuation-in-part of Ser. No. 406,736, Sep. 3, 1989, abandoned.

[51] Int. Cl.[5] .................. A61K 31/415; A61K 31/255; A61K 31/325
[52] U.S. Cl. ..................... 514/399; 514/517; 558/48
[58] Field of Search ................... 514/399, 517

[56] References Cited

U.S. PATENT DOCUMENTS

| | | | |
|---|---|---|---|
| 4,513,006 | 4/1985 | Maryanoff | 514/23 |
| 4,582,916 | 4/1986 | Maryanoff | 549/387 |
| 4,591,601 | 5/1986 | Maryanoff | 514/462 |
| 4,619,939 | 10/1986 | Maren | 514/363 |
| 4,792,569 | 12/1988 | Maryanoff | 514/517 |

OTHER PUBLICATIONS

Weiss Liebigs Ann Chem 729 40 (1969).
Maryanoff, et al. J. Med. Chem. 1987, 30, 880–887.

Primary Examiner—Robert Gerstl
Attorney, Agent, or Firm—R. F. Boswell, Jr.

[57] ABSTRACT

Sulfamate esters of the formula $$(HO)_p-A-[OSO_2NR^1R^2]_z$$

where A is aryloxyalkyl, p is the number of unreacted hydroxy groups present on the alkyl moiety and may be zero, z is the number of $-OS(O)_2NR^1R^2$ groups attached to carbons of the alkyl moiety and is always at least one; $R^1$ and $R^2$ are selected from hydrogen, lower-alkyl, carboxy, and the like are useful in treating glaucoma.

20 Claims, No Drawings

SULFAMATES AS ANTIGLAUCOMA AGENTS

This application is a continuation-in-part of pending application Ser. No. 07/406,736 filed Sep. 3, 1989, now abandoned.

BACKGROUND OF THE INVENTION

1. Field of Invention

This invention relates to a pharmaceutical method and composition for reducing intraocular pressure in living animals usually resulting from glaucoma using a wide range of organic sulfamates as active agents.

Glaucoma, a condition, wherein the intraocular pressure is elevated, may cause damage to the optic nerve and eventual blindness if not corrected.

The compounds generally may be administered orally, parenterally or topically to the eye as suspensions or when sufficiently soluble as solutions.

2. Information Disclosure Statement

Carbonic anhydrase enzyme which plays a part in reversibly catalyzing hydration of carbon dioxide in animals is at least in part responsible for aqueous humor formation in the eye and it is known that inhibitors of this enzyme can be used to relieve excessive eye pressure associated with glaucoma [Havener, Ocular Pharmacology, 4th Ed. (1978, C. V. Moseby); Maren, Investigative Ophthalmology, Vol. 13, pp. 479–484 (1974); Becker, Am. J. of Ophthalmology, Vol. 39, p. 177 (1955)].

U.S. Pat. No. 4,619,939 (Maren, T. H.) discloses the optical application to the eye of certain sulfonamides having carbonic anhydrase inhibition, water solubility of about 0.1% at pH 8.2 and first order rate penetration through a living rabbit cornea and other properties for the purpose of reducing aqueous humor formation and in intraocular pressure.

In contrast to the compounds of the Maren patent, the compounds of the present invention are sulfamates which differ structurally by incorporation of an oxygen atom which is interposed between the sulfonamide radical and the molecular moiety which carries the sulfamate group. More than one sulfamate group may be present. The use of the compounds of the present invention is not limited to topical application and therefore useful compounds are not confined to parameters suitable therefor. Many of the sulfamate compounds useful in the present invention are potent carbonic anhydrase inhibitors.

U.S. Pat. Nos. 4,513,006 and 4,582,916 disclose alicyclic compounds having a single sulfamate radical of the formula:

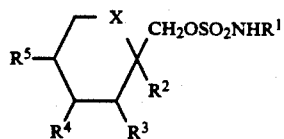

having antiglaucoma activity wherein X is O or $CH_2$; $R^1$ is hydrogen or loweralkyl ; $R^2$, $R^3$, $R^4$ and $R^5$ are hydrogen or loweralkyl and when X is $CH_2$, $R^4$ and $R^5$ may be alkene groups joined to form a benzene ring and when X is oxygen, $R^2$ and $R^3$ and $R^4$ and $R^5$ together may form a methylenedioxy groups such as a sugar skeleton.

U.S. Pat. No. 4,591,601 disclosed dioxolane methane sulfamates to be useful as antiglaucoma agents.

U.S. Pat. No. 4,792,569 disclosed phenylethyl sulfamates to be useful as antiglaucoma agents having the formula:

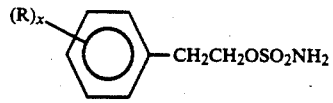

wherein R is alkyl, halo, alkoxy, trifluoromethyl or nitro and x is 0–3.

The compounds useful in the present invention are the subject of a commonly owned invention in application Ser. No. 365,212 filed on Jun. 12, 1989 wherein use in treating arthritis and osteoporosis is disclosed.

SUMMARY OF THE INVENTION

This invention provides a method, novel compounds, and compositions for educing intraocular pressure and reducing aqueous humor formation utilizing as active agents compounds having the formula:

$$(HO)_p\text{-}A\text{-}[OS(O)_2NR^1R^2]_z \qquad \text{Formula I}$$

wherein A is substituted on one or more carbon atoms by an aminosulfonyloxy radical, i.e., a radical having the formula $-OS(O)_2NR^1R^2$, said A being selected from the group consisting of:

aryl,
alkyl,
cycloalkyl,
aryl-alkyl,
haloalkyl,
cycloalkyl-alkyl,
aryloxy-alkyl,
alkyloxy-alkyl,
(aryl)(lowerealkyl)aminoalkyl,
aryl-thio alkyl,
aryl-sulfinyl-alkyl,
aryl-sulfonyl-alkyl,
arylaminocarbonylalkyl,
alkylaminocarbonylalkyl,
aryloxycarbonylalkyl,
alkyloxycarbonylalkyl,
2-pyrrolidinone-1-alkyl,
alkylcarbonylalkyl,
arylcarbonylalkyl,
arylalkanoic acid,
arylhalogen substituted alkyl
arylalkyloxyalkyl

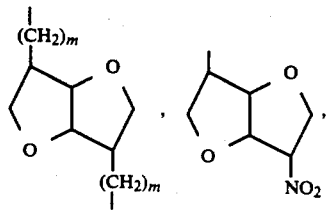

-continued

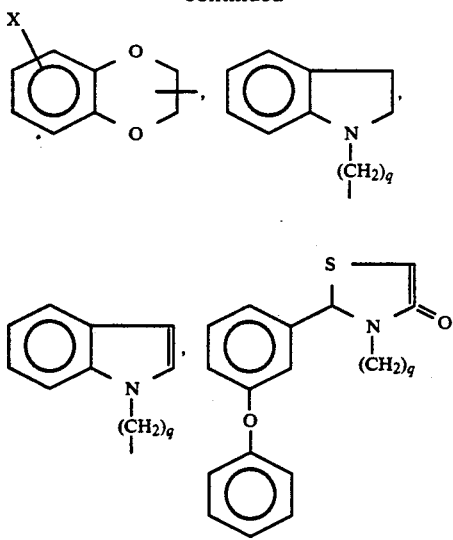

Aryl or aryl moieties are selected from:

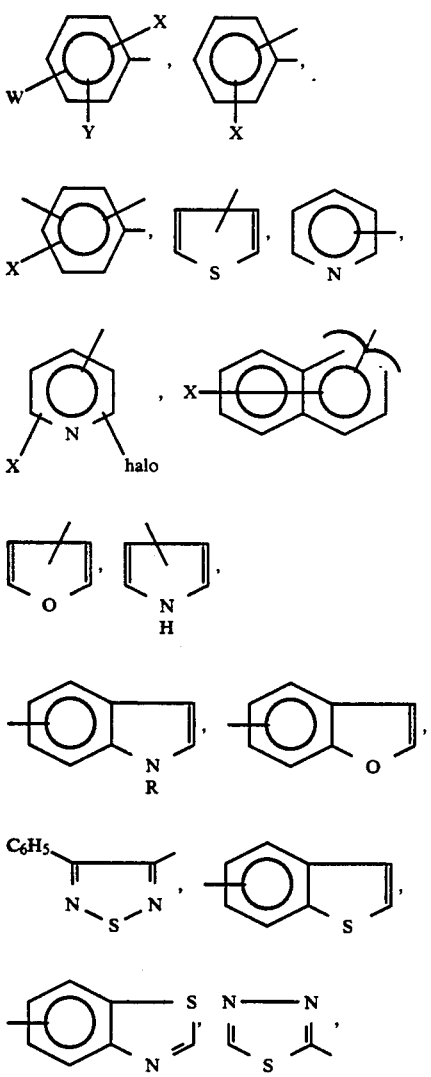

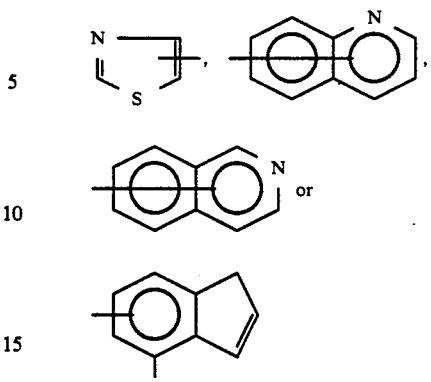

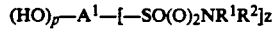

wherein
X is selected from hydrogen, halo, CF₃, nitro, —SO₂NR¹R², loweralkoxy, hydroxy, amino, methylcarbonylamino, loweralkyl, methyloxycarbonyl, 1H-imidazol-1-yl, 3-thiazole, 1-pyrrole, phenyl, 1H-triazol-1-yl, diloweralkylamino, loweralkylamino, cyano, 2-loweralkyl-1H-imidazol-1-yl, 4-loweralkyl-1H-imidazol-1-yl, 4-phenyl-1H-imidazol-1-yl, —COOH, —COOM wherein M is a pharmaceutically acceptable metal cation, aryloxy or aroyl;

Y is selected from: hydrogen, halo, loweralkoxy, hydroxy or loweralkyl;

W is selected from hydrogen, loweralkoxy or loweralkyl;

p=number of unreacted hydroxyl groups, including zero;

z=number of —OS(O)₂NR¹R² groups and is always at least one;

m=0-4;

p+z=1-8;

q=1-10

R=H, loweralkyl;

R¹=H, loweralkyl;

R²=H, loweralkyl, —CO₂R¹, or —CO₂⁻M+ wherein M is defined above and the pharmaceutically acceptable salts thereof, when they can be formed and the optical isomers thereof, when they can be formed; with the proviso that when A is cycloalkyl-alkyl, phenylalkyl or phenyl alkyl wherein phenyl is substituted by loweralkyl, loweralkoxy, trifluoromethyl, halo, or nitro, z is always more than one.

The compounds of Formula I which are novel are represented by Formula Ia (HO)$_p$—A¹—[—SO(O)₂NR¹R²]$_z$    Formula Ia wherein A¹ is substituted on one or more carbon atoms by an aminosulfonyloxy radical, said A¹ being selected from the group consisting of:
aryloxyalkyl,
alkyl,
wherein at least one of the aminosulfonyloxy radicals is on a tertiary carbon atom,
aryloxycarbonylalkyl,
alkyloxycarbonylalkyl,
alkylcarbonylalkyl,
arylcarbonylalkyl,
4-phenyl-thiadiazole-3-yl,
2-pyrrolidone-1-alkyl, or 2-(3-phenoxyphenyl)-4-thiazolidinone-3-yl and wherein the aryl moieties of aryloxyalkyl, aryloxycarbonyl alkyl, arylcarbonylalkyl are as defined for Aryl under Formula I hereinabove and W, X, Y, $R^1$, $R^2$, p and z are as defined under Formula I hereinabove.

In the further definitions of symbols in the formula hereof and terms where they apply elsewhere throughout the specification and the claims, the term have the following significance.

The terms "alkyl" as used herein unless otherwise specified includes straight and branched chain radicals of up to 12 carbons inclusive and is exemplified by such groups as methyl, ethyl, propyl, isopropyl, butyl, sec. butyl, tert. butyl, amyl, isoamyl, hexyl, heptyl, octyl, nonyl, decyl, lauryl and the like and is intended to include methylene chains and branched methylene chains when appropriate under the definitions in the formulas. Loweralkyl radicals have 1-8 carbon atoms.

The term "tertiary carbon atom" as used herein refers to a carbon atom substituted by three radicals other than a hydrogen atom.

The term "cycloalkyl" as used herein includes cyclic alkyl radicals containing 3-9 carbon atoms inclusive and includes such groups as cyclopropyl, cyclobutyl, cyclopentyl, cyclohexyl, methylcyclohexyl, cycloheptyl and the like.

The terms "halo" or "halogen" when referred to herein include fluorine, chlorine, bromine and iodine unless otherwise stated.

Pharmaceutically acceptable salts of the compounds of the present invention generally form when A is an aryl group having a heterocyclic nitrogen radical or A contains a basic nitrogen component and include salts of either strong or weak acids. Representative of strong acids are hydrochloric, sulfuric, phosphoric and alkyl and aryl sulfonic acids. Representative of weak acids are fumaric, maleic, succinic, oxalic, citric, tartaric, hexamic and the like.

A preferred class of compounds is represented by Formula Ib $(HO)_p$—$A^2$[—$OSO_2NR^1R^2$]$_z$   Formula Ib wherein A2 comprises a group under the previous definition of A which possesses a basic moiety capable of forming a pharmaceutically acceptable acid addition salt or an acidic capable of forming a salt with a pharmaceutically acceptable metal cation or a pharmaceutical acceptable organic or inorganic base and $R^1$ and $R^2$ are H. Compounds of Formula Ib are water soluble and are preferred for topical application, thus avoiding any systemic effects of oral or parenteral administration. All other elements of Formula Ib are as defined under Formula I and Formula Ib is encompassed by Formula I.

Elaborating further on the use of the term "wherein A (or $A^1$) is substituted on one or more carbon atoms by an aminosulfonyloxy radical", the aminosulfonyloxy radical represented by —$OS(O)_2NR^1R^2$ may be located singly or multiply on aryl (or other cyclic) or alkyl moieties at any site on one or more carbon atoms capable of being hydroxylated and for example in the instance of phenyl moiety up to 5 such aminosulfonyloxy radicals may be present, thereby wholly or partially superseding the values given in the definition for X, Y and W. In the instance wherein A or $A^1$ contain moieties of such as both aryl (or other cyclics) and alkyl, the aminosulfonyloxy radicals may be present on either or both moieties.

The term "acrotic solvent" as used herein refers to polar solvents of moderately high dielectric constants, which do not contain acidic hydrogen such as dimethylsulfoxide, N,N'-dimethylformamide, p-dioxane and the like. The term "tertiary amine base" as used herein refers to pyridine, trimethylamine, triethylamine, tri-n-propylamine and the like.

By the term "optical isomers" as used herein is meant isomers of compounds of Formula I or Ia which may exist when chiral centers are present in the compounds of Formula I or Ia. These chiral centers when present must be one the "A" moiety of the Formula I compound or the "$A^1$" moiety of the Formula Ia compound. It should be noted that whenever any chiral centers exist in the compounds of Formula I or Ia there is potential for the separation of optical isomers, otherwise known as enantiomers. Exemplary of the methods utilized for the separation of optical isomers of compounds of Formula I or Formula Ia, is the use of column chromatography wherein the column has an appropriate chiral stationary phase. An additional method which may be employed is the use of optically active acids or bases to resolve the enantiomers in successive recrystallizations of the diastereomeric salts. It is also noted that compounds of Formula I and Ia which have chiral centers may be prepared by chiral synthesis methods, if so desired, when the same are applicable to the preparation of a particular optical isomer of a Formula I or Formula Ia compound.

Compounds of Formula I are prepared by Methods I, II and III following:

METHOD I

The process of Method I is represented by the following general equation:

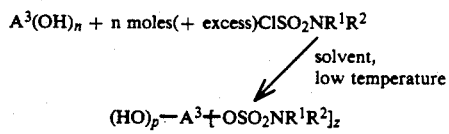

wherein values for $A^3$ include those in the definition for A of Formula I with the proviso that $A^3$ may additionally carry protected carboxy, protected amino or protected hydroxy groups and a further proviso alternative is that aryl may be a group outside the definition of A carrying non-interfering radicals. Compounds prepared under the latter proviso wherein $A^3$ is aryl are useful as reagents in Method II.

$R^1$=hydrogen, loweralkyl or —$C(O)OR^3$,
$R^2$=hydrogen or loweralkyl,
$R^3$=loweralkyl, or phenylloweralkyl,
n=p+z
p=number of unreacted hydroxyl groups including zero,
z=number of sulfamate esterified hydroxy groups.

Protected carboxy groups are represented by benzyloxycarbonyl and trichlorethyloxycarbonyl, Protected amino groups are represented by benzyloxycarbonylamino and trichloroethyloxy carbonyl amino, Protected hydroxy groups are represented by benzyloxycarbonyloxy or trichloroethyloxycarbonyloxy.

Protected carboxy groups, protected amino groups or protected hydroxy groups are deprotected by hydrogenolysis in the instance of benzyloxy carbonyl radicals and deprotected by treating with zinc/acetic acid in the instance of trichloroethyloxycarbonyl radicals.

Generally in Method I, the reaction is carried out in a non-reactive aprotic organic solvent suitably methylene chloride or acetonitrile at temperatures over a range of 0°–100° C. In some instances non-interfering tertiary organic base such as triethylamine, pyridine or diisopropylethylamine are beneficially added to absorb the hydrochloric acid which is liberated. products are isolated by various conventional means as illustrated in the examples.

Method I in conjunction with known protection group chemistry can be used to prepare certain types of Formula I compounds as illustrated in Chart I and Example 50.

tected hydroxy groups are substituted for carboxy, amino or hydroxy, said protected hydroxy being excluded from $(OH)_n$, i.e., when $p=0$, $n=z$.

$R^1$ = hydrogen, loweralkyl or $-C(O)OR^3$,
$R^2$ = hydrogen or loweralkyl,
$R^3$ = loweralkyl, or phenylloweralkyl,
$n = p + z$
$p$ = number of unreacted hydroxyl groups including zero,
$z$ = number of sulfamate esterified hydroxy groups.

Protected carboxy groups are represented by benzyloxycarbonyl and trichlorethyloxycarbonyl.

Protected amino groups are represented by benzylox-

CHART 1

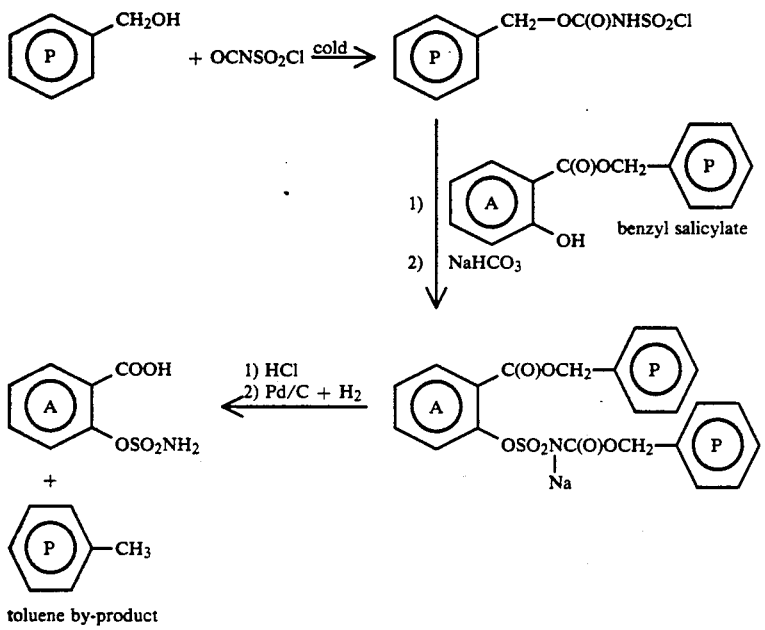

Footnotes Chart I:
P designates radicals involved with protection.
A represents product or core product intermediate.

Carboxy groups in other positions are contemplated. Other groups substitutable for

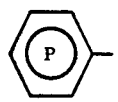

such as pyridinyl, naphthenyl, and biphenyl are also contemplated.

METHOD II—GENERAL

Method II is represented by the following equation:

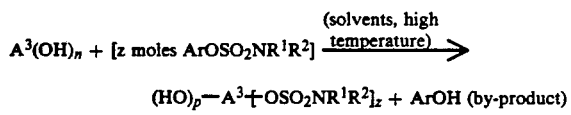

wherein Ar is an aryl group carrying non-interfering radicals and may be an aryl group outside the definition of A or $A^3$;
wherein values for $A^3$ include those in the definition for A of Formula I with the proviso that when $A^3$ is aryl protected carboxy, protected amino or proycarbonylamino and trichloroethyloxy carbonyl amino.

Protected hydroxy groups are represented by benzyloxycarbonyloxy or trichloroethyloxycarbonyloxy.

Protected carboxy groups, protected amino groups or protected hydroxy groups are deprotected by hydrogenolysis in the instance of benzyloxycarbonyl radicals and deprotected by treating with zinc/acetic acid in the instance of trichloroethyloxycarbonyl radicals.

Method II, hereinabove outlined, represents a novel process for synthesizing Formula I compounds and is described more fully as follows: In an organic solvent system consisting of a non-reactive aprotic solvent containing from about 1 to about 20% of a tertiary organic base, and preferably at least 5% of said tertiary organic base, there are reacted at a temperature of from about 50° to 200° C. and preferably at about 90° to 140° C., a reagent sulfamic acid aryl ester and a hydroxy substituted $A^3$ radical wherein $A^3$ is defined as A under Formula I above, except that $A^3$ may not be aryl substituted by unprotected carboxy or unprotected amino, and $A^3$ may additionally be substituted by a protected hydroxy, but wherein said protected hydroxy is excluded from $(OH)_n$ in the equations above. If $A^3$ is substituted by protected amino, protected carboxy or protected hydroxy, then the protected groups are deprotected subsequent to the transfer of the aminosulfonyloxy radical from the sulfamic acid aryl ester reactant, thus giving the desired Formula I compound. In addition to forming the desired Formula I compound in the reaction there is also formed a hydroxy substituted aryl by-product in the reaction. After the desired Formula I compound is formed in the reaction it is extracted from the reaction mixture by partitioning between an organic and aqueous layer and recrystallization by methods commonly known in the art to give a Formula I compound as a free base. A pharmaceutically acceptable salt of the free base may be obtained by reacting with a pharmaceutically acceptable acid in conventional manner.

This novel method for preparing Formula I compounds, labeled as Method II reaction above, may also be referred to as the transfer reaction herein, in as much as the sulfamic acid ester group originally present on the sulfamic acid aryl ester reactant may be considered to be transferred to the hydroxy substituted $A^3$ radical, and the hydroxy substituent on the $A^3$ radical may be considered to be transferred to the aryl radical of the previous sulfamic acid ester group. The aryl group contained on the initial sulfamic acid aryl ester may be selected from aryl as defined under Formula I or from aryl other than that as defined under Formula I, to the extent that the selected aryl substituent is not to be substituted by a radical which would interfere with the transfer of the aminosulfonyloxy radical from the sulfamic acid aryl ester group to the hydroxy substituted $A^3$ reactant. It should be noted that if the aryl substituent of the sulfamic acid aryl ester is the same as the $A^3$ substituent of the hydroxy substituted $A^3$ reactant, then the net effect of the reaction would be zero since the products of the reaction would be equivalent to the reactants, therefore the aryl radical of the sulfamic acid aryl ester should never be identical to the $A^3$ radical of the hydroxy substituted $A^3$ reactant in this method. It should also be understood that this method may be employed to prepare a Formula I compound from another Formula I compound if the Formula I compound utilized in the preparation of the second Formula I compound has an aryl A substituent with no interfering radicals substituted thereon, such as hydroxy, amino, carboxy and the like.

METHOD III—GENERAL

Certain compounds of Formula I and reagents for use in Method II may also be prepared by reaction represented by the following equation:

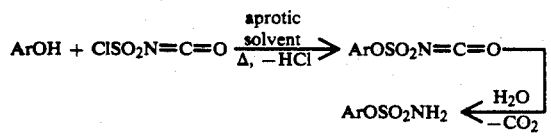

Generally in Method III, the reaction is carried out in a non-reactive aprotic solvent, suitably toluene, chlorobenzene or acetonitrile at temperatures over a range of 80°–150° C.

The preparation of chemical intermediates is illustrated in the following preparations. The examples following the preparations illustrate the synthesis methods for preparing compounds of Formula I. The scope of the present invention is not limited by the descriptive methods and procedures of the preparations and examples, however.

PREPARATION 1

3-(4-Chlorophenoxy)-1,2-propanediol

A mixture of 25.7 g (0.2 mole) of 4-chlorophenol, 18.5 g (0.25 mole) of glycidol and 1 ml of pyridine was stirred and heated at 85°–90° C. overnight. The pot residue was partitioned between ethyl ether and water. The organic layer was washed with water and brine, dried over sodium sulfate, and concentrated to give a gum which crystallized when triturated with petroleum ether (boiling point range, 30°–60° C.). The solid was collected by filtration and recrystallized from isopropyl ether to yield 27.2 g (67%) of off-white solid, mp 73°–75° C. (lit[1] mp 77° C.).

[1] W. Bradley and J. Forrest, Brit 628,497 (1949); Chem Abstr 44, 3023eg (1950).

Analysis: Calculated for $C_9H_{11}ClO_3$: C, 53.35; H, 5.47. Found: C, 53.02; H, 5.56.

PREPARATION 2

3-Phenoxy-1-propanol

To a stirred suspension of 5.7 g (0.15 mole) of lithium aluminum hydride in 350 ml of dry ethyl ether was added dropwise (30 min) a solution of 25.0 g (0.149 mole) of 3-phenoxypropionic acid (99%, Aldrich Chem. Co.) in 250 ml of dry ethyl ether. The reaction mixture was stirred at ambient temperature for 2 hr and treated successively with 6 ml of water, 18 ml of a 15% sodium hydroxide solution, and 10 ml of water. The reaction mixture was filtered through Celite ® and the filtrate was concentrated to a viscous residue. The residue was partitioned between water and ethyl ether (300 ml each). The ethereal layer was washed with two 300 ml portions of water, dried over magnesium sulfate and the solvent was evaporated under reduced pressure to give 16.6 g (73%) of colorless oil.

Analysis: Calculated for $C_9H_{12}O_2$: C, 71.03; H, 7.95. Found: C, 71.09; H, 8.10.

PREPARATION 3

Benzenebutanol

To a stirred suspension of 7.9 g (0.21 mole) of lithium aluminum hydride (Aldrich) in 350 ml of dry ethyl ether was added dropwise a solution of 32.8 g (0.2 mole) of 4-phenylbutyric acid (Aldrich) in 250 ml of dry ethyl ether. The reaction mixture was stirred at ambient temperature for 2 hr, treated successively with 8 ml of water, 25 ml of a 15% sodium hydroxide solution and 8 ml of water, and filtered through Celite ®. The filtrate was washed successively with water (200 ml), twice with 300 ml portions of sodium bicarbonate solution, 300 ml of water and dried over magnesium sulfate. The solvent was evaporated under reduced pressure to give 25.0 g (83%) of colorless oil.

Analysis: Calculated for $C_{10}H_{14}O$: C, 79.96; H, 9.39. Found: C, 79.87; H, 9.32.

PREPARATION 4

2-(3-Methoxyphenoxy)ethanol

This compound was prepared by the procedure of Preparation 2. Thus, 36.5 g (0.2 mole) of 3-methoxyphenoxyacetic acid (Lancaster Synthesis, Inc., Windham, N.H. 03087) and 7.7 g (0.2 mole) of lithium aluminum hydride (Aldrich) in 600 ml of ethyl ether gave 25.7 g (76%) of light-yellow oil.

Analysis: Calculated for $C_9H_{12}O_3$: C, 64.27; H, 7.19. Found: C, 63.93; N, 7.10.

PREPARATION 5

2-(6-Methoxy-2-naphthyl)propanol

This compound was prepared by the procedure used of Preparation 2. Thus, 39.2 g (0.170 mole) of (+)-6-methoxy-α-methyl-2-naphthaleneacetic acid (Naproxen; Sigma) and 6.5 g (0.171 mole) of lithium aluminum hydride (Aldrich) in 600 ml of ethyl ether gave 32.3 g (88% yield) of the title compound, a white solid. A 4.9 g sample of this solid was recrystallized from ethyl ether to give 4.7 g (96% recovery) of white solid, mp 89.5°-91.5° C.

Analysis: Calculated for $C_{14}H_{16}O_2$: C, 77.75; H, 7.46; Found: C, 77.57; H, 7.43.

PREPARATION 6

2-Phenoxy-2,2-dimethyl acetic acid

To a solution of 20.0 g (0.93 mole) of 2-(4-chlorophenoxy)-2-methylpropionic acid (97%, clofibric acid, Aldrich) in 130 ml of methanol and 50 ml of dioxane was added a solution of 13.9 g (0.244 mole) of potassium hydroxide in 75 ml of water. To this solution were added 5 teaspoonfuls of Raney Nickel (Aldrich) and the mixture was hydrogenated at ambient temperature for 3.25 hr ($H_2$-uptake ceased). The reaction mixture was filtered through Celite® and the filtrate was concentrated under reduced pressure to a volume of 150 ml. This solution was extracted with 200 ml of ethyl ether and the ether was discarded. The aqueous layer pH was adjusted to 2 with concentrated hydrochloric acid solution and the resulting white solid was collected by filtration and dried to give 16 g (99%) of white solid. An analytical sample was prepared by recrystallizing from cyclohexane-petroleum ether (b.p. range 30°-60° C.) to give white crystals, mp 98°-100° C.

Analysis: Calculated for $C_{10}H_{12}O_3$: C, 66.65; H, 6.71; Found: C, 66.53; H, 6.72.

PREPARATION 7

2-(Methylphenoxy)ethanol

The title compound was prepared by the procedure of Preparation 2 in 89% yield from 2-(methylphenoxy) acetic acid and lithium aluminum hydride.

PREPARATION 8

4-Phenoxy-1-butanol

The title compound was prepared by the procedure of Preparation 2 in 91% yield from 4-phenoxy-1-butanoic acid and lithium aluminum hydride.

PREPARATION 9

2-(4-Methoxyphenoxy)ethanol

A mixture of 148.8 g (1.20 mole) of p-methoxyphenol, 170 g (2.11 mole) of 2-chloroethanol and 47.2 g (1.18 mole) of sodium hydroxide in 1.5 liter of absolute ethanol was heated at reflux for 22 hr. The solution was filtered, and the solvent was removed from the filtrate in vacuo. The residue was crystallized from methylene chloride-hexane to give 71.4 g (35%) of title compound as a white crystalline solid, mp 69°-71° C.

Analysis: Calculated for $C_9H_{12}O_3$: C, 64.27; H, 7.19. Found: C, 64.18; H, 7.25.

PREPARATION 10

2-Phenoxypropanol

The title compound was prepared by the procedure of Preparation 2 in quantitative yield from 2-phenoxypropionic acid (Aldrich Chem. Co.) and lithium aluminum hydride.

PREPARATION 11

2-(4-Chlorophenoxy)-2-methylpropanol

The title compound was prepared by the procedure of Preparation 2 in quantitative yield from clofibric acid (Aldrich Chem. Co.) and lithium aluminum hydride.

PREPARATION 12

2-(3-Chlorophenoxy)ethanol

A mixture of 51.4 g (0.4 mole) of 3-chlorophenol (Aldrich Chem. Co.), 34.7 g (0.43 mole) of 2-chloroethanol (Aldrich) and 16.1 g (0.4 mole) of sodium hydroxide pellets in 500 ml of 95% ethanol was stirred and heated at reflux for 16 hr. The mixture was filtered and the filtrate was evaporated under reduced pressure to yield a semisolid residue. The residue was partitioned between methylene chloride and a 15% sodium hydroxide solution (300 ml of each). The organic layer was washed with two 300 ml portions of water, dried over magnesium sulfate and the solvent was evaporated under reduced pressure to give 34.2 g (50%) of the title compound as a viscous oil.

PREPARATION 13

2-(3,4-Dichlorophenoxy)ethanol

The title compound was prepared by reduction of 2-(3,4-dichlorophenoxy)acetic acid (Aldrich, 96% pure) with borane in tetrahydrofuran (Aldrich, 1M solution) using the procedure of N. M. Yoon, et al. in J. Org. Chem 38(#16) p. 2786 (1973). The yield was 91% of theory.

PREPARATION 14

3-Benzoylpropanol

A solution of 35.6 g (0.20 mole) of benzoylpropionic acid in 100 ml of tetrahydrofuran was added dropwise to 300 ml of a 1 molar solution of borane tetrahydrofuran complex in tetrahydrofuran. The mixture was stirred at ambient temperatures for 60 hr, giving a gel. This was treated with 100 ml of 2N hydrochloric acid solution and the mixture stirred for 15 min. Most of the tetrahydrofuran was removed on a rotary evaporator and the residue partitioned between methylene chloride and water. The aqueous layer was extracted again with methylene chloride. The combined extract was washed with water, dried (sodium sulfate), and concentrated to yield 24.30 g of 1-phenyl-1,4-butanediol. This intermediate was dissolved in acetone and heated at reflux temperature for 5 hr while 30 g of manganese dioxide was added in five portions. The reaction mixture was filtered and concentrated to a brown oil that was chromatographed on silica gel using 15% ethyl acetate-85% methylene chloride to elute the fraction identified by $^1H$ nmr as the title compound. The fraction weighed 11.20 g, after concentration and was shown to have a purity greater than 90%.

PREPARATION 15

1-(3-Hydroxypropyl)indoline

A stirred reaction mixture consisting of 22.5 ml (0.20 mole) of indoline, 29.8 ml (0.3 mole) of 3-chloropropanol, 41.4 g (0.30 mole) of potassium carbonate, 0.5 g of tetra-n-butylammonium bromide, 150 ml of toluene, and 50 ml of water was heated at reflux temperature for 5 hr. An additional 15 ml (0.15 mole) of 3-chloropropanol was added and reflux continued for an additional 23 hr. Thin layer chromatographic (TLC) analysis (10% ethyl acetate in methylene chloride) showed the reaction to be about 50% complete. Additional potassium carbonate (20 g), tetra-n-butylammonium bromide (0.5 g) and 3-chloropropanol (15 ml) were added to the reaction mixture which was then heated at reflux temperature for another 18 hr. Tlc analysis showed the reaction to be 66% complete. The mixture was diluted with water and toluene. The toluene layer was separated, washed twice with water, and then extracted twice with 2N hydrochloric acid solution. The acid extracts were washed once with toluene and combined. Toluene was added to the acid extract and the mixture basified by agitating while adding 50% sodium hydroxide solution. The organic layer was separated, washed with water, and the wash back-extracted with toluene. The toluene solutions were combined, dried (sodium sulfate) and concentrated to give 25.7 g of a dark brown oil which was purified by chromatography on a 300 g column of silica gel using increasing portions of ethyl acetate in methylene chloride to elute the desired product (12.3 g).

PREPARATION 16

1-(3-Hydroxypropyl)indole

In an exothermic reaction, a solution of 7.0 g (0.042 mole) of 1-(3-hydroxypropyl)indoline in 50 ml of acetone was added in a thin stream to a stirred suspension of 14 g of activated manganese dioxide in 100 ml of acetone. The mixture was stirred for 1 hr without addition of heat and then heated to reflux temperature for 1 hour. The reaction mixture was filtered and the filter cake washed with additional acetone. The filtrate, containing suspended solids, was treated with activated charcoal and filtered through a sintered glass funnel. The clear filtrate was evaporated to obtain 6.4 g of brown oil shown by $^1$H nmr and mass spectral analyses to be the title compound.

PREPARATION 17

2-(8-Quinolyloxy)ethanol

A mixture of 14.5 g (0.10 mole) of 8-hydroxyquinoline, 13.5 ml (0.20 mole) of chloroethanol, 40 g (0.30 mole) of potassium carbonate, and 200 ml of acetone was stirred at reflux temperature for 26 hr. The mixture was filtered and the filtrate concentrated to an oil. The oil was partitioned between toluene and aqueous potassium carbonate solution. When the toluene solution was shaken with a fresh portion of potassium carbonate solution, an off-white solid crystallized out of solution. The solid was collected by filtration and the organic layer of the filtrate extracted twice with potassium carbonate solution. The toluene solution was concentrated to obtain a black oil. The oil was redissolved in toluene and upon treating the solution with a few drops of water, a solid crystallized from solution. This solid was collected by filtration and combined with the previously obtained solid. The solid was dissolved in hot methylene chloride, stirred with magnesium sulfate and charcoal, filtered, and concentrated to an oil. The oil was crystallized by dissolving in toluene and wetting the solution with a few drops of water, affording two crops of solid (5.5 g) which was shown by $^1$H nmr to be a dihydrate. The dihydrate was dissolved in a mixture of methylene chloride and toluene. The solution was dried (sodium sulfate), and concentrated to give 5.4 g of the anhydrous product as an oil.

PREPARATION 18

2-(3-Pyridyloxy)ethanol

This compound was prepared according to the procedure in Preparation 17. Thus, reacting 14 g (0.15 mole) of 3-hydroxypyridine with 27 ml (0.4 mole) of 2-chlorethanol and 85 g of potassium carbonate in 150 ml of 2-butanone at reflux temperature gave 4.9 g of the title compound after column chromatography (5% methanol in methylene chloride on silica gel).

PREPARATION 19

Sulfamoyl chloride

A solution of 3.45 ml (0.1 mole) of 96% formic acid in 10 ml of acetonitrile was added over 15 min to a chilled (15° C.) solution of 8.87 ml (0.1 mole) of chlorosulfonyl isocyanate in 20 ml of acetonitrile. The reaction mixture was then stirred at ambient temperature for 3 hr (evolution of gas ceased during this time). This solution can be stored (0° C.) for future use.

PREPARATION 20

N-Isopropylsulfamoyl chloride

This was prepared in 47% yield from isopropylamine hydrochloride, sulfuryl chloride, and antimony (V) pentachloride in acetonitrile, using the procedure of G. Weis and G. Shulze, *Liebigs. Ann. Chem.* 729,40 (1969).

PREPARATION 21

N-(t-Butylsulfamoyl) chloride

This compound was prepared in 12% yield from t-butyl amine hydrochloride, sulfuryl chloride, and antimony (V) pentachloride in acetonitrile using the procedure of G. Weis and G. Schulze, *Liebigs. Ann. Chem.* 729,40 (1969).

PREPARATION 22

N-Methylsulfamoyl chloride

This compound was prepared in approximately 80% yield from methylamine hydrochloride, sulfuryl chloride, and antimony (V) pentachloride in acetonitrile using the procedure of G. Weis and G. Schulze, *Liebigs. Ann. Chem.* 729,40 (1969).

PREPARATION 23

N-Ethylsulfamoyl chloride

This compound was prepared in 67% yield from ethylamine hydrochloride, sulfuryl chloride, and antimony (V) pentachloride in acetonitrile using the procedure of G. Weis and G. Schulze, *Liebigs. Ann. Chem.* 729,40 (1969).

PREPARATION 24

3-Hydroxy-4-phenyl-1,2,5-thiadiazole

3-Hydroxy-4-phenyl-1,2,5-thiadiazole was prepared from 2-amino-2-phenyl acetamide and sulfur monochloride in dimethylformamide in 85% yield using the procedure of L. M. Weinstock et al., *J. Org. Chem.* 32,2823 (1967).

PREPARATION 25

2-Phenoxy-1,3-propanediol

To a stirred solution of 11.9 g (0.517 mole) of sodium in 500 ml of absolute ethanol was added in portions 48.4 g (0.514 mole) of phenol. After stirring a few minutes to form the sodium phenoxide, 100 g (0.514 mole) of diethyl 2-chloromalonate was added dropwise. The reaction mixture was then heated at reflux temperature for 5 hr. The mixture was concentrated in vacuo and the residue treated with 500 ml of water. This mixture was extracted with three 300 ml portions of ether. The combined extract was washed with 300 ml of water, dried (magnesium sulfate) and concentrated to obtain 107 g (82% yield) of diethyl 2-phenoxymalonate.

A solution of 84.7 g of the ester in 250 ml anhydrous ether was added dropwise to a stirred suspension of 14.1 g (0.372 mole) of lithium aluminum hydride in 350 ml of anhydrous ether at such a rate so as to maintain a gentle reflux. When the addition was completed the mixture was stirred at ambient temperature for 2 hr and then treated cautiously with successive dropwise additions of 14 g of water, 42 g of 15% sodium hydroxide solution, and 42 g of water while the mixture was stirred vigorously. The mixture was then treated with 300 ml of ethyl acetate and stirred for a few minutes. The mixture was then filtered, the filter cake washed with an additional 300 ml of ethyl acetate, and the combined filtrate layers washed twice with 400 ml portions of water. The organic solution was dried (magnesium sulfate) and concentrated in vacuo to give 39 g (69% yield) of the title compound as a viscous oil.

PREPARATION 26

1,1-Dimethyl-2-phenoxyethanol

To a stirred solution of 24.2 g (0.16 mole) of phenoxy-2-propanone (Eastman) in 150 mL of dry ethyl ether was added 56 ml (0.17 mole) of methylmagnesium bromide (3.0M solution in ethyl ether, Aldrich) and the reaction mixture was stirred at ambient temperature under a nitrogen atmosphere for 4 hr. The reaction mixture was treated with 100 ml of saturated ammonium chloride solution and vigorously stirred for 1 hr. The layers were separated and the organic layer was washed twice with 200 ml portions of water, dried (magnesium sulfate) and the solvent evaporated under reduced pressure to yield 24.3 g (91%) of a vicous oil. A 2.3 g sample of the oil was purified by high pressure liquid chromatography (Waters Associates Prep LC/System 500 A, PrepPak ® 500 silica, ethyl acetate-hexanes, 1:20, flow rate 150 ml/min). The desired fractions were combined and the solvents evaporated under reduced pressure to yield 2.1 g (91% recovery) of the title compound as a colorless liquid.

Analysis: Calculated for $C_{10}H_{14}O_2$: C, 72.26; H, 8.49. Found: C, 72.08; H, 8.46.

PREPARATION 27

3-(1H-Imidazol-1-yl)phenol

This compound was prepared by modifying a procedure of L. M. Sitkina and A. M. Simonov abstracted in CA 65:1386e.

Imidazole (34 g, 0.5 mole), m-bromoanisole (51 mL, 0.4 mole), potassium carbonate (52 g), and cuprous chloride (2.4 g) in 300 ml N-methyl-2-pyrrolidone was heated at reflux for 4 hours. The cooled mixture was diluted with water and 100 ml concentrated ammonium hydroxide. The product was extracted into toluene-ethyl acetate (several times until TLC of aqueous layer showed only a trace amount of product). All the organic extracts were combined, filtered, extracted once with water and then three times with a total of 300 ml 48% hydrobromic acid. The hydrobromic acid extracts were combined and heated at reflux for 6 hours and then concentrated. The residue was redissolved in water and basified first with sodium hydroxide and at the end with sodium bicarbonate to get a final pH of 8. Some isopropyl ether was added to cause the product to crystallize out. The solid was filtered, rinsed with water, and dried at 80° C. in a vacuum oven to obtain 50.9 g (79.5% yield). A small portion of this solid was dissolved in absolute ethanol, filtered, concentrated, and recrystallized. The recrystallized material melted at 169°-170° C.

Analysis: Calculated for $C_9H_8N_2O$: C, 67.49; H, 5.03; N, 17.49. Found: C, 67.28; H, 5.12; N, 17.16.

PREPARATION 28

R-(−)2,2-Dimethyl-4(2-methoxyphenoxy)-1,3-dioxolane

This compound was prepared from 5.72 g (0.02 mole) of S(+)-3-tosyloxy-1,2-propanediol acetonide and 0.03 mole of sodium guaiacolate in 76% yield according to the procedure of W. L. Nelson et al., *J. Org. Chem.* 42, 1066, 1977. Mp=43°-44° C., $[\alpha]_D^{22} -8.0°$ (C=2 in dimethylformamide).

Analysis: Calculated for $C_{13}H_{18}O_4$: C, 65.53; H, 7.61. Found: C, 65.38; H, 7.45.

PREPARATION 29

S-(+)2,2-Dimethyl-4-(2-methoxyphenoxy)-1,3-dioxolane

This compound was prepared from 49.4 g (0.173 mole) of R(−)-3-tosyloxy-1,2-propanediol acetonide and 0.26 mole of sodium guaiacolate in 68% yield according to the procedure of W. L. Nelson et al., *J. Org. Chem.* 42, 1066, 1977. Mp=44.5-45.5, $[\alpha]_D^{22} +8.5°$ (C=2 in dimethylformamide).

Analysis: Calculated for $C_{13}H_{18}O_4$: C, 65.53; H, 7.61. Found: C, 65.53; H, 7.69.

PREPARATION 30

S-(+)-Glyceryl guaiacolate

Hydrolysis of 20 g (0.084 mole) of R-(−)-2,2-dimethyl-4(2-methoxyphenoxy)-1,3-dioxolane according to the procedure of W. L. Nelson et al, *J. Org. Chem.* 42, 1066 (1977) gave 14.2 g (85%) of the title compound, mp 93°-94.5° C., $[\alpha]_D^{22} +8.80°$ (C=2 in methanol).

Analysis: Calculated for $C_{10}H_{14}O_4$: C, 60.60; H, 7.12. Found: C, 60.53; H, 6.98.

PREPARATION 31

R-(−)Glyceryl guaiacolate

Hydrolysis of 27.0 g (0.113 mole) of S-(+)-2,2-dimethyl-4(2-methoxyphenoxy)-1,3-dioxolane according to the procedure of W. L. Nelson et al, *J. Org. Chem.* 43, 1066 (1977) gave 21.5 g (96%) of the title compound, mp 93.5°-95° C., $[\alpha]_D^{22} -9.05°$ (C=2 in methanol).

Analysis: Calculated for $C_{10}H_{14}O_4$: C, 60.60; H, 7.12. Found: C, 60.56; H, 7.05.

PREPARATION 32

3-(4-Phenyl-1H-imidazol-1yl)phenol

Following the procedure for preparation of 3-(1H-imidazol-1-yl)phenol (preparation 29), 4-phenylimidazole (20 g, 0.138 mole) and 3-bromoanisole (32 ml, 0.25 mole) were reacted to give the title compound in 57% yield; mp 195°-197° C.

Analysis: Calculated for $C_{15}H_{12}O$: C, 76.25; H, 11.86. Found: C, 75.98; H, 11.67.

PREPARATION 33

2-[3-(1H-Imidazol-1-yl)phenoxy]ethanol

A slurry of 16.0 g (0.10 mole) of 3-(imidazol-1-yl)phenol and 42 g (0.3 mole) of potassium carbonate in 100 ml of methyl ethyl ketone was heated to reflux with stirring. The mixture was treated with 25.5 g (0.3 mole) of chloroethanol by dropwise addition over a 2 hr period. The mixture was heated at reflux for an additional 18 hr then treated with an additional 16.1 g (0.2 mole) of chloroethanol and 27.6 (0.2 mol) of potassium carbonate. After an additional 22 hr heating at reflux all starting material was consumed. The reaction mixture was filtered and the filtrate was concentrated. The residue was partitioned between methylene chloride and 0.1N sodium hydroxide solution. The organic layer was concentrated and the residue was crystallized from ethyl acetate to give 10.2 g (50%) of the title compound as tan crystals, mp 81.0°-83.0° C.

Analysis: Calculated for $C_{11}H_{12}N_2O_2$: C, 64.69; H, 5.92; N, 13.72. Found: C, 64.50; H, 5.87; N, 13.56.

PREPARATION 34

3-(2-Ethoxyphenoxy)-1,2-propanediol

A solution of 41.5 g (0.3 mole) of 2-ethoxyphenol, 29.6 g (0.4 mole) of glycidol, 2 ml of pyridine and 150 ml of absolute ethanol was heated at reflux temperature for 18 hr. The mixture was concentrated to a thick oil that crystallized slowly over several days. The crude product was chromatographed on a silica gel column (1.2 kg) using increasing portions of acetone in methylene chloride to elute the product. The desired fractions were combined and concentrated to give a yellow oil that crystallized on standing. The solid was triturated with petroleum ether and the mixture filtered to obtain 41.8 g of solid. Recrystallization from carbon tetrachloride yielded 37.2 g (58%) of white solid, mp 64°-65° C.

Analysis: Calculated for $C_{11}H_6O_4$: C, 62.25; H, 7.60. Found: C, 62.34; H, 7.72.

PREPARATION 35

3-[4-(1H-Imidazol-1-yl)phenoxy]-1-propanol

A stirred mixture of 4(1H-imidazol-1-yl)phenol (16.0 g, 0.10 mole), 3-chloropropanol (19.0 g, 0.20 mole), potassium carbonate (28 g, 0.20 mole) and methyl ethyl ketone (100 ml) was heated at reflux temperature for 24 hr. The reaction mixture was cooled, filtered, and the filtrate concentrated. The residue was partitioned between ethyl acetate and 0.01N sodium hydroxide solution. The ethyl acetate layer was dried (magnesium sulfate), diluted with ether, and the solid precipitate collected. The solid was recrystallized from methyl isobutyl ketone to obtain 10.0 g (46%), mp 76°-78° C.

Analysis: Calculated for $C_{12}H_{19}N_2O_4$: C, 66.04; H, 6.47; N, 12.84. Found: C, 65.87; H, 6.48; N, 12.71.

PREPARATION 36

2-[4-(1H-1,2,4-Triazol-1-yl)phenoxy]ethanol

A stirred mixture of 4(1H-1,2,4-triazol-1-yl)phenol (16.1 g, 0.10 mole), 2-chloroethanol (25.5 g, 0.30 mole), potassium carbonate (42 g, 0.30 mole) and methyl ethyl ketone (100 ml) was heated at reflux temperature for 10 hr. An additional 16.1 g (0.20 mole) of 2-chloroethanol was added to the reaction mixture and heating at reflux temperature continued for another 24 hr. The hot mixture was filtered and the filtrate chilled. The crystalline precipitate was collected by filtration and the filter cake rinsed with water to remove most of the dark color. The solid was triturated with hot ethyl acetate, the mixture cooled, and the light tan crystals collected to yield 14.0 g (68%); mp 151°-152° C.

Analysis: Calculated for $C_{10}H_{11}N_3O_2$: C, 58.53; H, 5.40; N, 20.48. Found: C, 58.35; H, 5.36; N, 20.27.

PREPARATION 37

3-(2-Methyl-1H-imidazol-1-yl)phenol

A stirred mixture of 3-bromoanisole (100 g, 0.53 mole), 2-methylimidazole (41 g, 0.50 mole), potassium carbonate (96 g, 0.60 mole), cuprous chloride (2.5 g) and N-methyl-2-pyrrolidinone (300 ml) was heated at reflux temperature for 15 hr and then concentrated to remove the solvent and excess 3-bromoanisole. The residue was partitioned between ethyl acetate and water. The ethyl acetate layer was concentrated to a black syrup that was then dissolved in toluene and extracted twice with water and then extracted with 48% hydrobromic acid solution. The hydrobomic acid extract was heated at reflux temperature for 7 hr and then distilltion of water and methylbromide was begun with addition of additional 48% hydrobromic acid solution as necessary to maintain a reasonable volume. Distillation was continued until the distillation head temperature reached 124° C. The mixture was concentrated under vacuum. The concentrate was diluted with 500 ml of water and basified to pH 8 with addition of potassium carbonate in small portions. The precipitate was collected, washed with water, and dried to give 39.7 g. Recrystallization from 50% aqueous ethanol gave 31.4 g (36%), mp 178°-181° C.

Analysis: Calculated for $C_{10}H_{10}N_2O$:C, 68.95; H, 5.79; N, 16.08. Found: C, 68.71; H, 5.75; N, 15.94.

PREPARATION 38

2-Methyl-2-phenoxy-1-propanol

This compound was prepared in 94% yield by reduction of 2,2-dimethylphenoxyacetic acid with a 1 molar solution of borane-tetrahydrofuran in tetrahydrofuran (Aldrich Chemical Co.) using the procedure of N. M. Yoon et al, *J. Org. Chem.* 38, 2786 (1973).

PREPARATION 39

3-(4-Methyl-1H-imidazol-1-yl)phenol

A mixture of 3-bromoanisole (25.5 ml, 0.2 mole), 4-methyl-imidazole (21 g, 0.25 mole), potassium carbonate (26 g), and cuprous chloride (1.2 g) in 150 ml N-methyl-2-pyrrolidone was reacted and worked up as described in Preparation 29.

The phenolic product isolated as precipitate from water had a slightly wet weight of 31 g and $^{13}$C NMR showed a 4:1 isomer ratio. This solid was dissolved in hot isopropyl alcohol, charcoaled, filtered, concentrated, and crystallized to give 11.69 g of off-white solid. $^{13}$C NMR showed only the major isomer, mp 203°–5° C.

Analysis: Calculated for $C_{10}H_{10}N_2O$: C, 68.95; H, 5.79; N, 16.08. Found: C, 69.32; H, 5.68; N, 16.08.

PREPARATION 40

2-(2-Methoxyphenoxy)ethanol

A solution of 43.2 g (0.35 mole) of 2-methoxyphenol (guaiacol, Aldrich) in 200 ml of ethanol was stirred and treated with 29 ml (0.36 mole) of 50% sodium hydroxide solution. To this solution was added a solution of 28.2 g (0.35 mole) of 2-chloroethanol (Aldrich) in 50 ml of ethanol and the reaction mixture was heated at reflux for 2 hr. The solids were removed by filtration. The filtrate was evaporated under reduced pressure and the viscous residue was partitioned between 300 ml of 15% sodium hydroxide solution and 500 ml of ethyl ether. The organic layer was washed with 200 ml of 15% sodium hydroxide solution, 300 ml of water, dried (magnesium sulfate) and the solvent evaporated under reduced pressure to give 24.5 g (42%) of the title compound as a lightly colored viscous oil.

An analytical sample was prepared from this oil by high pressure liquid chromatography purification (Waters Associates Prep LC/System 500 A, PrepPAK® 500 silica, ethyl acetate-hexanes, 1:2, flow rate 200 ml/min). Fractions containing the title compound were combined and the solvents evaporated under reduced pressure to yield the title compound as a colorless liquid.

Analysis: Calculated for $C_9H_{12}O_3$: C, 64.27; H, 7.19. Found: C, 63.93; H, 7.32.

PREPARATION 41

2-[3-(4-Methyl-1H-imidazol-1-yl)phenoxy]ethanol monohydrochloride

A mixture of 3-(4-methyl-1H-imidazol-1-yl)phenol (13.1 g, 0.075 mole), chloroethanol (20.2 ml, 0.3 mole), and potassium carbonate (42 g, 0.3 mole) were heated at a reflux temperature in 200 ml methyl ethyl ketone for 7 hours. Additional chloroethanol (10 ml) was added to the reaction and it was kept at reflux temperature overnight. The solid was filtered and rinsed with acetone. The filtrate and rinsings were concentrated to an oil and dissolved in 1:1 acetonitrile-toluene. The solid was dissolved in water and the solution was used to extract the organic solution. The aqueous layer was separated and extracted once more with 1:1 acetonitrile-toluene. The organic layers were washed with a potassium carbonate solution, dried, filtered, and concentrated to give 16.7 g of dark brown oil. The oil was dissolved in 2-propanol and acidified with a solution of anhydrous hydrogen chloride in 2-propanol and the salt crystallized from 2-propanol/isopropyl ether. The brown solid was collected and recrystallized from 2-propanol to yield 9.07 g of light brown solid which was dried in a vacuum oven overnight at 60° C., mp 164°–165° C.

Analysis: Calculated for $C_{12}H_{14}N_2O_2 \cdot HCl$: C, 56.59; H, 5.94; N, 11.00. Found: C, 56.44; H, 6.03; N, 10.90.

PREPARATION 42

2-(4-Chlorophenoxy)-1,3-propanediol

To a stirred slurry of 11.4 g (0.3 mole) of lithium aluminum hydride (LAH) in 200 ml of freshly distilled (from LAH) tetrahydrofuran (THF) was added dropwise a solution of 57.3 g (0.2 mole) of 2-(4-chlorophenoxy)-1,3-propanedioic acid diethyl ester (CA 59:5051f (1963); Mamaev and Mikhaleva, *Isv. Sibirsk. Otd. Akad. Nauk. SSSR*, 145-8 (1962)) in 150 ml of THF at such a rate that a gentle reflux was maintained. The mixture was stirred at ambient temperature for 5 hr and then the excess LAH was decomposed with successive, cautious, dropwise additions of 11.4 ml of water, 11.4 ml of a 15% sodium hydroxide solution, and 34 ml of water. A gelatinous precipitate developed which was filtered through Celite® with great difficulty. The filtrate was concentrated and the residue was purified by column chromatography on 500 g of silica gel eluted with 0–35% acetone in benzene. The appropriate fractions were combined and concentrated to give an oil which gradually crystallized. The solid was triturated with petroleum ether (30°–60° C.), collected by filtration, and dried to yield 18.2 g (45%) of white solid, mp 62°–64° C. (isopropyl ether).

Analysis: Calculated for $C_9H_{11}ClO_3$: C, 53.35; H, 5.47. Found: C, 53.51; H, 5.52.

EXAMPLE 1

[(1-methylethoxy)carbonyl]sulfamic acid 1-[(2-methoxyphenoxy)methyl]-1,2-ethanediyl ester a. Preparation of the isopropyl ester of N-chlorosulfonyl carbamic acid To a solution of 154 g (1.09 mole) of chlorosulfonyl isocyanate in 300 ml of methylene chloride with agitation and cooling in an ice bath was added a solution of 83.2 ml (1.09 mole) of 2-propanol in 100 ml of methylene chloride over a 26 minute period. The ice bath was removed after addition was complete and the mixture was stirred for 2.5 hr. The mixture was filtered through a Celite® cake to remove a small amount of solid. The filtrate was concentrated to a solid. The solid was triturated in petroleum ether and collected on a filter under nitrogen atmosphere, washed with more petroleum ether and dried under vacuum in a desicator to give 212.7 g (96.5%) of the isopropyl ester of N-chlorosulfonyl carbamic acid.

b. Preparation of the title compound

Into a stirred solution of the 20.1 g (0.10 mole) of the isopropyl ester of N-chlorosulfonyl carbamic acid in 30 ml of methylene chloride, cooled by an ice bath was poured a suspension of 8 g (0.04 mole) of 3-(2-methoxyphenoxy)-1,2-propanediol (which is glyceryl guaiacolate) in a 8.1 ml (0.1 mole) of pyridine. Exothermic reaction caused gentle boiling. The ice bath was removed after the addition and stirring was continued for 2 hr. Water, 80 ml, was added to the reaction mixture and stirring continued for 20 min additional time. The organic layer was separated and washed twice more with water. The organic layer was extracted three times with sodium bicarbonate solution. The combined bicarbonate solution containing the product was stirred with methylene chloride in an ice bath with adding sulfuric acid to acidifying the mixture. The layers were separated and the aqueous layer was extracted once with methylene chloride. The methylene chloride layers were combined, washed with water, dried over sodium sulfate, filtered and concentrated to give 23 g of an oil. $^1$H NMR analysis showed title compound with a small contamination of methylene chloride. A 10 g portion of the oil in benzene was freeze-dried in an attempt to obtain solid; however an oil resulted. $^1$H NMR analysis showed methylene chloride had been exchanged for benzene in amount of about 0.25 mole benzene per mole of title compound.

Analysis: Calculated for $C_{18}H_{28}N_2O_{12}S_2$: C, 40.90; H, 5.34; N, 5.30. Found: C, 42.40; H, 5.47; N, 5.00.

EXAMPLE 2

[(1-methylethoxy)carbonyl]sulfamic acid 1-[(2-methoxyphenoxy)methyl]-1,2-ethanediyl ester zinc complex dihydrate compound with 2-propanol (2:1)

To a solution of 22.39 g (0.042 mole) of [1-[(2-methoxyphenoxy)methyl]-1,2-ethanediylbis(oxysulfonyl)]biscarbamic acid bis 1-methylethyl ester (from Example 1) in methanol was added a light suspension of barium hydroxide octahydrate in water. The resulting basic mixture was stirred for 1.5 hr and then filtered through Celite ®. The filtrate was then concentrated to a solid residue which was redissolved in water and stirred with Celite ® while a solution of of zinc sulfate hydrate in water was added in portions until no further precipitation occurred. The mixture was filtered. The aqueous zinc salt solution was evaporated to an oil which was mixed with isopropyl alcohol (IPA), water and isopropyl ether and stirred overnight. The light suspension was filtered to give 0.7 g of solid. The filtrate was concentrated and pumped (under reduced pressure) to a white, solid foam. This solid was triturated in isopropyl ether, collected and pumped at room temperature overnight to give 17 g of white solid, mp with decomposition >80° C.

Analysis: Calc'd for $C_{18}H_{26}N_2S_2O_{12}Zn \cdot 2H_2O \cdot \frac{1}{2}IPA$: C, 35.60; H, 5.21; N, 4.26; Zn, 9.90. Found: C, 35.87; H, 5.08; N, 4.87; Zn, 8.64.

EXAMPLE 3

Sulfamic acid 1-[(2-methoxyphenoxy)methyl]-1,2-ethanediyl ester a. Preparation of sulfamoyl chloride solution in excess acetonitrile To a solution of 13.1 ml (0.15 mole) of chlorosulfonyl isocyanate in 20 ml of acetonitrile with agitation and cooling in an acetone-ice bath was added slowly dropwise a solution of 2.7 ml (0.15 mole) of water in 10 ml (excess) acetonitrile at −5° C. to +5° C. over a 15 min period. Upon addition of each drop, vigorous evolution of carbon dioxide was noted. The solution was stirred in the cold bath for 15 minutes after addition was complete.

b. Preparation of the title compound

To the above prepared sulfamoyl chloride solution was added 8 g (0.04 mole) of 3-(2-methoxyphenoxy)-1,2-propanediol (which is glyceryl guaiacolate) in a solution of 15.2 ml (0.176 mole) of pyridine in 20 ml of acetonitrile at −3° C. to +15° C. over a 13 min period. The cold bath was removed and the reaction mixture was stirred for 2 hr. Ethyl acetate, 30 ml, was added and the mixture was extracted thrice with saturated sodium chloride solution. The aqueous layers were back extracted twice with a 1:1 vol mixture of ethyl acetate:acetonitrile. The organic layers were combined and dried over sodium sulfate and evaporated to give a glassy residue. Crystallization using isopropyl alcohol and isopropyl ether produced 10.3 g (74.5%) of slightly impure title product in 2 crops. The crystals were triturated with water and a small amount of isopropyl alcohol and then subjected to filtration, dried and dissolved in warm acetonitrile. A small amount of solid was removed by filtration. The filtrate was mixed with water and subjected to slow evaporation. The resulting suspension was filtered and the solid was rinsed with water, isopropyl alcohol and isopropyl ether. The white solid was dried in a vacuum oven at 40° C. overnight, mp 151°–153° C.

Analysis: Calculated for $C_{10}H_{16}N_2O_8S_2$: C, 33.70; H, 4.53; N, 7.86. Found: C, 34.16; H, 4.65; N, 8.20.

EXAMPLE 4

Methyl sulfamic acid 1-[(2-methoxyphenoxy)methyl]-1,2-ethanediyl ester a. Preparation of N-methylsulfamoyl chloride A mixture of 16.2 g (0.235 mole) of 98% purity methylamine hydrochloride, 19.4 ml (0.235 mole) of 97% purity sulfuryl chloride and 0.2 ml of anitmony (V) chloride in 70 ml of acetonitrile was heated at reflux for 4 hr. To the reaction mixture was added another 19.4 ml (0.235 mole) of sulfuryl chloride and reflux was continued overnight. The reaction mixture changed from a suspension to a brown solution. The solution was concentrated under reduced pressure and then pumped under vacuum to give 30 g of brown oil. $^1$H NMR analysis showed the oil to be mainly N-methylsulfamoyl chloride.

b. Preparation of title compound

A solution of 8 g (0.04 mole) of 3-(2-methoxyphenoxy)-1,2-propanediol (which is glyceryl guaiacolate) in 13 ml (0.16 mole) of pyridine and 40 ml of methylene chloride was added in a thin stream to a solution of 20.72 g (ca. 0.16 mole) of the crude N-methylsulfamoyl chloride prepared above in 60 ml of methylene chloride while stirring in a room temperature water bath. After 2 hr stirring, the reaction mixture was extracted twice with water. The organic layer was dried over sodium sulfate, filtered and concentrated to 20.42 g of brown oil. This oil was purified by column chromatography on silica gel column, eluting with 10% ethyl acetate in methylene chloride to give the title compound as a viscous oil.

Analysis: Calculated for $C_{12}H_{20}N_2O_8S_2$: C, 37.49; H, 5.24; N, 7.29. Found: C, 37.07; H, 5.29; N, 7.14.

EXAMPLE 5

1,4:3,6-Dianhydro-D-glucitol disulfamate

To an agitated solution of ca. 0.30 mole of sulfamoyl chloride in acetonitrile as prepared in Example 3 (twice the amounts shown) was added 14.90 g (0.10 mole) of isosorbide in pyridine and acetonitrile at −3° to 15° C., while cooling in an ice bath. The cold bath was removed and the reaction mixture was stirred. The mixture was extracted with ethyl acetate as in Example 3, the extract washed, dried and evaporated to give about 20 g of brown oil as crude title product. The oil was chromatographed on 400 g silica gel eluting with 15% methanol in methylene chloride. A heart cut of the fractions gave 9.5 g of oil. The oil was subjected to reduced pressure in a vacuum oven at 40° C. overnight.

Analysis: Calculated for $C_6H_{12}N_2O_8S_2$: C, 23.68; H, 3.98; N, 9.21. Found: C, 23.46; H, 4.12; N, 9.07.

EXAMPLE 6

Sulfamic acid 2,2-bis[(aminosulfonyloxy)methyl]-1,3-propanediyl ester a. Preparation of benzyloxycarbonylsulfamoyl chloride To a solution of 43.5 ml (0.5 mole) of chlorosulfonyl isocyanate in 400 ml of methylene chloride, stirred in an ice bath, was added 51.6 ml (0.5 mole) of benzyl alcohol over an one hr period. The reaction mixture was concentrated under reduced pressure and the solid residue was triturated in petroleum ether (bp range 35°-65° C.). The solid was collected by filtration, rinsed twice with petroleum ether and dried under vacuum to give 110 g (88% yield) of benzyloxycarbonylsulfamoyl chloride.

b. Preparation of title compound

To a solution of 25 g (0.1 mole) of the benzyloxycarbonylsulfamoyl chloride prepared above in 50 ml of acetonitrile were added 2.62 g (0.02 mole) of pentaerythritol (solid) and 50 ml pyridine dropwise in 5 min. The mixture was stirred without heating or cooling to give a clear brown solution in ½ hr. After stirring overnight, the solvents were evaporated. The residual oil was dissolved in methylene chloride and extracted twice with dilute hydrochloric acid. The aqueous layers were back extracted with methylene chloride. The organic layers were combined and dried over sodium sulfate, filtered, evaporated and vacuum pumped to a foamy solid weighing 19.94 g. The foamy solid was dissolved in 150 ml tetrahydrofuran (THF) and 50 ml of water. The solution was mixed with 3 g of 5% palladium on carbon catalyst and hydrogenated at room temperature under about 50 psi hydrogen overnight. The catalyst was removed by filtration and the filtrate was concentrated. The residue was triturated in acetonitrile to give 2 g of sticky solid A. The mother liquor was concentrated and triturated in acetonitrile to give 2 g of solid B. The mother liquor of solid B was concentrated and triturated in water and isopropyl ether to give some white solid C. Solid samples A and B were combined and triturated in water and isopropyl ether to give white solid D. Solid samples C and D were combined, dissolved in aqueous THF and the mixture filtered and the filtrate evaporated to give a residue. This residue was triturated with acetonitrile to give 3.5 g solid title compound, mp 200°-202° C.

Analysis: Calculated for $C_5H_{16}N_4O_{12}S_4$: C, 13.27; H, 3.56; N, 12.38. Found: C, 13.59; H, 3.72; N, 12.22.

EXAMPLE 7

Sulfamic acid 1-(phenoxymethyl)-1,2-ethanediyl ester a. Preparation of sulfamoyl chloride in excess acetonitrile To a solution of 24.8 g (0.175 mole, 15.2 ml) of chlorosulfonyl isocyanate in 100 ml of acetonitrile cooled in an ice-acetone bath was added dropwise a solution of 32 g (0.175 mole) of water in 10 ml of acetonitrile at such a rate that the temperature did not exceed 7° C. (45 min). The mixture was stirred at −3° C. for 15 min after addition was complete.

b. Preparation of title compound

To the above sulfamoyl chloride solution in acetonitrile was added dropwise with stirring a solution of 8.4 g (0.05 mole) of 3-phenoxy-1,2-propanediol (95% purity obtained from Aldrich Chem. Co., Inc.) and 20.2 g (0.2 mole) of triethylamine in 50 ml of acetonitrile at such a rate that the temperature did not exceed 12° C. over a 45 min period. The cooling bath was removed and the mixture was stirred for 2 hr and treated with 100 ml of ethyl acetate and 50 ml of water. The mixture was vigorously stirred for 5 min and the layers were separated. The organic layer was washed with 50 ml of water and 100 ml of salt brine, dried over sodium sulfate and concentrated to give a gum as residue. The gum was purified by column chromatography on 350 g of silica gel. Fractions eluted with 15% acetone in methylene chloride were combined and concentrated to give a clear gum as residue. The gum was triturated with petroleum ether (b.p. 30°-60° C.) to give crystalline solid. The solid was collected by filtration and recrystallized from benzene-acetonitrile to yield 4.2 g (26% yield) of white solid title compound, mp 116°-118° C.

Analysis: Calculated for $C_9H_{14}N_2O_7S_2$: C, 33.12; H, 4.32; N, 8.58. Found: C, 33.16; H, 4.36; N, 8.54.

EXAMPLE 8

1,4:3,6-Dianhydro-D-glucitol monosulfamate, mononitrate

A solution of sulfamoyl chloride (0.15 mole) in acetonitrile (30 ml) was prepared in the same manner as described in Example 3.

Isosorbide mononitrate (obtained as a mixture with 10% lactose, (21.2 g, 0.1 mole) was triturated with acetonitrile (80 ml) and filtered to remove the insoluble lactose. This solution of isosorbide mononitrate was mixed with pyridine 12.1 ml (0.15 mole) and then added to the sulfamoyl chloride solution at −8° to +1° C. over one-half hour. The cold bath was removed and the reaction mixture was stirred overnight. The product was worked up in the same way as in Example 3 to give a solid after evaporation. The solid was mostly dissolved in hot 1:1 acetonitrile/ethyl acetate, filtered to remove small amount of inorganic material, and the filtrate was evaporated to give a 29 g of solid. This solid was triturated overnight in water with trace amount of isopropyl alcohol. The suspension was filtered and rinsed twice with water; air dried to give 20 g solids. Recrystallization from isopropyl alcohol gave 14.6 g white solid. The solid was vacuum pumped overnight at room temperature, mp 133°-134° C.

Analysis: Calc'd for $C_6H_{10}N_2O_8S$: C, 26.67; H, 3.73; N, 10.37. Found: C, 26.89; H, 3.77; N, 10.30.

EXAMPLE 9

[(1-methylethoxy)carbonyl]sulfamic acid 2,2-bis[[[(1-methylethoxy)carbonyl]amino]sulfonyloxy]-1,3-propanediyl ester compound with 2-propanol (2:1)

a. Preparation of isopropyl ester of N-chlorosulfonyl carbamic acid in methylene chloride solution To 75 ml of methylene chloride stirred in a cold bath was added 16 ml (0.18 mole) of chlorosulfonyl isocyanate, followed by a solution of 13.8 ml (0.18 mole) of 2-propanol in 25 ml of methylene chloride over a 33 min period at −2° to +6° C. The cold bath was removed at the end of the addition and the reaction mixture was stirred for 2 hr.

b. The solution prepared in (a) was cooled in an ice bath and 4.08 g (0.03 mole) of pentaerythritol was added followed by 0.2 mole of pyridine over a four min period at 2° to 17° C. Some pyridine hydrochloride precipitated. About 100 ml of acetonitrile was added to redissolve the salt. The pentaerythritol dissolved gradually in four hours time. After stirring overnight, the reaction mixture was evaporated to dryness. The solid residue was triturated with water, collected thereafter by filtration and rinsed 3 times with water. The wet solid cake was mostly dissolved in hot isopropyl alcohol. The solution was filtered and the filtrate was concentrated to a small volume and allowed to stand to solidify. The solid was triturated with isopropyl ether, recollected by filtration and rinsed with isopropyl ether. The filter cake was subjected to vacuum drying at room temperature overnight to give 16.64 g of white solid, mp 195°-197° C.

Analysis: Calculated for $C(CH_2OSO_2NH-CO_2C_3H_7)_4.0.5C_3H_8O$: C, 32.68; H, 5.36; N, 6.78. Found: C, 32.34; H, 5.35; N, 6.86.

EXAMPLE 10

[(1-methylethoxy)carbonyl]sulfamic acid 2,2bis[[[(1-methylethoxy)carbonyl]amino]sulfonyloxy]-1,3-propanediyl ester zinc complex hydrate [2:7]compound with 2-propanol [2:1]

The compound obtained in Example 9, i.e. 2,2-bis(hydroxymethyl)-1,3-propanediol-tetrakis [(1-methoxyethoxy)carbonyl]sulfamate (ester) compound with 2-propanol [2:1], was dissolved in methanol and treated with barium hydroxide octahydrate followed by zinc sulfate hydrate in the same manner as Example 2. The aqueous solution of the zinc salt was evaporated to give white solid which was recrystallized from water-isopropyl alcohol (IPA) combination. The solid was rinsed with IPA and isopropyl ether, and dried at 50° C. under vacuum to give 14.6 g of title salt, mp with decomposition, >210° C.

Analysis: Calculated for $C_{21}H_{36}N_4O_{20}S_4Zn_2.3.5 H_2O.0.5$ IPA: C, 26.58; H, 4.66; N, 5.51; Zn, 12.86. Found: C, 26.98; H, 4.89; N, 5.40; Zn, 11.70.

EXAMPLE 11

Sulfamic acid 2-phenoxyethyl ester a. Preparation of sulfamoyl chloride solution in excess acetonitrile To a stirred, cooled (ice-acetone bath) solution of 48.8 g (30.4 ml, 0.342 mole) of chlorosulfonyl isocyanate of 98% purity (Aldrich Chemical Co.) in 150 ml of acetonitrile was added dropwise a solution of 6.4 g (0.356 mole) of water in 20 ml of acetonitrile at such a rate that the temperature did not exceed 7° C. Addition time was 40 min. After the addition was completed, the mixture was stirred at −3° C. for 15 min.

b. Preparation of title compound

To the solution prepared in (a) was added dropwise a solution of 13.8 g (0.1 mole) of 2-phenoxyethanol and 40.4 g (0.4 mole) of triethylamine in 100 ml of additional acetonitrile at such a rate that the temperature did not exceed 12° C. Addition time was 45 min. The cold bath was removed and the mixture was stirred for 2 hr and then treated with 200 ml of ethyl acetate and 100 ml of water. The mixture was vigorously stirred for 5 min and the layers were separated. The organic layer was washed twice with 100 ml of water, twice with 100 ml portions of saturated sodium chloride solution, dried over sodium sulfate and subjected to reduced pressure to remove volatiles to give a viscous, oily residue which solidified on standing. The solid was dissolved in 300 ml of methylene chloride and the solution filtered through Celite ®. The filtrate was concentrated to 200 ml volume and again filtered through Celite ®. The filtrate was concentrated further under reduced pressure to give a solid residue. The residue was recrystallized successively from methylene chloride and ethyl acetate-water mixture to give 10.5 g (48% yield) of title compound as white solid, mp 89°-91° C.

Analysis: Calculated for $C_8H_{11}NO_4S$: C, 44.23; H, 5.10; N, 6.45. Found: C, 43.19; H, 5.08; N, 6.84.

EXAMPLE 12

Sulfamic acid 1,7-heptanediyl ester a. Sulfamoyl chloride solution was prepared as in Example 11 using: 37.9 g (0.262 mole) of chlorosulfonyl isocyanate (98%), 47.0 g (0.261 mole) of water and 170 ml of acetonitrile.

b. The title compound was obtained using the following procedure: The sulfamoyl chloride in acetonitrile solution prepared in (a) was reacted as in Example 11 with 10.5 g (0.0755 mole) of 1,7-heptanediol (95%), 30.3 g (0.300 mole) of triethylamine in 100 ml additional acetonitrile followed by using extracting, washing and concentration procedures of Example 11 through the first evaporation. The viscous residue which solidified on standing was purified by high pressure liquid chromatography using the Waters Associates ® Prep LC/System 500A with PrepPAK ® 500 silica. Eluting solvent used was 10:1 mixture methylene chloride-acetone at a flow rate of 200 ml/min. Fractions containing the title compound were combined and the solvents were evaporated under reduced pressure to give a viscous oil which solidified on standing. The solid was recrystallized from wet methylene chloride to give 8.2 g (37% yield) of title compound as white solid, mp 88.5°-90.5° C.

Analysis: Calculated for $C_7H_{18}N_2O_6S_2$: C, 28.96; H, 6.25; N, 9.65. Found: C, 29.10; H, 6.38; N, 9.69.

EXAMPLE 13

Sulfamic acid 3-phenoxypropyl ester a. Sulfamoyl chloride solution was prepared as in Example 11 using: 31.5 ml (0.356 mole) of chlorosulfonyl isocyanate (98%), 6.3 ml (0.35 mole) of water and 150 ml of acetonitrile.

b. The title compound was obtained using the following procedure: The sulfamoyl chloride in acetonitrile solution prepared in (a) was reacted as in Example 11 with 15.6 g (0.102 mole) of 3-phenoxy-1-propanol using 40.2 g (0.398 mole) of triethylamine in 100 ml additional acetonitrile followed by using, extracting, washing and concentration procedures of Example 11 through the first evaporation. The residue was then purified by chromatography (4×90 cm glass column; 500 g silica gel; methylene chloride followed by 10:1 methylene chloride/acetone). Fractions containing the title compound were combined and the solvents were evaporated under reduced pressure to give 15.8 g of viscous oil which solidified on standing. The solid was recrystallized from ethyl acetate to give 14.7 g (62% yield) of title compound as white solid, mp 83°-85° C.

Analysis: Calculated for $C_9H_{13}NO_4S$: C, 46.74; H, 5.67; N, 6.06. Found: C, 46.80; H, 5.73; N, 6.05.

EXAMPLE 14

Sulfamic acid 2-chloro-2-phenylethyl ester

This compound was isolated during purification in the preparation of 2-phenylethanediol bissulfamate ester.

a. Sulfamoyl chloride solution was prepared as in Example 11 using: 62 ml (0.71 mole) of chlorosulfonyl isocyanate (98%), 12.4 g (0.69 mole) of water and 340 ml of acetonitrile.

b. The title compound was obtained as by-product using the following procedure: The sulfamoyl chloride in acetonitrile solution prepared in (a) was reacted as in Example 11 with 28.4 g (0.2 mole) of 2-phenylethanediol using 80.2 g (0.79 mole) of triethylamine in 200 ml of additional acetonitrile followed by using extracting, washing and concentration procedures of Example 11 through the first evaporation. The oil was purified by chromatography (4×90 cm glass column; 500 g silica gel; eluting agents: methylene chloride followed by 10:1 methylene chloride-acetone). Fractions containing the title compound were combined and the solvents were evaporated under reduced pressure to give 5.1 g of viscous oil. The oil was further purified by high pressure liquid chromatography using the Waters Associates Prep LC/System 500A with PrepPAK ® 500 silica. Eluting solvent was methylene chloride at a flow rate of 200 ml/min. Fractions containing the title compound were combined and the solvent was evaporated under reduced pressure to give 3.6 g (8%) of title compound as a colorless, viscous oil.

Analysis: Calculated for $C_8H_{10}ClNO_3S$: C, 40.77; H, 4.28; N, 5.94. Found: C, 40.59; H, 4.27; N, 5.96.

EXAMPLE 15

1,4:3,6-Dianhydro-d-mannitol disulfamate (ester)

a. Sulfamoyl chloride solution was prepared as in Example 11 using 42.6 g (0.30 mole) of chlorosulfonyl isocyanate, 5.4 ml (0.30 mole) of water and 60 ml of acetonitrile, 0°–10° C. during reaction.

b. The title compound was obtained using the following procedure: The sulfamoyl chloride prepared in (a) was reacted with 14.6 g (0.10 mole) of isomannide using 28.5 ml (0.352 mole) of pyridine in 40 ml of acetonitrile at 0°–5° C. followed by 2 hr at room temperature. Ethyl acetate, 60 ml, was added to the mixture which was then extracted with three 100 ml portions of saturated sodium chloride solution. These brine washes were combined and back extracted with ethyl acetate/acetonitrile mixture. The organic layers were combined, dried over magnesium sulfate, filtered and evaporated. The oily crystalline residue was recrystallized from acetonitrile and isopropyl alcohol (IPA) with removal of IPA on a rotary evaporator. Crystals were filtered, dried and analyzed.

Analysis: Calculated for $C_6H_{12}N_2O_8S_2$: C, 23.68; H, 3.98; N, 9.21. Found: C, 24.12; H, 4.09; N, 9.03.

EXAMPLE 16

Sulfamic acid 2-phenoxy-1,3-propanediyl ester a. Sulfamoyl chloride solution was prepared as in Example 11 using: 32 ml (0.368 mole) of chlorosulfonyl isocyanate (98%), 6.4 ml (0.356 mole) of water and 150 ml of acetonitrile.

b. The title compound was obtained using the following procedure: The sulfamoyl chloride prepared in (a) was reacted as in Example 11 with 17.3 g (0.103 mole) of 2-phenoxy-1,3-propanediol using 41.4 g (0.41 mole) of triethylamine in 100 ml of additional acetonitrile followed by using extracting, washing and concentration procedures of Example 11 through the first evaporation. The oily residue was purified by chromatography as in Example 13 and fractions containing the title compound were combined and concentrated to give a solid residue. The residue was recrystallized using ethyl ether and petroleum ether (bp 30°–60° C.) to give 7.5 g (22%) of white solid title compound, mp 104°–106° C.

Analysis: Calculated for $C_9H_{14}N_2O_7S_2$: C, 33.12; H, 4.32; N, 8.58. Found: C, 33.27; H, 4.36; N, 8.48.

EXAMPLE 17

Sulfamic acid (ethoxycarbonyl)phenylmethyl ester a. Preparation of sulfamoyl chloride solution in excess acetonitrile To 40 ml of acetonitrile cooled to −10° C. in an acetone/ice bath was added 26.2 ml (0.30 mole) of chlorosulfonyl isocyanate dropwise while maintaining temperature at −10° C. To this solution was added a solution of 5.4 ml (0.30 mole) of water in 20 ml of acetonitrile over a 30 min period maintaining temperature below 0° C.

b. Preparation of title compound

To the cold solution prepared in (a) was slowly added a solution of 36.04 g (0.20 mole) of ethyl dl-mandelate in 28.5 ml (0.352 mole) of pyridine and 20 ml of acetonitrile and the reaction mixture was allowed to warm slowly to room temperature. After stirring at room temperature overnight, the organic layer was extracted with three 100 ml portions of saturated sodium chloride solution and the aqueous layer was back extracted with 1:1 acetonitrile/ethyl acetate mixture. The organic layers were combined, dried over sodium sulfate and evaporated to give an oil residue. The oil was purified by column chromatography (10×80 cm glass column; 700 g silica gel; eluted with methylene chloride followed by 10:1 methylene chloride/acetone). Desired fractions were combined and concentrated. The solid residue was recrystallized from isopropyl alcohol and petroleum ether (30°–60° C. bp range) to yield 9.65 g (19%); mp 91°–93° C.

Analysis: Calculated for $C_{10}H_{13}NO_5S$: C, 46.33; H, 5.05; N, 5.40. Found: C, 46.25; H, 5.01; N, 5.36.

EXAMPLE 18

Dimethylsulfamic acid 2-[(2-methoxyphenoxy)methyl]-1,2-ethanediyl ester a. Preparation of dimethyl sulfamoyl chloride A mixture of 28.8 g (0.353 mole) of dimethylamine hydrochloride (98%, Aldrich Chemical Co.), 29.1 ml (0.362 mole) of sulfuryl chloride (97%, Aldrich) and 0.3 ml of antimony (V) pentachloride (Baker Chemical Co.) in 100 ml of acetonitrile was stirred and heated at reflux for 4 hr. An additional 29.1 ml (0.362 mole) of sulfuryl chloride was added and the mixture was heated at reflux overnight. The mixture was concentrated under reduced pressure to give 44.2 g (87%) of dimethyl sulfamoyl chloride as a brown liquid.

b. Preparation of title compound

To a stirred solution of 21.9 g (152.5 mole) of the dimethylsulfamoyl chloride prepared in (a) above in 60 ml of methylene chloride was added a solution of 7.6 g (0.038 mole) of 3-(2-methoxyphenoxy)-1,2-propanediol (glyceryl guaiacolate) and 12.1 g (0.152 mole) of pyridine in 40 ml of methylene chloride at such a rate that the reaction temperature was maintained at ≦12° C. The reaction mixture was stirred at ambient temperature for 4 days. Water, 200 ml, was added to the mixture and the layers were separated. The organic layer was washed successively with two 200 ml portions of 2N hydrochloric acid and 200 ml of water, dried over magnesium sulfate and the solvent was evaporated under reduced pressure to give 11.6 g of yellow liquid. The liquid was purified by high pressure chromatography using a Waters Associates Prep LC/System 500A with PrepPAK ® 500 silica. Eluting solvent used was 10:1 mixture of methylene chloride to ethyl acetate at a flow rate of 200 ml/min). Fractions containing the title compound were combined and the solvents were evaporated under reduced pressure to give 3.9 g (33%) of title compound as a yellow, viscous oil.

Analysis: Calculated for $C_{12}H_{19}NO_6S$: C, 47.20; H, 6.27; N, 4.59. Found: C, 47.73; H, 6.14; N, 4.30.

Analysis: Calculated for $C_{12}H_{19}NO_6S \cdot 0.05CH_3CO_2CH_2CH_3$: C, 47.31; H, 6.31; N, 4.56.

EXAMPLE 19

Sulfamic acid 2-[[(aminocarbonyl)oxy]-1-[(2-methoxyphenoxy)methyl]ethyl ester a. Sulfamoyl chloride solution was prepared as in Example 11 using: 30.4 ml (0.342 mole) of chlorosulfonyl isocyanate (98%), 6.4 g (0.356 mole) of water and 150 ml of acetonitrile.

b. The title compound was obtained using the following procedure: The sulfamoyl chloride in acetonitrile solution prepared in (a) was reacted as in Example 11 with 24.1 g (0.1 mole) of 3-(2-methoxyphenoxy)-1,2-propanediol-1-carbamate, which is methocarbamol, using 40.4 g (0.4 mole) of triethylamine in 100 ml additional acetonitrile followed by using extracting, washing and concentration procedures of Example 11 through the first evaporation. The viscous, oily residue 29.1 g was purified by chromatography using a 4.5 cm × 100 cm glass column filled with 550 g of silica gel and 10:1 ratio of methylene chloride/acetone as eluting agent. Fractions containing the title compound were combined and the solvents were evaporated under reduced pressure to give 12.6 g of a white solid. The solid was recrystallized from acetone-benzene to give 10.0 g (31%) of title compound as white solid, mp 119°-122° C.

Analysis: Calculated for $C_{11}H_{16}N_2O_7S$: C, 41.25; H, 5.04; N, 8.75. Found: C, 41.13; H, 5.07; N, 8.71.

EXAMPLE 20

Sulfamic acid 1,3-diphenoxy-2-propyl ester a. Sulfamoyl chloride solution was prepared as in Example 11 using: 18.8 ml (0.212 mole) of chlorosulfonyl isocyanate (98%), 3.9 g (0.217 mole) of water and 150 ml of acetonitrile.

b. The title compound was obtained using the following procedure: The sulfamoyl chloride prepared in (a) was reacted as in Example 11 with 15.0 g (0.061 mole) of 1,3-diphenoxy-2-propanol (Aldrich Chem. Co.) using 24.8 g (0.246 mole) of triethylamine in 100 ml of additional acetonitrile followed by using extracting, washing and concentration procedures through the first evaporation. The 20.4 g semisolid residue obtained was dissolved in 100 ml of methylene chloride and the solution was filtered through 50 g of silica gel. The silica gel was washed with 600 ml of methylene chloride. The combined methylene chloride solutions were evaporated under reduced pressure and the viscous residue was purified by high pressure liquid chromatography (Waters Associates Prep LC/System 500A; Prep-PAK ® 500 silica using methylene chloride eluting agent at a flow rate of 200 ml/min). Fractions containing the title compound were combined and solvents were evaporated under reduced pressure to give 12.9 g (65%) of title compound as white solid, mp 81°-84° C.

Analysis: Calculated for $C_{15}H_{17}NO_5S$: C, 55.72; H, 5.30; N, 4.33. Found: C, 55.58; H, 5.27; N, 4.28.

EXAMPLE 21

Sulfamic acid 1-[(4-chlorophenoxy)methyl]-1,2-ethanediyl ester a. Sulfamoyl chloride solution was prepared as in Example 11 using 50.5 ml (0.592 mole) of chlorosulfonyl isocyanate (98%), 10.9 g (0.606 mole) of water and 150 ml of acetonitrile.

b. The title compound was obtained using the following procedure: The sulfamoyl chloride in solution prepared in (a) was reacted as an Example 12 with 15.0 g (0.074 mole) of 3-(4-chlorophenoxy)-1,2-propanediol using 69.9 g (0.692 mole) of triethylamine in 100 ml of additional acetonitrile followed by using extracting, washing and concentration procedures of Example 11 through the first evaporation. The viscous, oily residue obtained was purified by high pressure liquid chromatography (Waters Associates Prep LC/System 500A; PrepPAK ® 500 silica; 9:1 methylene chloride-acetone at a flow rate of 200 ml/min). Fractions containing the title compound were combined and the solvents were evaporated under reduced pressure to give 10.2 g of viscous oil. The oil was partitioned between water and ethyl ether (300 ml each). The ether layer was separated and washed with three 200 ml portions of water, dried over sodium sulfate and solvent evaporated under reduced pressure to give 8.9 g (33%) of viscous oil which solidified on standing, mp 101°-104° C.

Analysis: Calculated for $C_9H_{13}ClN_2O_7S_2$: C, 29.96; H, 3.63; N, 7.76. Found: C, 30.36, H, 3.71; N, 7.75.

EXAMPLE 22

Sulfamic acid 2-(2-chlorophenoxy)ethyl ester a. Sulfamyl chloride solution was prepared as in Example 11 using 30.4 ml (0.342 mole) of chlorosulfonyl isocyanate (98%), 6.4 g (0.356 mole) of water and 150 ml of acetonitrile.

b. The title compound was obtained using the following procedure: The sulfamoyl chloride in solution prepared in (a) was reacted as in Example 11 with 17.3 g (0.100 mole) of 2-chlorophenoxyethanol using 40.4 g (0.400 mole) of triethylamine in 100 ml of acetonitrile followed by using the extracting, washing and concentration procedures of Example 11 through the first evaporation. The viscous, oily residue was partitioned between 500 ml of water and 500 ml of ethyl ether. The organic layer was washed with four 300 ml portions of water (pH of wash finally neutral to pH paper), dried over magnesium sulfate and the solvent evaporated under reduced pressure to give a white solid. The solid was recrystallized from ethyl ether-petroleum ether (bp range 30°-60° C.) to give 14.5 g (58%) of title compound as white solid, mp 84.5°-86° C.

Analysis: Calculated for $C_8H_{10}ClNO_4S$: C, 38.18; H, 4.01; N, 4.57. Found: C, 38.24; H, 4.03; N, 4.59.

EXAMPLE 23

Sulfamic acid 2-(4-chlorophenoxy)ethyl ester

The title compound was prepared by procedures of Example 22 from sulfamoyl chloride and 2-(4-chlorophenoxy)ethanol in 48% yield. A white solid, mp 117°–119° C. was obtained.

Analysis: Calculated for $C_8H_{10}ClNO_4S$: C, 38.18; H, 4.01; N, 5.57. Found: C, 38.38; H, 4.06; N, 5.66.

EXAMPLE 24

Sulfamic acid 2-(3-methylphenoxy)ethyl ester

The title compound was prepared by procedures of Example 22 from sulfamoyl chloride and 2-(3-methylphenoxy)ethanol in 47% yield (recrystallizing from the same solvent). A white solid, mp 76°–78° C., was obtained.

Analysis: Calculated for $C_9H_{13}NO_4S$: C, 46.74; H, 5.67; N, 6.06. Found: C, 46.79; H, 5.74; N, 6.13.

EXAMPLE 25

Sulfamic acid 3-phenoxy-2-propyl ester

The title compound was prepared by procedures of Example 22 from sulfamoyl chloride and 3-phenoxy-2-propanol through the partitioning and final evaporation to give an oil as residue. The oil was purified by chromatography using a 4.5 cm × 100 cm glass column packed with 500 g of silica gel and methylene chloride as eluting agent. Fractions containing the title compound were combined and the solvent was evaporated under reduced pressure to give a 37% yield of an oil which solidified on standing, mp 57°–60° C.

Analysis: Calculated for $C_9H_{13}NO_4S$: C, 46.74; H, 5.67; N, 6.06. Found: C, 46.85; H, 5.73; N, 6.02.

EXAMPLE 26

Sulfamic acid 2-(2-pyridinyl)ethyl ester a. Sulfamoyl chloride solution was prepared as in Example 11 using 43 ml (0.484 mole) of chlorosulfonyl isocyanate (98%), 8.6 g (0.478 mole) of water and 150 ml of methylene chloride.

b. The title compound was obtained using the following procedure: The sulfamoyl chloride solution prepared in (a) was reacted as in Example 11 with 16.7 g (0.136 mole) of 2-($\beta$-hydroxyethyl)pyridine using 54.9 g (0.544 mole) of triethylamine in 100 ml of methylene chloride. Water, 150 ml, was added to the reaction mixture with agitation and the layers were separated. The organic layer was discarded, pH of the aqueous layer was adjusted to 8 with sodium carbonate. The mixture was extracted with three 200 ml portions of methylene chloride. The organic extracts were washed twice with 200 ml portions of water, dried over magnesium sulfate and the solvent was evaporated under reduced pressure to give 7.1 g of a brown, viscous oil which solidified on standing. The solid was recrystallized from methylene chloride-petroleum ether (bp range 30°–60° C.) to give 3.2 g (12%) of title compound as white needles, mp 89°–91° C.

Analysis: Calculated for $C_7H_{10}N_2O_3S$: C, 41.58; H, 4.98; N, 13.85. Found: C, 41.30; H, 5.00; N, 13.75.

EXAMPLE 27

Sulfamic acid 2-(3-methoxyphenoxy)ethyl ester

The title compound was prepared by procedures of Example 11 from sulfamoyl chloride and 2-(3-methoxyphenoxy)ethanol through the first evaporation step to give a brown, viscous, oily residue. The oil was dissolved in 300 ml of ethyl ether. The organic solution was washed with two 300 ml portions of water, dried over magnesium sulfate and the solvent evaporated under reduced pressure to give a viscous, oily residue for the second time. The oil was purified by chromatography using silica gel and methylene chloride-acetone in 90:1 ratio as eluting agent. Fractions containing the title compound were combined and solvents evaporated under reduced pressure to give a viscous oil which solidified on standing. The solid was recrystallized from ethyl-petroleum ether (bp range 30°–60° C.) to give the title compound as white solid, mp 78°–82° C., in 46% yield.

Analysis: Calculated for $C_9H_{13}NO_5$: C, 43.72; H, 5.30; N, 5.66. Found: C, 43.77; H, 5.33; N, 5.67.

EXAMPLE 28

Sulfamic acid 2-(4-methylphenoxy)ethyl ester a. Sulfamoyl chloride solution was prepared as in Example 11 using 40 ml (0.450 mole) of chlorosulfonyl isocyanate, 8.0 g (0.444 mole) of water and 150 ml of acetonitrile.

b. The title compound was obtained using the following procedure: The sulfamoyl chloride in acetonitrile solution prepared in (a), 17.0 g (0.112 mole) of 4-methylphenoxyethanol, 51.0 g (0.505 mole) of triethylamine in 100 ml of acetonitrile were reacted as in Example 12 followed by using extracting, washing and concentration procedures of that example through the first evaporation step. The viscous oil obtained was partitioned between water and ethyl ether (400 ml each). The layers were separated and the organic layer was washed with four 300 ml portions of water (pH neutral to pH paper), dried over magnesium sulfate and the solvent was evaporated under reduced pressure to give a solid residue. The solid was recrystallized from ethyl ether-petroleum ether (bp range 30°–60° C.) to give 15.6 g (60%) of title compound as an off-white solid, m.p. 108.5°–110° C.

Anaylsis: Calculated for $C_9H_{13}NO_4S$: C, 46.74; H, 5.67; N, 6.06. Found: C, 47.06; H, 5.76; N, 6.12.

EXAMPLE 29

Sulfamic acid 2-(2-methylphenoxy)ethyl ester

The title compound was prepared by procedures of Example 28 from sulfamoyl chloride and 2-(2-methylphenoxy)ethanol in 53% yield as an off-white solid, mp 81.5°–83° C.

Analysis: Calculated for $C_9H_{13}NO_4S$: C, 46.74; H, 5.67; N, 6.06. Found: C, 46.91; H, 5.75; N, 6.32.

EXAMPLE 30

Sulfamic acid 3-phenoxybutyl ester

The title compound was prepared by procedures of Example 28 from sulfamoyl chloride and 4-phenoxy-1-butanol in 54% yield as an off-white solid, mp 76°–77° C.

Analysis: Calculated for $C_{10}H_{15}NO_4S$: C, 48.97; H, 6.16; N, 5.71. Found: C, 49.08; H, 6.26; N, 5.79.

EXAMPLE 31

Sulfamic acid 2-(4-methoxyphenoxy)ethyl ester

The title compound was prepared by procedures of Example 28 from sulfamoyl chloride and 2-(4-methoxyphenoxy)ethanol in 54% yield as an off-white solid, mp 84°–87° C.

Analysis: Calculated for $C_9H_{13}NO_5S$: C, 43.72; H, 5.30; N, 5.66. Found: C, 44.20; H, 5.38; N, 5.70.

EXAMPLE 32

Sulfamic acid 2-(benzyloxy)ethyl ester

The title compound was prepared by procedures of Example 33 from sulfamoyl chloride and 2-(benzyloxy)ethanol except the oil obtained was then further purified by high pressure chromatography as described in earlier examples using methylene chloride as eluting agent. Fractions containing the title compound were combined and the solvent was evaporated under reduced pressure to give title compound in 54% yield as light-yellow, viscous oil.

Analysis: Calculated for $C_9H_{13}NO_4S$: C, 46.74; H, 5.67; N, 6.06. Found: C, 46.48; H, 5.74; N, 6.03.

EXAMPLE 33

Sulfamic acid phenyl ester

The compound was prepared by procedures of Example 28 from sulfamoyl chloride and phenol in 30% yield as white solid, mp 81°–85° C.

Analysis: Calculated for $C_6H_7NO_3S$: C, 41.61; H, 4.07; N, 8.09. Found: C, 41.63; H, 4.09; N, 8.07.

EXAMPLE 34

Sulfamic acid 2-(6-methoxy-2-naphthyl)propyl ester

The title compound was prepared by the procedure of Example 28 from sulfamoyl chloride and 2-(6-methoxy-2-naphthyl)propanol as white solid, mp 112°–115° C., in 21% yield.

Analysis: Calculated for $C_{14}H_{17}NO_4S$: C, 56.93; H, 5.80; N, 4.74. Found: C, 56.98; H, 5.88; N, 4.85.

EXAMPLE 35

Sulfamic acid 2-(2-methoxyphenoxy)ethyl ester

The title compound was prepared by the procedure of Example 28 from sulfamoyl chloride and 2-(2-methoxyphenoxy)ethanol. The solid obtained was dissolved in 150 ml of methylene chloride, and the solution was treated with charcoal and filtered through Celite ®. The filtrate was evaporated under reduced pressure and the solid residue was recrystallized from methylene chloride-petroleum ether (bp range 30°–60° C.) to give the title compound in 25% yield as white solid, mp 102°–104° C.

Analysis: Calculated for $C_9H_{13}NO_5S$: C, 43.72; H, 5.30; N, 5.66. Found: C, 43.72; H, 5.34; N, 5.63.

EXAMPLE 36

Sulfamic acid 2-phenoxypropyl ester

The title compound was prepared by procedures of Example 28 from sulfamoyl chloride and 2-phenoxypropanol. The oil obtained was further purified as in Example 28 by chromatography and recrystallization to give the title compound as colorless, viscous oil in 35% yield.

Analysis: Calculated for $C_{19}H_{13}NO_4S$: C, 46.74; H, 5.67; N, 6.06. Found: C, 46.70; H, 5.73; N, 6.02.

EXAMPLE 37

Sulfamic acid 2-(4-chlorophenoxy)-2-methylpropyl ester

The title compound was prepared by procedures of Example 28 from sulfamoyl chloride and 2-(4-chlorophenoxy)-2-methylpropanol to give white solid, mp 76°–79° C., in 58% yield.

Analysis: Calculated for $C_{10}H_{14}ClNO_4S$: C, 42.94; H, 5.04; N, 5.01. Found: C, 42.99; H, 5.13; N, 5.12.

EXAMPLE 38

Sulfamic acid 2-(3-chlorophenoxy)ethyl ester

The title compound was prepared by procedures of Example 28 from sulfamoyl chloride and 2-(3-chlorophenoxy)ethanol. The oil obtained was further purified by chromatography and recrystallization as in Example 38 to give white solid, mp 66°–69° C., in 44% yield.

Analysis: Calculated for $C_8H_{10}ClNO_4S$: C, 38.18; H, 4.01; N, 5.57. Found: C, 38.25; H, 4.03; N, 5.61.

EXAMPLE 39

Sulfamic acid 2-(4-bromophenoxy)ethyl ester

The title compound was prepared by the procedures of Example 28 from sulfamoyl chloride and 2-(4-bromophenoxy)ethanol as white solid, mp 134°–137° C., in 69% yield.

Analysis: Calculated for $C_8H_{10}BrNO_4S$: C, 32.45; H, 3.40; N, 4.73. Found: C, 32.71; H, 3.47; N, 4.71.

EXAMPLE 40

Sulfamic acid 2-(2,4-dichlorophenoxy)ethyl ester

The title compound was prepared by the procedures of Example 28 from sulfamoyl chloride and 2-(2,4-dichlorophenoxy)ethanol. The viscous oil obtained solidified and was recrystallized from isopropyl ether to give the solid title compound, mp 75°–77° C., in 35% yield.

An additional 6.9 g of title compound was recovered from the mother liquor to bring the total yield to 60%.

Analysis: Calculated for $C_8H_9Cl_2NO_4S$: C, 33.58; H, 3.17; N, 4.90. Found: C, 33.65; H, 3.16; N, 5.00.

EXAMPLE 41

Sulfamic acid 2-(3,4-dichlorophenoxy)ethyl ester

The title compound was prepared by the procedures of Example 4228 from sulfamoyl chloride and to 2-(3,4-dichlorophenoxy)ethanol. The tan colored solid obtained was dissolved in isopropyl ether and the solution treated with charcoal and filtered through Celite ®. The filtrate was evaporated under reduced pressure and the solid residue was recrystallized from isopropyl ether to give the title compound, mp 84°–85° C., in 19% yield.

Analysis: Calculated for $C_8H_9Cl_2NO_4S$: C, 33.58; H, 3.17; N, 4.90. Found: C, 33.76; H, 3.19; N, 4.92.

EXAMPLE 42

Sulfamic acid phenyl ester a. Preparation of benzyloxycarbonylsulfamoyl chloride The procedure of Example 6 was followed scaling the reaction to 0.2 moles each of benzyl alcohol and chlorosulfonyl isocyanate to give benzyloxycarbonylsulfamoyl chloride.

b. Preparation of 2-(benzyloxycarbonylaminosulfonyloxy)benzoic acid benzyl ester sodium salt To the solution prepared in (a) containing approximately 0.2 mole of benzyloxycarbonylsulfamoyl chloride was added a solution of 22.8 g (0.1 mole) of benzylsalicylate, 16 ml (0.2 mole) of pyridine and 0.5 g of dimethylaminopyridine in 70 ml of methylene chloride at about 10° C. over a 10 min period. The reaction mixture was stirred overnight at room temperature and then extracted once with dilute hydrochloric acid followed by water. Both aqueous layers were back extracted with methylene chloride. The combined organic layers were dried and evaporated to give an oil. The oil was dissolved in a small amount of tetrahydrofuran (THF) and filtered to remove some insoluble solid. The THF filtrate was added to about 300 ml of saturated sodium bicarbonate solution and the resulting suspension was stirred over-night. The solid was collected by filtration, rinsed twice with water and twice with isopropyl alcohol-isopropyl ether and dried by pulling air through the filter to a weight of 25.88 g (56% yield of sodium salt). A second crop of 5.60 g (12%) was also obtained.

c. Preparation of title compound

The 2-(benzyloxycarbonylaminosulfonyloxy)benzoic acid benzyl ester sodium salt prepared above, [35.3 g (0.076 mole)] was suspended in 500 ml of methanol was mixed with 6.2 ml of concentrated hydrochloric acid and 2 g of 5% palladium on carbon wetted with 50 ml methanol. The mixture was hydrogenated with hydrogen gas for 4 hr and filtered. The filtrate was concentrated to an oil. The oil was suspended in THF and filtered to remove some solids. The clear filtrate was concentrated and mixed with 1,1,1-trichloroethanol to precipitate the product as 8.82 g of light purple solid obtained after filtration. The purple solid was dissolved in THF and the solution was treated with charcoal, filtered and concentrated. The solid was recrystallized from 1,1,1-trichloroethane to give 6.5 g of white solid (39%), mp 139°-140° C.

Analysis: Calculated for $C_7H_7NO_5S$: C, 38.71; H, 3.25; N, 6.45. Found: C, 38.16; H, 3.24; N, 6.55.

EXAMPLE 43

Methylsulfamic acid 1-chloro-3-(2-methoxyphenoxy)-2-propyl ester

A solution of 109.3 g (0.55 mole) of glyceryl guaiacolate in 177 ml (2.20 moles) of pyridine and 700 ml methylene chloride was added to a solution of 283 g (2.20 moles) of methylaminosulfonyl chloride in 700 ml of methylene chloride. The addition was made over one hour at 15°-22° C. The solution was stirred at 23° C. for two hours then washed with 3×500 ml water. The methylene chloride solution was dried over type 3A molecular sieves. The mixture was filtered and the filtrate diluted with 140 ml of ethyl acetate. The solution was chromatographed on 2 kg of silica gel using 10% ethyl acetate:methylene chloride solution as eluent. The first 3×750 ml fractions were combined and concentrated to 77.3 g of brown oil. The oil was redissolved in 400 ml of 10% ethyl acetate:methylene chloride solution and chromatographed on 1.5 kg of silica gel. A total of 9×250 ml fractions were collected that showed only one spot on TLC.

The fractions were combined and concentrated to 20.6 g of oil which crystallized on standing.

The 20.6 g was recrystallized from 20 ml of isopropyl alcohol to give 6.9 g of white solid, mp 84°-85° C. The compound was characterized by $^1H$ NMR, $^{13}C$ NMR and C-I mass spec.

Analysis: Calculated for $C_{11}H_{16}ClNO_5S$: C, 42.65; H, 5.21; N, 4.52. Found: C, 42.32; H, 5.25; N, 4.61.

EXAMPLE 44

Methylsulfamic acid 2-(4-chlorophenoxy)ethyl ester

A mixture of 32.4 g (0.57 mole) of methylamine hydrochloride (98%, Aldrich), 39 ml (0.47 mole) of sulfuryl chloride (97%, Aldrich), and 0.4 ml of antimony (V) pentachloride (Baker) in 150 ml of acetonitrile was heated at reflux for 4 hr. To the reaction mixture was added an additional 39 ml (0.47 mole) of sulfuryl chloride (97%, Aldrich) and heating at reflux was continued overnight. The solvent was evaporated under reduced pressure to give 57.4 g (94%) of methyl sulfamoyl chloride as a light-brown oil.

To a stirred solution of 45.0 g (0.347 mole) of methylsulfamoyl chloride prepared above in 100 ml of methylene chloride was added in a thin stream a solution of 25.0 g (0.145 mole) of 2-(4-chlorophenoxy)ethanol (Lancaster Synthesis, Inc., Windham, N.H. 03087) in 30 ml (0.369 mole) of pyridine and 100 ml of methylene chloride and the reaction mixture was stirred at ambient temperature for 3 days. The solids were removed by filtration and the filtrate was evaporated under reduced pressure to yield a brown viscous residue. The residue was partitioned between water and ethyl ether (400 ml each). The organic layer was washed twice with 300 ml portions of water, dried over magnesium sulfate and the solvent evaporated under reduced pressure to yield a solid residue. The solid was triturated with 100 ml of isopropyl ether and the solid was recollected by filtration. The solid was recrystallized from isopropyl ether to give 12.9 g (34%) of title compound as a white solid, m.p. 101°-104° C.

Analysis: Calculated for $C_9H_{12}ClNO_4S$: C, 40.68; H, 4.55; N, 5.27. Found: C, 40.78; H, 4.62; N, 5.25.

EXAMPLE 45

Sulfamic acid 3-phenoxy-1-butyl ester

The title compound was prepared by procedures of Example 28 from sulfamoyl chloride and 3-phenoxy-1-butanol. The viscous oil obtained was purified by high pressure chromatography using a Waters Associates Prep LC/System 500A; PrepPAK ® 500 silica and methylene chloride as eluting agent at a flow rate of 200 ml/min. Fractions containing the title compound were combined and the solvent was evaporated under reduced pressure to give 12.7 g (67%) of title compound as yellow, viscous oil.

Analysis: Calculated for $C_{10}H_{15}NO_4S$: C, 48.97; H, 6.16; N, 5.71. Found: C, 47.70; H, 6.22; N, 5.52.

Analysis: Calculated for $C_{10}H_{15}NO_4S.0.1CH_2CH_2$: C, 47.80; H, 6.04; N, 5.52.

EXAMPLE 46

Dimethylsulfamic acid 2-(4-chlorophenoxy)ethyl ester

A solution of 25.0 g (0.145 mole) of 2-(4-chlorophenoxy)ethanol (Lancaster Synthesis Inc., Windham, N.H. 03087) in 64.6 g (0.640 mole) of triethylamine and 40 ml of methylene chloride was added in a thin stream to a solution of 83.3 g (0.580 mole) of dimethylsulfamoyl chloride (Aldrich) in 60 ml of methylene chloride stirred at ambient temperature in a water bath. The reaction mixture was stirred for 8 days at ambient temperature. The solids were removed by filtration and the filtrate was evaporated under reduced pressure to yield a viscous residue. The residue was partitioned between water and ethyl ether (300 ml each). The organic layer was washed with two 200 ml portions of 2N hydrochloric acid. Once with 200 ml of water, dried over magnesium sulfate and the solvent evaporated under reduced pressure to yield a viscous residue. The residue was treated with 65.0 g (0.63 mole) of triethylamine and the reaction mixture was stirred for 5 days at ambient temperature. The solids were removed by filtration and the filtrate was evaporated under reduced pressure and the viscous residue was partitioned between water and ethyl ether (450 ml each). The organic layer was washed with four 300 ml portions of water (pH neutral to pH paper), dried over magnesium sulfate and the solvent evaporated under reduced pressure to yield a brown viscous oily residue. The oil was purified by chromatography (4.5×90 cm glass column; 500 g of silica gel; methylene chloride). Fractions containing the title compound were combined and the solvent evaporated under reduced pressure to yield a viscous oil. The oil was dissolved in 150 ml of isopropyl ether and filtered to remove some insolubles. The filtrate was concentrated to a viscous oil. The oil was triturated with isopropyl ether-petroleum ether (bp range 30°-60° C.), cooled (refrigerator) and the resulting solid was collected by filtration. The solid was recrystallized from isopropyl ether to give 18.5 g (45%) of white solid, mp 54°-57° C.

Analysis: Calculated for $C_{10}H_{14}ClNO_4S$: C, 42.94; H, 5.04; N, 5.01. Found: C, 43.20; H, 5.11; N, 4.94.

EXAMPLE 47

Sulfamic acid 2-methyl-2-phenoxypropyl ester

This compound was prepared by the procedure used to synthesize 2-(4-methylphenoxy)ethanol sulfamate in Example 28. Thus, 13.2 g (0.0794 mole) of 2-methyl-2-phenoxypropanol was reacted with sulfamoyl chloride prepared from 26.5 ml (0.298 mole) of chlorosulfonyl isocyanate (98%, Aldrich), 33.9 g (0.336 mole) of triethylamine, and 5.3 g (0.294 mole) of water in 250 ml of acetonitrile. The 12.4 g of a viscous, oily residue obtained was purified by high pressure liquid chromatography (Waters Associates Prep LC/System 500A; Pre-PAK 500 ® silica; methylene chloride), then by chromatography (4.5×90 cm glass column; 500 g of silica gel; methylene chloride). Fractions containing title compound were combined and the solvent was evaporated under reduced pressure to give 5.4 g (28%) of a viscous oil.

Analysis: Calculated for $C_{10}H_{15}NO_4S$: C, 48.97; H, 6.16; N, 5.71. Found: C, 48.11; H, 6.18; N, 5.58.

EXAMPLE 48

Dimethylsulfamic acid 1-[(2-methoxyphenoxy)methyl]-1,2-propanediyl ester

A mixture of 19.8 g (0.1 mole) of glyceryl guaiacolate, 114.9 g (0.8 mole) of dimethylsulfamoyl chloride (Aldrich) and 89.2 g (0.88 mole) of triethylamine was stirred at ambient temperature for 5 days. To this mixture was added an additional 58 g (0.4 mole) of dimethylsulfamoyl chloride (Aldrich) and 45 g (0.45 mole) of triethylamine and the mixture was stirred at ambient temperature for 2 days, treated with water and ethyl acetate (400 ml each). The layers were separated and the organic layer was washed with six 300 ml portions of water, dried over magnesium sulfate and the solvent evaporated under reduced pressure to yield a viscous oil. The oil was purified by chromatography (4.5×90 cm glass column; 500 g of silica gel; methylene chloride). Fractions containing title compound were combined and the solvent was evaporated under reduced pressure to give 10.3 g (25%) of an oil that solidified upon standing. The solid was recrystallized from methylene chloride-ethyl ether to give 9.6 g (23%) of white solid, mp 78°-81° C.

Analysis: Calculated for $C_{14}H_{24}N_2O_8S_2$: C, 40.77; H, 5.87; N, 6.79. Found: C, 40.75; H, 5.98; N, 5.58.

EXAMPLE 49

Sulfamic acid 4-chlorophenyl ester

In one portion, 96 g (0.75 mole) of 4-chlorophenol was added to a stirred solution of 67.5 ml (0.75 mole) of chlorosulfonylisocyanate in 400 ml of toluene. The solution was heated at 100° C. for 16 hr and the solution chilled with an ice-acetone bath and water added dropwise until evolution of carbon dioxide ceased. The tan solid which precipitated from solution was collected and dried for 16 hr to yield 133.4 g. A 25 g portion was recrystallized from 100 ml of toluene to give 15.8 g of white solid, mp 103°-104° C.

Analysis: Calculated for $C_6H_5ClNO_3S$: C, 34.71; H, 2.91; N, 6.75. Found: C, 34.73; H, 2.92; N, 6.74.

EXAMPLE 50

Sulfamic acid 3-chlorophenyl ester

By the procedure of Example 58, 96 g (0.75 mole) of 3-chlorophenol and 67.5 ml (0.75 mole) of chlorosulfonyl isocyanate gave 122.9 g of solid product. A 25 g portion was recrystallized from 100 ml of toluene to give 11.8 g of white solid, mp 82°-83° C.

Analysis: Calculated for $C_6H_6ClNO_3S$: C, 34.71; H, 2.91; N, 6.75. Found: C, 34.69; H, 2.90; N, 6.74.

EXAMPLE 51

Methylsulfamic acid 1-(aminosulfonyloxy)-3-(2-methoxyphenoxy)-2-propyl ester

A mixture of 8.0 g (0.0288 mole) of 3-(2-methoxyphenoxy)-2-hydroxypropanol sulfamate ester, 9.3 g (0.0721 mole) of methylsulfamoyl chloride and 7.3 g (0.0723 mole) of triethylamine was stirred at ambient temperature for 72 hr, treated with methylene chloride and water (150 ml each), and stirred vigorously for 10 min. The layers were separated and the organic layer was washed with four 150 ml portions of water, dried (over magnesium sulfate) and the solvent was evaporated under reduced pressure to yield a brown, viscous oil. The oil was purified by high pressure liquid chromatography (Waters Associates Prep LC 500A System; PrepPAK ® 500 silica; methylene chloride-acetone; 9:1; flow rate: 100 ml/min). Fractions containing the title compound were combined and the solvents were evaporated under reduced pressure to give 2.2 g of a dark, viscous oil. The oil was dissolved in 100 ml of methylene chloride, treated with charcoal and filtered. The filtrate was evaporated under reduced pressure to give 2.1 g (20%) of title compound as a yellow gum.

Analysis: Calculated for $C_{11}H_{18}N_2O_8S_2$: C, 35.67; H, 4.90; N, 7.56. Found: C, 34.04; H, 4.95; N, 7.32.

EXAMPLE 52

Methylsulfamic acid phenyl ester

The reaction flask was charged with 34.1 g (0.20 mole) of methylaminosulfonyl chloride, 18.8 g (0.20 mole) of phenol and 150 ml of toluene. The dark, red solution was heated at 110° C. for 16 hours. The solution was cooled and washed with a solution of 16 g of sodium bicarbonate in 80 ml water. The toluene solution was washed with water then stirred with Type 3A molecular sieve powder and Norite "A" activated charcoal. After filtration, the filtrate was concentrated to 32.7 g of oil (87% crude yield). The oil was dissolved in 100 ml methylene chloride and chromatographed on silica gel. The main fraction was concentrated to an oil which solidified after chilling for 3 days. The solid was triturated with petroleum ether to give 16.1 g of solid, mp 43°–45° C. A recrystallization from a mixture of isopropyl acetate (2 ml/g) and petroleum ether (4 ml/g) gave 12.3 g of solid, mp 44°–46° C.

Analysis: Calculated for $C_7H_9NO_3S$: C, 44.91; H, 4.85; N, 7.48. Found: C, 44.84; H, 4.87; N, 7.47.

EXAMPLE 53

Sulfamic acid 4-oxo-4-phenylbutyl ester

A cold (−10° C.) solution of 5.20 ml (0.06 mole) chlorosulfonyl isocyanate in 50 ml of methylene chloride was treated with a solution of 0.11 ml of water in 5 ml of acetonitrile over a period of 30 min. A solution of 6.56 g (0.04 mole) of 4-oxo-4-phenylbutanol and 8.34 ml (0.06 mole) of triethylamine in 30 ml of methylene chloride was then added to the solution of the sulfamoyl chloride at 0° to 10° C. over 20 min. The reaction mixture was stirred at room temperature for 4 hr. extracted once with water and once with sodium bicarbonate solution. The aqueous layers were back extracted with methylene chloride. The combined organic layers were dried (magnesium sulfate) and concentrated to an oil that solidified on standing. The solid was triturated with 1,1,1-trichloroethane to give 3.90 g of off-white solid. Recrystallization from acetonitrile-1,1,1-trichloroethane yielded 3.2 g of off-white solid, mp 78°–80° C.

Analysis: Calculated for $C_{10}H_{13}NO_4S$: C, 49.37; H, 5.30; N, 5/76. Found: C, 48.90; H, 5.48; N, 5.81.

EXAMPLE 54

Sulfamic acid 2-(2-oxo-1-pyrrolidinyl)ethyl ester

A solution of 6.5 g (0.05 mole) of 1-(2-hydroxyethyl)-2-pyrrolidone (Fluka) in 100 ml of methylene chloride was treated with 5.8 (0.05 mole) of sulfamoyl chloride. The solution was stirred for 2 hr, then concentrated under vacuum. The residue was crystallized twice from 2-propanol to give 6.9 g (66%) of the title compound as white crystals, mp 110°–112° C. The compound was noted to be slightly hygroscopic.

Analysis: Calculated for $C_6H_{12}N_2O_4S$: C, 34.61; H, 5.81; N, 13.45. Found: C, 34.16; H, 5.97; N, 13.14.

EXAMPLE 55

Sulfamic acid 2,3-dihydro-1H-indole-1-propyl ester

Using the procedure in Example 53, 5.3 g (0.03 mole) of 1-(3-hydroxypropyl) indoline (Preparation 15) was used to prepare the title compound. The crude product, a brown oil weighing 6.2 g, was dissolved in isopropyl alcohol and the solution chilled and acidified with 37% hydrochloric acid solution. The off-white solid that formed was collected and rinsed with a mixture of isopropyl alcohol-isopropyl ether. The solid (5.3 g) was recrystallized by dissolving in 100 ml of methanol at 40° C., addition of isopropyl alcohol, and removal of most of the methanol by careful evaporation. The solid product was collected, rinsed with a mixture of isopropyl alcohol-isopropyl ether, and dried in vacuo at 50° C. for 18 hr to give 4.8 g (55%) of white solid monohydrochloride, mp 134°–135° C.

Analysis: Calculated for $C_{11}H_{16}N_2O_3S \cdot HCl$: C, 45.13; H, 5.85; N, 9.57. Found: C, 44.86; H, 5.95; N, 9.44.

EXAMPLE 56

Sulfamic acid 4-(acetylamino)phenyl ester

A reaction flask was charged with 43.8 g (0.252 mole) of sulfamic acid, phenyl ester; 12.6 g (0.084 mole) of 4-acetamidophenol, 9 ml of pyridine and 150 ml p-dioxane. The solution was heated at 75° C. for 18 hours. The solution was concentrated to a brown oil. The oil was portioned between 100 ml methylene chloride and 100 ml of 1.0N sodium bicarbonate. The mixture was refrigerated overnight then filtered to collect 15.8 g of white solid. $^1H$ NMR spectrum indicated pure product but contaminated with sodium bicarbonate. The solid was added to 100 ml $H_2O$ and the mixture stirred for one hour. The solid was collected and dried to give 8.4 g of solid, mp 180°–181° C.

Analysis: Calculated for $C_8H_{10}N_2O_4S$: C, 41.73; H, 4.38; N, 12.17. Found: C, 41.72; H, 4.42; N, 11.99.

EXAMPLE 57

Sulfamic acid (1H-indol-1-yl)propyl ester

Using the procedure of Example 53, 5.25 g (0.03 mole) of 1-(3-hydroxypropyl)indole (Preparation 16) was used to prepare the title compound. The crude product, 4.7 g, was purified by preparative high pressure liquid chromatography to yield 1.95 g of solid after removal of solvents, mp 65°–66° C.

Analysis: Calculated for $C_{11}H_{14}N_2O_3S$: C, 51.95; H, 5.55; N, 11.02. Found: C, 51.92; H, 5.62; N, 10.98.

EXAMPLE 58

Methylsulfamic acid 2-hydroxy-3-(2-methoxyphenoxy)propyl ester

A solution of 26.5 g (0.13 mole) of glycerol guaiacolate in 100 ml of methylene chloride and 10.8 ml (0.13 mole) of pyridine was added in a thin stream to a stirred solution of 17.1 g (0.13 mole) of N-methylsulfamoyl chloride (Preparation 22) in 70 ml of methylene chloride, and the reaction mixture was stirred at ambient temperature for 2 hr. The reaction mixture was treated with 150 ml of water, the layers were separated, and the organic layer was washed successively with a 200 ml portion of 2N hydrochloric acid solution, four 200 ml portions of water, dried (magnesium sulfate), and the solvent was evaporated under reduced pressure to yield a viscous oil. The oil was purified by preparative high pressure liquid chromatography. Fractions containing the desired product were combined and the solvents evaporated under reduced pressure to give 13.9 g (37%) of the title compound as a yellow gum.

Analysis: Calculated for $C_{11}H_{17}NO_6S$: C, 45.35; H, 5.88; N, 4.81. Found: C, 44.99; H, 5.95; N, 4.78.

EXAMPLE 59

Sulfamic acid 2-hydroxy-3-(2-methoxyphenoxy)propyl ester

To a cold solution (5° C.) of 19.2 ml (0.22 mole) of chlorosulfonyl isocyanate in 180 ml of acetonitrile was added 23.8 g (0.22 mole) of benzyl alcohol (reaction mixture temperature, 5°-8° C.). To this reaction mixture was added a solution of 39.6 g (0.2 mole) of glyceryl guaiacolate and 23.2 g (0.23 mole) of triethylamine in 180 ml of acetonitrile (reaction temperature, 5°-12° C.). The reaction mixture was stirred for 3 hr, and the solids were removed by filtration. The filtrate was stirred with 1.5 g of 5% Pd-C for 1 hr, filtered, and the filtrate was divided into two equal fractions. Each fraction was stirred with 1.5 g of 5% Pd-C and hydrogenated. The catalyst was removed by filtration, and the filtrates were concentrated under reduced pressure to give 45 g and 42.3 g respectively. $^{13}$C NMR showed the fractions to be identical. The two fractions were combined and were purified by chromatography (4.5×90 cm glass column; 550 g of silica gel; methylene chloride-acetone, 5:1). Fractions containing the desired component were combined and the solvents evaporated under reduced pressure to give 13.8 g of a viscous oil. The oil was triturated with methylene chloride and insolubles were removed by filtration. The filtrate was evaporated under reduced pressure to give 12.9 g of a viscous oil. A 4.0 g sample of this oil was purified by high pressure liquid chromatography (Waters Associates Prep LC/System 500A; PrepPAK ® 500 silica; methylene chloride-acetone, 10:1; flow rate 200 ml/min). Fractions containing the desired component were combined, and the solvents evaporated under reduced pressure to give 2.3 g (58% recovery) of the title compound as a brown gum containing a trace of methylene chloride.

Analysis: Calculated for $C_{10}H_{15}NO_6S$: C, 43.32; H, 5.45; N, 5.05. Found: C, 42.60; H, 5.48; N, 4.96.

Analysis: Calculated for $C_{10}H_{15}NO_6S \cdot 0.04CH_2Cl_2$: C, 42.96; H, 5.42; N, 4.99.

EXAMPLE 60

Methylsulfamic acid 2-[(aminosulfonyl)oxy]-3-(2-methoxyphenoxy)propyl ester

To a cold solution (ice-acetone bath) of 14.7 ml (0.166 mole) of chlorosulfonyl isocyanate (98%; Aldrich) in 100 ml of acetonitrile was added dropwise a solution of 2.7 g (0.15 mole) of water in 5 ml of acetonitrile such that the reaction mixture temperature was maintained at ≦7° C. The mixture was stirred vigorously for 10 min, and to it was added a solution of 12.3 g (0.042 mole) of 3-(2-methoxyphenoxy)-1,2-propanediol methyl sulfamate ester (Example 59) and 17.0 g (0.168 mol) of triethylamine in 100 ml of acetonitrile at such a rate that the temperature of the reaction mixture was maintained at ≦12° C. The reaction mixture was stirred vigorously for 3 hr at ambient temperature and treated with 100 ml of water and 200 ml of ethyl acetate. The layers were separated, and the organic layer was washed with 200 ml of water and evaporated under reduced pressure to yield a viscous residue. The residue was partitioned between 200 ml of water and 300 ml of ethyl ether. The organic layer was washed with three 200 ml portions of water (pH neutral to pH paper), dried over magnesium sulfate and the solvent evaporated under reduced pressure to give 8.5 g (55%) of a viscous, oily residue which solidified upon standing. The solid was triturated with 75 ml of methylene chloride, and the precipitate was collected by filtration to yield 4.2 g (27%) of the title compound as a white solid, mp 110°-113° C.

Analysis: Calculated for $C_{11}H_{18}N_2O_8S_2$: C, 35.67; H, 4.90; N, 7.56. Found: C, 35.54; H, 4.96; N, 7.54.

EXAMPLE 61

Sulfamic acid 2-(8-quinolinyloxy)ethyl ester

Using the procedure of Example 54, 5.4 g (0.029 mole) of 2-(8-quinolinyloxy)ethanol was reacted with sulfamoyl chloride. During work-up of the reaction, quite a bit of light-yellow material deposited out from the organic-aqueous system. $^1$H NMR of this material suggested that it might be a quaternary salt. The oily product obtained at the end of the work-up procedure weighed 2.7 g. This oil was dissolved in acetonitrile-isopropyl alcohol and acidified with 37% hydrochloric acid. The mixture was evaporated to almost dryness and then redissolved in methanol. To the solution was added ethyl acetate and most of the methanol was evaporated carefully. The light-yellow solid was collected and dried at 40° C. in vacuum overnight to give 2.4 g solid monohydrochloride, mp 138°-140° C.

Analysis: Calculated for $C_{11}H_{12}N_2O_4S \cdot HCl$: C, 43.35; H, 4.30; N, 9.19. Found: C, 43.26; H, 4.38; N, 9.04.

EXAMPLE 62

Methylsulfamic acid 4-chlorophenyl ester

A solution of 18.1 g (0.14 mole) of N-methylsulfamoyl chloride (Preparation 22) in 20 ml methylene chloride was added at 10°-20° C. to a solution of 12.8 g (0.10 mole) of 4-chlorophenol and 15 g (0.15 mole) of triethylamine in 50 ml of methylene chloride. The cooling was removed and the mixture stirred at ambient temperature for four hours. The mixture was filtered to remove the triethylamine hydrochloride. The filtrate was extracted with dilute HCl (6 ml of 37% hydrochloric acid in 60 ml water) followed by a water wash. The organic layer was then extracted with dilute potassium carbonate (8.0 g in 80 ml water) followed by a water wash. The methylene chloride layer was concentrated to 21.7 g of yellow oil which crystallized on cooling. The solid was stirred in a mixture of 10 ml toluene and 63 ml petroleum ether to obtain 20.3 g of yellow solid. The 20.3 g was recrystallized from 1:2 toluene:petroleum ether to give 8.73 g of white solid, mp 61°-62° C.

Analysis: Calculated for $C_7H_8ClNO_3S$: C, 37.93; H, 3.64; N, 6.32. Found: C, 37.59; H, 3.69; N, 6.42.

EXAMPLE 63

Ethylsulfamic acid 1-[(2-methoxyphenoxy)methyl-1,2-ethanediyl ester

A solution of 19.8 g (0.1 mole) of glyceryl guaiacolate in 100 ml of methylene chloride and 21.6 ml (0.26 mole) of pyridine was added in a thin stream to a stirred solution of 37.3 g (0.26 mole) of ethylsulfamoyl chloride (Preparation 23) in 150 ml of methylene chloride, and the reaction mixture was stirred at ambient temperature overnight. The reaction mixture was treated with 150 ml of 2N hydrochloric acid solution, and the layers were separated. The organic layer was washed with 150 ml of 2N hydrochloric acid solution, twice with 150 ml portions of water, dried (magnesium sulfate), and the solvent was evaporated under reduced pressure. The residue was purified by chromatography (4.5×90 cm glass column; 500 g of silica gel; methylene chloride-acetone, 25:1). Fractions containing the product were combined, and the solvents were evaporated under reduced pressure to give 20.2 g (49%) of the title compound as a light-yellow, viscous oil containing a trace of methylene chloride.

Analysis: Calculated for $C_{14}H_{24}N_2O_8S_2$: C, 40.77; H, 5.86; N, 6.79. Found: C, 40.21; H, 5.94; N, 6.77.

Analysis: Calc. for $C_{14}H_{24}N_2O_8S_2 \cdot 0.03CH_2Cl_2$: C, 40.60; H, 5.84; N, 6.75.

EXAMPLE 64

Ethylsulfamic acid 1-(phenoxymethyl)1,2-ethanediyl ester

This compound was prepared by the procedure used in Example 63. Thus, 17.7 g (0.1 mole) of 3-phenoxy-1,2-propanediol (95%, Aldrich), 37.3 g (0.26 mole) of ethylsulfamoyl chloride, and 21.6 ml (0.26 mole) of pyridine in 250 ml of methylene chloride gave 37.5 g of a yellow, viscous residue which solidified upon standing. The solid was recrystallized from ethyl ether-petroleum ether (30°–60° C.) to give 23.3 g (61%) of the title compound as a white solid, mp 60°–63° C.

Analysis: Calculated for $C_{13}H_{22}N_2O_7S_2$: C, 40.83; H, 5.80; N, 7.33. Found: C, 40.59; H, 5.93; N, 7.30.

EXAMPLE 65

Sulfamic acid 2,3-dihydro-1,4-benzodioxin-2-methyl ester

This compound was prepared using the procedure used in Example 60. Thus 25.7 g (0.15 mole) of 2-hydroxymethyl-1,4-benzodioxan (97%, Aldrich), 52.3 ml (0.59 mole) of chlorosulfonyl isocyanate (98%, Aldrich), 61.6 g (0.61 mole) of triethylamine and 9.9 g (0.55 mole) of water in 250 ml of acetonitrile gave a viscous residue. The residue was partitioned between 700 ml of chloroform and 300 ml of water. The organic layer was washed with give 300 ml portions of water (aqueous layer pH was neutral to pH paper), dried (magnesium sulfate), and the solvent was evaporated under reduced pressure to give a semi-solid residue. This residue was triturated with 70 ml of chloroform-hexanes (1:4), and the resulting solid was collected by filtration. The solid was recrystallized from chloroform-hexanes to yield 9.0 g (24%) of the title compound as a white solid, mp 93°–95° C. [lit. mp 94°–96° C. ($CHCl_3$), *J. Med. Chem.* 30, 880 (1987)].

Analysis: Calculated for $C_9H_{11}NO_5S$: C, 44.08; H, 4.52; N, 5.71. Found: C, 44.19; H, 4.64; N, 5.76.

EXAMPLE 66

Sulfamic acid 2-(3-pyridinyloxy)ethyl ester

A mixture of 4.9 g (0.035 mole) of 2(3-pyridinyloxy)ethanol (Preparation 18) and 8 g (0.046 mole) of sulfamic acid phenyl ester (Example 33) in 100 ml of dioxane was heated at reflux temperatue for 20 min. and the solvent then evaporated. The residue was triturated with 250 ml of acetone, filtered, and the filtrate acidified with a solution of anhydrous hydrogen chloride in isopropyl alcohol and the sticky brown precipitate collected. The brown solid was redissolved in 125 ml of methanol and diluted with 125 ml of ethanol. The solution was stirred with charcoal, filtered, and the filtrate partially evaporated to give a suspension. The suspension was diluted with isopropyl alcohol-isopropyl ether and filtered. The solid was dried at 50° C. for 18 hr and then at 70° C. for 18 hr in a vacuum oven. The yield was 4.5 g of solid title compound as the monohydrochloride, mp 156°–157°·C.

Analysis: Calculated for $C_7H_{10}N_2O_4S \cdot HCl$: C, 33.01; H, 4.35; N, 11.00. Found: C, 33.51; H, 4.55; N, 10.43.

EXAMPLE 67

(1-Methylethyl)sulfamic acid 1-phenoxymethyl-1,2-ethanediyl ester

This compound was prepared according to the procedure of Example 63. Thus 19.5 g (0.11 mole) of 3-phenoxy-1,2-propanediol, 63.0 g (0.26 mole) of pyridine in 250 ml of methylene chloride gave 63.9 g of a brown, viscous oil. The oil was purified by column chromatography on silica gel using methylene chloride-acetone (60:1) to elute the material. Desired fractions were combined and concentrated to yield a white solid. The solid was recrystallized from ethyl ether-petroleum ether (30°–60° C.) to yield 28.1 g (62%) of white solid, mp 77°–80° C.

Analysis: Calculated for $C_{15}H_{26}N_2O_7S_2$: C, 43.89; H, 6.38; N, 6.82. Found: C, 43.82; H, 6.52; N, 6.84.

EXAMPLE 68

(1,1-Dimethylethyl)sulfamic acid 1-(Phenoxymethyl)-1,2-ethanediyl ester

This compound was prepared by the procedure used in Example 63. Thus, 13.7 g (0.077 mole) of 3-phenoxy-1,2-propanediol (95%, Aldrich), 31.3 g (0.18 mole) of N-(t-butylsulfamoyl) chloride (Preparation 23) and 15.2 ml (0.18 mol) of pyridine in 250 ml of methylene chloride gave 30.8 g of a dark, viscous oil. The oil was purified by chromatography (4.5×90 cm glass column, 500 g of silica gel, methylene chloride-acetone, 80:1). Fractions containing the desired compound were combined and the solvents evaporated under reduced pressure to yield a viscous oil that solidified upon standing. The solid was recrystallized from ethyl ether-petroleum ether (30°–60° C.) to give 12.9 g (38%) of the title compound as a white solid, mp 101.5°–103° C.

Analysis: Calculated for $C_{17}H_{30}N_2O_7S_2$: C, 46.56; H, 6.90; N, 6.35. Found: C, 46.66; H, 7.05; N, 6.38.

EXAMPLE 69

Sulfamic acid 4-(methoxycarbonyl)phenyl ester

Chlorosulfonylisocyanate (8.8 ml, 0.1 mole) was added to 200 ml toluene. Solid methyl 4-hydroxybenzoate (15.2 g, 0.1 mole) was added to the stirred solution. The mixture was heated at reflux for 1.5 hr then cooled and treated with about 8 ml water and some tetrahydrofuran. Solvents were then removed by evaporation. The residue was triturated with ethyl acetate-isopropyl ether. The insoluble solid was removed by filtration. The filtrate was concentrated and then triturated in isopropyl ether. The solid was collected and weighed 8.6 g. Recrystallization from acetone-isopropyl ether gave a white solid which was dried under vacuum overnight at room temperature to 3.9 g, mp 116°–118° C.

Analysis: Calculated for $C_8H_9NO_5S$: C, 41.56; H, 3.92; N, 6.06. Found: C, 41.53; H, 3.97; N, 6.05.

EXAMPLE 70

Sulfamic acid 3-(methoxycarbonyl)phenyl ester

Following the procedure of Example 78, a reaction of 8.8 ml (0.10 mole) chlorosulfonyl isocyanate and 15.2 g (0.10 mole) of methyl 3-hydroxybenzoate in 200 ml of toluene was heated at reflux for 7.5 hr and worked up to obtain 10.53 g, mp 145°–146° C.

Analysis: Calculated for C$_8$H$_9$NO$_5$S: C, 41.56; H, 3.92; N, 6.06. Found: C, 41.30; H, 3.94; N, 6.06.

EXAMPLE 71

Sulfamic acid 3-(acetylamino)phenyl ester

By the same method described for Example 53, the title compound was prepared from m-acetamidophenol (12.10 g, 0.08 m), reacting with the sulfamoyl chloride generated from water and chlorosulfonyl isocyanate. The crude product contained desired product and starting material. The product was isolated by chromatography on 100 g silica gel, eluted first with 7:3 methylene chloride/acetonitrile and then increasing the proportion of acetonitrile in the eluting solvent. The main fraction was evaporated and triturated with isopropyl alcohol/isopropyl ether to give 4 g of white solid, recrystallized from acetonitrile/isopropyl ether, and dried in vacuum at 60° C. overnight to give 3.73 g of solid, mp 148°–149° C.

Analysis: Calculated for C$_8$H$_{10}$N$_2$O$_4$S: C, 41.73; H, 4.38; N, 12.17. Found: C, 42.06; H, 4.46; N, 12.35.

EXAMPLE 72

Sulfamic acid 4-carboxyphenyl ester

Benzyl 4-hydroxybenzoate (22.8 g, 0.1 mole) was converted to its benzyloxycarbonylsulfamoyl derivative by the same procedure as described in Example 50. This intermediate was isolated as an oil and was hydrogenated over 5% Pd-C by the same manner to give 4.5 g solid. Recrystallization from methanol-acetonitrile yielded 3 g of pure product, mp 184°–186° C.

Analysis: Calculated for C$_7$H$_7$NO$_5$S: C, 38.71; H, 3.25; N, 6.45. Found: C, 38.71; H, 3.32; N, 6.62.

EXAMPLE 73

Sulfamic acid 4-(1H-imidazol-1-yl)phenyl ester

To a chilled solution of chlorosulfonyl isocyanate (8.7 ml, 0.10 mole) in 50 ml of methylene chloride was added a solution of 10.8 g (0.10 mole) of benzyl alcohol in 200 ml of methylene chloride over a period of 6 minutes at 3°–15° C. The reaction was then stirred at ambient temperature for 2 hours and then chilled in an ice-water bath. To this solution was added 4-(imidazol-1-yl)phenol (12 g, 0.075 mole) as a solid, and the mixture was stirred at room temperature for 45 minutes. Triethylamine (14 ml, 0.1 mole) was then added to the suspension, and the reaction became a dark brown solution. The mixture was stirred for two days, and the solid was collected by filtration, stirred in water for half an hour, and filtered again, rinsed with isopropyl alcohol and isopropyl ether. This solid intermediate weighed 18.24 g (65%) and $^1$H NMR showed it exists as zwitterion. The zwitterion (18 g) was added to a solution of isopropyl alcohol containing 0.05 mole hydrogen chloride and diluted with 100 ml methanol. The resultant solution was mixed with 1.8 g Pd-C (5%) and hydrogenated until there was no further absorption of hydrogen. The catalyst was removed, and the solution was concentrated to give 10 g solid. Part of the solid was recrystallized by dissolving in excess amount of methanol, filtering, and concentrating to crystallize out about 5 g solid. The solid was dried in vacuum oven at 80° C. overnight, mp 198°–200° C.

Analysis: Calculated for C$_9$H$_9$N$_3$O$_3$S.HCl: C, 39.21; H, 3.66; N, 15.24. Found: C, 39.07; H, 3.65; N, 15.15.

EXAMPLE 74

(1-Methylethyl)sulfamic acid phenyl ester

This compound was prepared according to the procedure of Example 52. Thus a solution of 16.2 g (0.17 mole) of phenol and 33.0 g (0.21 mole) of N-isopropylsulfamoyl chloride (Preparation 22) in 150 ml of toluene gave a dark oil which was purified by column chromatography on silica gel using ethyl acetate-hexanes (1:16) to elute the product. Desired fractions were combined and concentrated to yield 11.7 g (32%) of the title compound as a light-yellow oil.

Analysis: Calculated for C$_9$H$_{13}$NO$_3$S: C, 50.22; H, 6.09; N, 6.51. Found: C, 50.20; H, 6.23; N, 6.31.

EXAMPLE 75

Sulfamic acid (3,4-dichlorophenyl)ester

A solution of 16.3 g (0.1 mole) of 3,4-dichlorophenol in 100 ml of toluene was heated at reflux utilizing a Dean-Stark trap to remove any water that may have been present. The solution was cooled in an ice bath, treated with 9.1 ml (14.8 g, 0.105 mole) of chlorosulfonyl isocyanate, and heated at reflux overnight. The solution was cooled in an ice bath, vigorously stirred, and treated dropwise with water until carbon dioxide evolution ceased. The solid which precipitated was collected by filtration, washed with water and benzene, dried, and recrystallized from benzene to yield 19.9 g (82%) of a white solid, mp 121°–123° C.

Analysis: Calculated for C$_6$H$_5$Cl$_2$NO$_3$S: C, 29.77; H, 2.08; N, 5.79. Found: C, 29.94; H, 2.10; N, 5.93.

EXAMPLE 76

Sulfamic acid (4-nitrophenyl ester)

This compound was prepared according to the procedure of Example 75. A mixture of 13.9 g (0.1 mole) of 4-nitrophenol and 14.8 g (0.105 mole) of chlorosulfonyl isocyanate in 100 ml of toluene gave 17.8 g (82%) of tan solid, mp 104°–111° C. (benzene-acetonitrile).

Analysis: Calculated for C$_6$H$_6$N$_2$O$_5$S: C, 33.03; H, 2.77; N, 12.84. Found: C, 33.29; H, 2.80; N, 12.85.

EXAMPLE 77

(Ethoxycarbonyl)sulfamic acid phenyl ester

Chlorosulfonyl isocyanate (98%, 13.4 ml, 0.15 mole) was stirred in 40 ml of methylene chloride in an acetone-ice bath. Ethanol (8.8 ml, 0.15 mole) dissolved in 20 ml methylene chloride was added dropwise over 28 minutes. The reaction was stirred at room temperature for 15 minutes and then chilled in an ice bath. To the reaction was added a solution of phenol (11.3 g, 0.12 mole) and triethylamine (21 ml, 0.15 mole) in methylene chloride (20 ml) over 27 minutes. The reaction was stirred at ambient temperature for 4 hours and then extracted twice with dilute hydrochloric acid. The organic layer was dried over sodium sulfate and evaporated to 31 g oil. This oil was chromatographed on about 300 g silica gel eluted with 2% ethyl acetate/methylene chloride. The pure fractions were combined and concentrated to 15 g oil.

Analysis: Calculated for C$_9$H$_{11}$NO$_4$S: C, 44.08; H, 4.52; N, 5.71. Found: C, 43.59; H, 4.55; N, 5.70.

EXAMPLE 78

Ethylsulfamic acid phenyl ester

A solution of 18.8 g (0.2 mole) of phenol and 38.4 g (0.27 mole) of ethylaminosulfonyl chloride (Preparation 23) in 150 ml of toluene was stirred and heated at reflux for 16 hr. The solution was cooled and then treated with 250 ml of a 20% sodium bicarbonate solution. The layers were separated and the organic layer was washed successively with 250 ml of a 20% sodium bicarbonate solution, two 300-ml portions of water and dried (magnesium sulfate). The solvent was evaporated under reduced pressure and the oily residue was purified by chromatography (4.5×105 cm glass column; 550 g of silica gel; ethyl acetate-hexanes, 1:16). Fractions containing the product were combined and the solvents evaporated under reduced pressure to give 28.5 g (71%) of the title compound as a colorless liquid. Elemental analysis suggested that the product contained water.

Analysis: Calculated for $C_8H_{11}NO_3S.0.1H_2O$: C, 47.32; H, 5.56; N, 6.90. Found: C, 47.06; H, 5.69; N, 7.13.

EXAMPLE 79

Sulfamic acid 4-phenyl-1,2,5-thiadiazol-3-yl ester

A slurry of 3-hydroxy-4-phenyl-1,2,5-thiadiazole (15.0 g, 0.084 mole) in acetonitrile (100 ml) was treated by the simultaneous dropwise addition of a sulfamoyl chloride solution in acetonitrile (0.20 mole, 66 ml of 3M) and a diisopropylethylamine solution (0.22 mole in enough 1:1 acetonitrile/methylene chloride to make 66 ml). High Pressure Liquid Chromatography analysis indicated a maximum of 85% conversion of starting material to product. The reaction was worked up by concentration of the reaction mixture and partitioning the residue between ethyl ether and water. Concentration of the ether fraction gave a white paste from which desired product was separated by dissolving in a small amount of acetonitrile. The product was crystallized from the acetonitrile to give 2.8 g (13%) of the title compound as a white powder, mp 128°-130° C.

Analysis: Calculated for $C_8H_7N_3O_3S_2$: C, 37.35; H, 2.74; N, 16.33. Found: C, 37.30; H, 2.75, N, 16.41.

EXAMPLE 80

Sulfamic acid 3-nitrophenyl ester

This compound was prepared according to the procedure used in Example 75. A mixture of 13.9 g (0.1 mole) of 3-nitrophenol and 14.8 g (0.105 mole) of chlorosulfonyl isocyanate in 100 ml of toluene gave 16.9 g (78%) of tan flakes, mp 118°-120° C.

Analysis: Calculated for $C_6H_6N_2O_5S$: C, 33.03; H, 2.77; N, 12.84. Found: C, 33.18; H, 2.81; N, 12.95.

EXAMPLE 81

Sulfamic acid 3-(trifluoromethyl)phenyl ester

This compound was prepared according to the procedure used in Example 75. A mixture of 18.4 g (0.114 mole) of α, α, α-trifluoro-m-cresol, 14.8 g (0.105 mole) of chlorosulfonyl isocyanate and 100 ml of toluene gave 22.5 g (82%) of a white solid, mp 100°-102° C.

Analysis: Calculated for $C_7H_6F_3NO_3S$: C, 34.86; H, 2.51; N, 5.81. Found: C, 35.04; H, 2.48; N, 5.86.

EXAMPLE 82

Sulfamic acid (1,1'-biphenyl)-4-yl ester

This compound was prepared according to the procedure used in Example 75. A mixture of 17.0 g (0.1 mole) of 4-phenylphenol, 14.8 g (0.105 mole) of chlorosulfonyl isocyanate and 100 ml of toluene gave 17.2 g (69%) of white crystals, mp 166°-168° C. (benzene-acetonitrile).

Analysis: Calculated for $C_{12}H_{11}NO_3S$: C, 57.82; H, 4.45; N, 5.62. Found: C, 58.06; H, 4.47; N, 5.66.

EXAMPLE 83

Sulfamic acid 4-nitro-3-(trifluoromethyl)phenyl ester

This compound was prepared according to the procedure used in Example 75. A mixture of 10.4 g (0.05 mole) of 5-hydroxy-2-nitrobenzotrifluoride, 7.8 g (0.055 mole) of chlorosulfonyl isocyanate and 75 ml of toluene gave 11.1 g (78%) of tan solid, mp 95°-97° C. (benzene).

Analysis: Calculated for $C_7H_5F_3N_2O_5S$: C, 29.38; H, 1.76; N, 9.79. Found: C, 29.30; H, 1.69; N, 9.81.

EXAMPLE 84

Sulfamic acid 4-methyl-2-oxo-2H-1-benzopyran-7-yl ester

A slurry of 7-hydroxy-4-methylcoumarin (17.6 g, 0.10 mole) in acetonitrile (100 ml) was treated with a total of 84 ml of 3M sulfamoyl chloride (0.255 mole) in acetonitrile. The mixture was then treated dropwise with triethylamine (25.8 g, 0.255 mole). The reaction temperature was allowed to rise to 45° without any cooling. The mixture was stirred overnight at ambient temperature. The precipitate was collected, triturated with water, and dried in a vacuum oven at 70° C. for 15 hr to give 10.5 g (41%) of white powder, mp 161°-164° C.

Analysis: Calculated for $C_{10}H_9NO_5S$: C, 47.06; H, 3.55; N, 5.49. Found: C, 47.08; H, 3.58; N, 5.56.

EXAMPLE 85

Sulfamic acid 2-chlorophenyl ester

This compound was prepared by the procedure used in Example 75. A mixture of 12.8 g (0.1 mole) of 2-chlorophenol, 14.8 g (0.105 mole) of chlorosulfonyl isocyanate and 75 ml of toluene gave 12.2 g (59%) of the title compound as a white solid, mp 62.5°-63.5° C. (cyclohexane-benzene).

Analysis: Calculated for $C_6H_6ClNO_3S$: C, 34.71; H, 2.91; N, 6.75. Found: C, 34.50; H, 2.92; N, 6.76.

EXAMPLE 86

Methylsulfamic acid 4-(1H-imidazol-1-yl)phenyl ester

Triethylamine (11.2 ml, 0.08 mole) and 4-(imidazo-1-yl)phenol (9.6 g, 0.06 mole) were stirred in 100 ml methylene chloride as a suspension in an ice bath. To this suspension was added a solution of methylsulfamoyl chloride (10.8 g, 0.08 mole) in 10 ml methylene chloride over 4 minutes. The ice bath was then removed and the reaction was stirred at room temperature overnight. The grayish suspension slowly changed to a tan suspension. The solid was filtered and rinsed with methylene chloride and then dissolved in 300 ml methanol. The solution was acidified with HCl/isopropyl alcohol and stirred with charcoal. The almost colorless filtrate was mixed with some isopropyl alcohol and then concentrated. The residual solid was triturated in isopropyl alcohol/isopropyl ether, collected by filtration, and dried overnight at 80° C. in a vacuum oven to yield 11.34 g of solid title compound as the monohydrochloride, mp 221°–223° C.

Analysis: Calculated for $C_{10}H_{11}N_3O_3S\cdot HCl$: C, 41.46; H, 4.18; N, 14.50. Found: C, 41.40; H, 4.21; N, 14.38.

EXAMPLE 87

Sulfamic acid (2-naphthalenyl) ester

To a cold (ice-acetone bath) solution of 11.3 ml (0.13 mole, 18.4 g) of chlorosulfonyl isocyanate in 50 ml of acetonitrile was added dropwise a solution of 2.3 g (0.13 mole) of water in 10 ml of acetonitrile at such a rate that the temperature was maintained between −2° to 7° C. (ca. 45 min). After the addition was complete, the solution was stirred for 5 min and then treated dropwise with a solution of 14.4 g (0.1 mole) of β-naphthol, 20.9 ml (0.15 mole, 15.2 g) of triethylamine and 100 ml of acetonitrile at such a rate that the temperature did not exceed 10° C. (ca. 30 min). The mixture was stirred at ambient temperature for 3.5 h and then diluted with 100 ml of ethyl acetate and 50 ml of water. The layers were separated and the organic layer was washed once with 50 ml of water and once with 100 ml of brine, dried (sodium sulfate), and concentrated to give 24 g of dark gum. The gum was purified by column chromatography on 400 g of silica gel eluted with methylene chloride. Fractions containing the desired product were combined and concentrated to yield 5.7 g (26%) of the title compound as a white solid, mp 114°–115° C. (benzene).

Analysis: Calculated for $C_{10}H_9NO_3S$: C, 53.80; H, 4.06; N, 6.27. Found: C, 53.83; H, 4.02; N, 6.25.

EXAMPLE 88

Methylsulfamic acid 3-phenoxy-1,2-propanediyl ester

To a vigorously stirred solution of 17.7 g (0.1 mole) of 3-phenoxy-1,2-propanediol in 250 ml of methylene chloride was added simultaneously, over a 30 min period, 35.8 g (0.28 mole) of methylaminosulfonyl chloride (Preparation 22) and 36.0 g (0.28 mole) of diisopropylethylamine. The dark reaction mixture was stirred for 3 hr and the solvent was evaporated under reduced pressure to yield a brown, viscous oil. The oil was partitioned between ethyl acetate and a 2N hydrochloric acid solution (250 ml each). The organic layer was further washed with two 250-ml portions of 2N hydrochloric acid solution, 250 ml of water, and dried (magnesium sulfate). The solvent was evaporated under reduced pressure and the viscous, oily residue was purified by chromatography (4.5×105 cm glass column; 520 g of silica gel; methylene chloride-acetone, 100:3). Fractions containing the product were combined and the solvents evaporated under reduced pressure to give 25.7 g (73%) of the title compound as a pale-yellow gum.

Analysis: Calculated for $C_{11}H_{18}N_2O_7S_2$: C, 37.28; H, 5.12; N, 7.90. Found: C, 36.75; H, 5.17; N, 7.83.

EXAMPLE 89

Sulfamic acid 4-(2H-1,2,4-triazol-2-yl)phenyl ester 4-(1H-1,2,4-triazol-1-yl)phenol (5.0 g, 0.031 mole) was suspended in methylene chloride (30 ml) and sulfamoyl chloride (7.13 g, 0.062 mole) added to the stirring mixture. Triethylamine (6.27 g, 0.062 mole) was added dropwise while maintaining the temperature between 25°–30° C. After the addition was complete the reaction was stirred for several hours at room temperature. An aliquot was removed and injected onto an High Pressure Liquid Chromatography diol column (10% methanol in ethyl acetate) which indicated reaction had not gone to completion. The reaction was treated with an additional 0.031 mole of sulfamoyl chloride and triethylamine. The reaction stirred overnight at room temperature and was worked up after $^1H$ NMR indicated reaction had gone to completion. The solvent was evaporated and the residue partitioned between ethyl acetate/acetonitrile (1:1)/aqueous sodium hydroxide, sodium bicarbonate (1:1). The organic layer was evaporated and the base isolated as an off-white powder (4.78 g, 64%). The crystals were dissolved in hot isopropyl alcohol, cooled and the mixture filtered. The filtrate containing the base was evaporated to a residue, dissolved in methanol and a solution of anhydrous HCl/isopropyl alcohol added. White crystals fell out of solution as more isopropyl alcohol was added and methanol removed. The crystals were filtered, dried and analyzed as the half hydrochloride (0.80 g, 0.0029 mole, 9%, mp 169°–173° C.).

Analysis: Calculated for $C_8H_8N_4O\cdot 0.5HCl$: C, 37.18; H, 3.32; N, 21.68. Found: C, 36.93; H, 3.30; N, 21.44.

EXAMPLE 90

Sulfamic acid 4-benzoylphenyl ester

This compound was prepared according to the procedure used in Example 75. A mixture of 9.9 g (0.05 mole) of 4-hydroxybenzophenone, 7.1 g (0.0505 mole) of chlorosulfonyl isocyanate and 75 ml of toluene gave 8.1 g (58%) of the title compound as off-white flakes, mp 131°–133° C.

Analysis: Calculated for $C_{13}H_{11}NO_4S$: C, 56.31; H, 4.00; N, 5.05. Found: C, 56.03; H, 3.92; N, 5.07.

EXAMPLE 91

Sulfamic acid 3-bromophenyl ester

This compound was prepared according to the procedure used in Example 75. A mixture of 17.3 g (0.1 mole) of 3-bromophenol, 9.1 ml (14.8 g, 0.105 mole) of chlorosulfonyl isocyanate and 100 ml of toluene gave 19.8 g (70%) of white solid, mp 90°–91.5° C. (benzene).

Analysis: Calculated for $C_6H_6BrNO_3S$: C, 28.59; H, 2.40; N, 5.56. Found: C, 28.35; H, 2.46; N, 5.52.

EXAMPLE 92

Sulfamic acid 4-(trifluoromethyl)phenyl ester

This compound was prepared according to the procedure used in Example 75. A mixture of 9.6 g (0.059 mole) of α,α,α-trifluoro-p-cresol, 5.7 ml (9.2 g, 0.065 mole) of chlorosulfonyl isocyanate and 75 ml of toluene gave 11.2 g (70%) of white solid, mp 111°–112° C. (benzene).

Analysis: Calculated for $C_7H_6F_3NO_3S$: C, 34.86; H, 2.51; N, 5.81. Found: C, 34.75; H, 2.47; N, 5.80.

EXAMPLE 93

Sulfamic acid 3-benzoylphenyl ester

This compound was prepared according to the procedure used in Example 75. A mixture of 9.9 g (0.05 mole) of 3-hydroxybenzophenone and 4.4 ml (7.1 g, 0.0505 mole) of chlorosulfonyl isocyanate in 75 ml of toluene gave a solid as residue. This residue was recrystallized successively from benzene and then methylene chloride to yield 4.2 g (30%) of the title compound as a white solid, mp 72°–74° C.

Analysis: Calculated for $C_{13}H_{11}NO_4S$: C, 56.31; H, 4.00; N, 5.05. Found: C, 55.89; H, 3.95; N, 5.03.

EXAMPLE 94

Sulfamic acid 3-(dimethylamino)phenyl ester

A solution of 3-dimethylaminophenol (6.90 g, 0.05 mole) in 30 ml of acetonitrile was added in 13 minutes to a chilled (15° C.) stirred solution of 0.10 mole sulfamoyl chloride (Preparation 19) in 30 ml of acetonitrile. This was followed by the addition of 14 ml (0.10 mole) of triethylamine. The resultant mixture was stirred at room temperature overnight. The reaction was diluted with ethyl acetate (~60 ml) and then extracted twice with sodium bicarbonate solution. The aqueous layers were back extracted with 1:1 ethyl acetate/acetonitrile once. The organic layers were combined, dried over sodium sulfate, charcoaled, filtered, and evaporated to a black oil weighing 7.57 g.

The above reaction was repeated doubling the scale and all the black oil combined and chromatographed on 360 g of silica gel eluting with 10% acetonitrile/methylene chloride. The fractions containing the desired product also contained some starting material. These fractions were combined, concentrated, and redissolved in isopropyl alcohol. The solution was acidified with a solution of anhydrous HCl in isopropyl alcohol and crystallized to give 9.39 g of a light-greenish-brown solid. This solid was redissolved in methanol (charcoal) to give a light-blue filtrate. Evaporation and crystallization of the residue from isopropyl alcohol gave 8.5 g of off-white solid title compound as the monohydrochloride, mp 168°–70° C.

Analysis: Calculated for $C_8H_{12}N_2O_3S \cdot HCl$: C, 38.02; H, 5.19; N, 11.09. Found: C, 38.05; H, 5.34; N, 11.11.

EXAMPLE 95

Methylsulfamic acid 2-[4-(1H-imidazol-1-yl)phenoxy]ethyl ester

A solution of 4-imidazol-1-yl-phenol (20.0 g, 0.125 mole), 2-chloroethanol (40.25 g, 0.50 mole) and potassium carbonate (69.0 g, 0.50 mol) in 500 ml of methyl ethyl ketone was heated at reflux for 48 hr as its progress was being monitored by TLC (methanol:-methylene chloride 10:90). The reaction was then filtered, and the filtrate evaporated to a solid which was redissolved in hot isopropanol. The crystals which formed upon cooling were filtered, rinsed with isopropyl ether, and dried (7.36 g, 28.9% yield, $^1$H NMR: 95% pure). This intermediate alcohol (6.0 g, 0.029 mole) was suspended in methylene chloride (60 ml) and triethylamine (3.51 g, 0.0348 mole) added to the stirring suspension. The reaction was chilled at 10° C. and methylsulfamoyl chloride (4.51 g, 0.0348 mole) added dropwise allowing reaction to slowly warm to room temperature. After 1 hr of stirring, TLC indicated reaction was not complete so it was treated with additional 0.03 mole of base and methylsulfamoyl chloride and stirred overnight. After the reaction had gone to completion, it was evaporated to a residue. The residue was dissolved in ethyl acetate/acetonitrile (1:1) (200 ml) and washed with sodium bicarbonate/sodium chloride (1:1) (2×200 ml). The organic layer was evaporated and redissolved in hot ethanol. Upon cooling, crystals precipitated and were filtered and dried. They were then dissolved in methanol and anhydrous HCl in isopropyl alcohol added. A carbon filtration was done and the methanol evaporated as more isopropanol was added. Off-white crystals of the title compound, monohydrochloride, half hydrate precipitated and were filtered, dried, and analyzed (4.14 g, 42%, mp 85°–88° C.).

Analysis: Calc. for $C_{12}H_{15}N_3O_4 \cdot HCl \cdot 0.5H_2O$: C, 42.05; H, 5.00; N, 12.26. Found: C, 42.30; H, 4.99; N, 11.91.

EXAMPLE 96

Sulfamic acid 4-(aminosulfonyl)phenyl ester

This compound was prepared by the procedure used in Example 28. Thus, 20.2 g (0.12 mole) of p-hydroxybenzenesulfonamide, 43 ml (0.48 mole) of chlorosulfonyl isocyanate, 8.5 g (0.47 mole) of water and 53.3 g (0.53 mole) of triethylamine in 250 ml of acetonitrile gave 14.6 g of a viscous residue which solidified upon standing. The solid was purified by chromatography (4×150 cm glass column; 500 g of silica gel; acetone-methylene chloride, 1.5). Fractions containing the product were combined and the solvents evaporated under reduced pressure to give 9.0 g (30%) a solid. The solid was recrystallized from methylene chloride-acetone to give 2.1 g (7%) of the title compound as fluffy, white needles, mp 139°–142° C.

Analysis: Calculated for $C_6H_8N_2O_5S_2$: C, 28.57; H, 3.20; N, 11.11. Found: C, 28.50; H, 3.25; N, 10.99.

EXAMPLE 97

Sulfamic acid 2-(4-methyl-5-thiazolyl)ethyl ester

4-Methyl-5-thiazoleethanol (10.0 g, 0.0698 mole) was dissolved in acetonitrile, chilled, and sulfamoyl chloride (10.44 g, 0.091 mole) was added to the stirred solution. Triethylamine (9.19 g, 0.091 mole) was added dropwise while maintaining the temperature between 20°–25° C. A yellow solid precipitated after the addition was completed. The reaction was stirred at room temperature overnight, evaporated to a residue, and the residue partitioned between ethyl acetate/acetonitrile (1:1) and sodium bicarbonate/sodium chloride (1:1). The organic phase was treated with charcoal, dried (magnesium sulfate), filtered, and evaporated to a residue (9.29 g). The residue was dissolved in a small amount of methanol and isopropanol was added. The first crop (2.0 g) crystallized out of isopropanol as the methanol was evaporated. The crystals were collected and dried to yield 2.0 g (13%) of solid, mp 80°–83° C.

Analysis: Calc. for $C_6H_{10}N_2O_3S_2 \cdot 0.5H_2O \cdot 0.5C_3H_8O$: C, 34.47; H, 5.79; N, 10.72. Found: C, 34.15; H, 5.09; N, 11.59.

EXAMPLE 98

Sulfamic acid 3-[4-[bis(4-fluorophenyl)hydroxymethyl]-1-piperidinyl]propyl ester To a stirred cooled (ice-acetone bath) solution of 15 ml (0.172 mole) of chlorosulfonyl chloride in 100 ml of acetonitrile was added dropwise a solution of 3.2 g (0.177 mole) of water in 25 ml of acetonitrile at such a rate that the temperature did not exceed 0° C. (45 min). After the addition was completed, the mixture was stirred at −5° C. for 15 min and then treated dropwise with a solution of 18.1 g (0.050 mole) of α,α-bis(4-fluorophenyl)-1-(3-hydroxypropyl-4-piperidine methanol and 20.2 g (0.20 mole) of triethylamine in 150 ml of acetonitrile in 75 ml of methylene chloride at such a rate that the temperature did not exceed 0° C. The ice-acetone bath was removed and the mixture stirred for 2 hr and treated with 150 ml of water, stirred vigorously for 5 min and the layers were separated. The organic layer was concentrated under reduced pressure and the residue partitioned between ethyl acetate and water. The ethyl acetate layer was washed with water and brine, dried (sodium sulfate) and concentrated under reduced pressure to give a white solid. $^1$H NMR showed the solid to be the hydrochloride. The solid was crystallized successively from tetrahydrofuran and then ethyl acetate to yield 4.3 g (18%) of the title compound as the monohydrochloride, half ethylacetate, mp 78°–81° C.

Analysis: Calculated for $C_{23}H_{30}F_2N_2O_5S \cdot HCl \cdot 0.5C_4H_8O_2$: C, 53.02; H, 6.00; N, 5.38. Found: C, 52.93; H, 6.09; N, 5.20.

EXAMPLE 99

Sulfamic acid 3-cyanophenyl ester

Using the procedure described in Example 75, the title compound was prepared in 85% yield from 10.3 g (0.086 mole) of 3-cyanophenol and 8.3 ml (0.086 mole) of chlorosulfonyl isocyanate in 75 ml of toluene as a white solid, mp 101°–104° C. (benzene-acetonitrile).

Analysis: Calculated for $C_7H_6N_2O_3S$: C, 42.42; H, 3.05; N, 14.13. Found: C, 42.52; H, 2.82; N, 14.13.

EXAMPLE 100

Sulfamic acid 3-phenylphenyl ester

Using the procedure described in Example 75, the title compound was prepared from 17.0 g (0.010 mole) of 3-phenylphenol and 9.1 ml (0.105 mole) of chlorosulfonyl isocyanate in 100 ml of toluene to obtain 19.0 g (77%) of white flakes, mp 197°–199° C. (benzene-acetonitrile).

Analysis: Calculated for $C_{12}H_{11}NO_3S$: C, 57.82; H, 4.45; N, 5.62. Found: C, 57.60; H, 4.51; N, 5.59.

EXAMPLE 101

Methylsulfamic acid 2-phenoxy-1,3-propanediyl ester

To a stirred solution of 16.8 g (0.1 mole) of 2-phenoxy-1,3-propanediol (Preparation 25) in 100 ml of methylene chloride was added, dropwise and simultaneously 35.8 g (0.276 mole) of methylsulfamoyl chloride (Preparation 22) and 36.0 g (0.278 mole) of diisopropylethylamine over a 30 min period. The reaction mixture was stirred for 3 hr, the solvent evaporated under reduced pressure, and the residue was partitioned between ethyl acetate and 2N hydrochloric acid solution (250 ml each). The layers were separated and the organic layer was washed successively with two 250 ml portions of 2N hydrochloric acid and then 250 ml of water, dried, and the solvent was evaporated under reduced pressure to give 45.3 g of a dark, viscous residue. The residue was triturated with ethyl acetate and filtered. The filtrate was evaporated under reduced pressure to give a brown, viscous oil which was purified by column chromatography (4.5×90 cm glass column; 450 g of silica, methylene chloride acetone 100:3). Fractions containing the product were evaporated under reduced pressure and the viscous residue was twice purified by high pressure liquid chromatography (Waters Associates Prep LC/System 500A, PrepPAK® 500/silica; ethylacetate-hexanes, 1:2 and then methylene chloride-acetone, 100:3; flow rate 150 ml/min). Fractions containing the product were combined and the solvents evaporated under reduced pressure to yield 3.5 g (10%) of the title compound as a colorless, viscous oil.

Analysis: Calculated for $C_{11}H_{18}N_2O_7S_2$: C, 37.28; H, 5.12; N, 7.90. Found: C, 37.66; H, 5.49; N, 8.03.

EXAMPLE 102

Sulfamic acid 3-(1H-imidazol-1-yl)phenyl ester

A solution of 3(1H-imidazol-1-yl)phenol (8 g, 0.05 mole) in acetonitrile was treated in an ice bath with sulfamoyl chloride generated from 0.075 mole of chlorosulfonyl isocyanate (Preparation 19) followed by 0.075 mole of triethylamine. After stirring overnight at room temperature, TLC, and $^1$H NMR of a sample showed starting material still present. The reaction was then treated with another 0.075 mole each of sulfamoyl chloride and triethylamine for another night.

The reaction mixture was then concentrated and neutralized with both solid sodium bicarbonate and its solution. The slightly basic mixture was concentrated again to remove of the last trace of acetonitrile. The resultant solid suspension was chilled and then filtered. The sticky solid was dissolved in acetonitrile, stirred with sodium sulfate, magnesium sulfate and charcoal. The mixture was filtered and the filtrate was concentrated to obtain 9.24 g of oil. This oil was dissolved in acetonitrile/isopropyl alcohol, filtered, and acidified with a solution of hydrogen chloride in isopropyl alcohol. Some isopropyl ether was added to precipitate more solid. The solid was collected, weighed (4.63 g) and recrystallized from methanol/isopropyl alcohol to give 4.3 g of solid to the compound as the monohydrochloride, mp 164°–165° C.

Analysis: Calculated for $C_9H_9N_3O_3S \cdot HCl$: C, 39.21; H, 3.66; N, 15.24. Found: C, 38.92; H, 3.82; N, 14.80.

EXAMPLE 103

Sulfamic acid 3-iodophenyl ester

This compound was prepared using the procedure of Example 75 from 27.8 g (0.126 mole) of 3-iodophenol and 11.7 ml (0.135 mole) of chlorosulfonyl isocyanate in 100 ml of toluene to obtain 29.4 g (78%) of the title compound as white flakes, mp 106°–108° C. (benzene).

Analysis: Calculated for $C_6H_6INO_3S$: C, 24.10; H, 2.02; N, 4.68. Found: C, 23.94; H, 2.02; N, 4.75.

EXAMPLE 104

Dimethylsulfamic acid phenyl ester

This compound was prepared by the procedure of Example 52. Thus, a solution of 18.8 g (0.2 mol) of phenol and 29.0 ml (0.27 mol) of dimethyl-sulfamoyl chloride (Aldrich) in 150 ml of toluene gave a viscous oil. The oil was purified by high pressure liquid chromatography (Waters Associates Prep LC/System 500A; PrepPAK® 500/silica; ethyl acetate-hexanes, 1:25; flow rate 150 ml/min). Fractions containing the product were combined, the solvents evaporated under reduced pressure, and the viscous residue was dissolved in 500 ml of ethyl ether. The solution was washed successively with three 250 ml portions of a 20% sodium hydroxide solution, 300 ml of water and dried (magnesium sulfate). The solvent was evaporated under reduced pressure to give 10.8 g of a liquid. $^{13}$C NMR indicated that dimethyl-sulfamoyl chloride was present. Hence the liquid was again purified by high pressure liquid chromatography (Waters Associates Prep LC/System 500A; PrePAK 500/silica; ethyl acetate-hexanes, 1:20; flow rate 100 ml/min). Fractions containing the product were combined and the solvents evaporated under reduced pressure to yield 6.5 g (16%) of the title compound as a colorless liquid.

Analysis: Calculated for $C_8H_{11}NO_3S$: C, 47.75; H, 5.51; N, 6.96. Found: C, 47.49; H, 5.47; N, 6.88.

EXAMPLE 105

Sulfamic acid 4-methylphenyl ester

This compound was prepared by the procedure used in Example 75. Thus, a solution of 10.8 g (0.1 mole) of 4-methylphenol and 14.8 g (0.105 mole) of chlorosulfonyl isocyanate (95%, Aldrich) in 100 ml of toluene gave 10.3 g (55%) of the title compound as a white solid, mp 80°-82° C. (benzene-petroleum ether, 30°-60° C.).

Analysis: Calculated for $C_7H_9NO_3S$: C, 44.91; H, 4.85; N, 7.48. Found: C, 44.91; H, 4.81; N, 7.40.

EXAMPLE 106

Sulfamic acid 3-(1,1-dimethylethyl)phenyl ester

This compound was prepared according to the procedure used in Example 75. Thus, 15.0 g (0.1 mole) of 3-t-butylphenol (99%, Aldrich) and 14.8 g (0.105 mole) of chlorosulfonyl isocyanate (95%, Aldrich) in 150 ml of xylene gave 13.3 g of a viscous oil that solidified upon standing. The solid was recrystallized from benzene-petroleum ether 3(0°-60° C.) to give 9.5 g (41%) of the title compound as a white solid, mp 78°-81° C.

Analysis: Calculated for $C_{10}H_{15}NO_3S$: C, 52.38; H, 6.59; N, 6.11. Found: C, 52.46; H, 6.61; N, 6.08.

EXAMPLE 107

Sulfamic acid 3,5-dichlorophenyl ester

The procedure used in Example 75 was used to prepare this compound from a mixture of 16.3 g (0.10 mole) of 3,5-dichlorophenol and 9.1 ml (0.105 mole) of chlorosulfonyl isocyanate in 75 ml of toluene. The compound was obtained in 83% yield as a white, fluffy solid, mp 146°-147° C. (benzene).

Analysis: Calculated for $C_6H_5Cl_2NO_3S$: C, 29.77; H, 2.08; N, 5.77. Found: C, 29.78; H, 2.05; N, 5.76.

EXAMPLE 108

Sulfamic acid 2,3-dichlorophenyl ester

This compound was prepared according to the procedure of Example 75. Thus, a mixture of 16.3 g (0.10 mole) of 2,3-dichlorophenol and 9.1 ml (0.105 mole) of chlorosulfonyl isocyanate in 75 ml of toluene gave 17.4 g (72%) of the title compound as an off-white solid, mp 116°-117° C. (benzene).

Analysis: Calculated for $C_6H_5Cl_2NO_3S$: C, 29.77; H, 2.08; N, 5.77. Found: C, 29.88; H, 2.03; N, 5.77.

EXAMPLE 109

Sulfamic acid 4-cyanophenyl ester

This compound was prepared by the procedure of Example 75 from a solution of 11.9 g (0.10 mole) of 4-cyanophenol (Aldrich Chemical Co.) and 9.1 ml (0.105 mole) of chlorosulfonyl isocyanate in 75 ml of toluene. The solid product was recrystallized from benzene-acetonitrile to give 10.1 g (51%) of white solid, mp 154°-156° C.

Analysis: Calculated for $C_7H_6N_2O_3S$: C, 42.42; H, 3.05; N, 14.13. Found: C, 42.36; H, 2.99; N, 14.10.

EXAMPLE 110

Sulfamic acid 4-methoxyphenyl ester

This compound was prepared according to the procedure used in Example 75. Thus, a solution of 12.4 g (0.1 mole) of 4-methoxyphenol (Aldrich) and 14.8 g (0.105 mole) of chlorosulfonyl isocyanate (95%, Aldrich) in 100 ml of toluene gave a viscous, oily residue. The oil was purified by high pressure liquid chromatography (Waters Associates Prep LC/System 500A, Prep-PAK® 500 silica, methylene chloride; flow rate 200 ml/min). Fractions containing the product were combined and the solvent evaporated under reduced pressure to yield 9.6 g of a viscous oil that solidified upon standing. The solid was recrystallized from benzene-petroleum ether (30°-60° C.) to give 7.9 g (39%) of the title compound as a white solid, mp 62°-64° C.

Analysis: Calculated for $C_7H_9NO_4S$: C, 41.37; H, 4.46; N, 6.89. Found: C, 41.49; H, 4.47; N, 7.05.

EXAMPLE 111

Sulfamic acid 3(4-methyl-1H-imidazol-1-yl)phenyl ester

Following the procedure of Example 75, the title compound was prepared as the monohydrochloride from 8.7 g (0.05 mole) of 3(4-methyl-1H-imidazol-1-yl)phenol in 66% yield, mp 202°-204° C. (methanol-isopropyl ether).

Analysis: Calculated for $C_{10}H_{11}N_3O_3S \cdot HCl$: C, 41.46; H, 4.18; N, 14.50. Found: C, 41.35; H, 4.22; N, 14.35.

EXAMPLE 112

Sulfamic acid 2-methoxyphenyl ester

This compound was prepared according to the procedure of Example 60. Thus, a solution of 12.4 g (0.1 mole) of 2-methoxyphenol (Guaiacol; Aldrich), 40 ml (0.45 mole) of chlorosulfonyl isocyanate (98%; Aldrich), 7.4 g (0.41 mole) of water, and 59.0 g (0.46 mole) of diisopropylethylamine (99%, Aldrich) in 200 ml of acetonitrile and 100 ml of methylene chloride gave 9.0 g of a viscous oil. The oil was purified by high pressure liquid chromatography (Waters Associates Prep LC/System 500A; PrepPAK® 500 silica; methylene chloride; flow rate 150 ml/min). Fractions containing the product were combined and the solvents evaporated under reduced pressure to give 4.3 g (21%) of a viscous oil that solidified upon standing. The solid was recrystallized from benzene-petroleum ether (30°-60° C.) to give the title compound as white needles, mp 83°-85° C.

Analysis: Calculated for $C_7H_9NO_4S$: C, 41.37; H, 4.46; N, 6.89. Found: C, 41.30; H, 4.47; N, 6.84.

EXAMPLE 113

(S)-(−)-Sulfamic acid 1-[(2-methoxyphenoxy)methyl]-1,2-ethanediyl ester

A slurry of 5.94 g (0.03 mole) of R-(−)-glycerol guaiacolate (Preparation 31) in 35 ml of methylene chloride was treated by simultaneous addition of a solution of sulfamoyl chloride (0.083 mole) in acetonitrile (15 ml) and diisopropylethylamine (10.75 g, 0.083 mole) in methylene chloride (10 ml) over a 45 min period. The reaction was complete in 1.5 hr. The reaction mixture was washed twice with 100 ml portions of water and the organic layer was chromatographed on silica gel, eluting with 10% methanol in methylene chloride. The desired fractions were combined and concentrated to give 5.6 g (51%) of the title compound as a white powder, mp 136.0°–138.0° C., $[\alpha]_D^{22}$ −4.75° (c≅2 in MeOH).

Analysis: Calculated for $C_{10}H_{16}N_2O_8S_2$: C, 33.70; H, 4.53; N, 7.86. Found: C, 33.48; H, 4.62; N, 7.77.

EXAMPLE 114

(R)-(+)-Sulfamic acid 1-[(2-methoxyphenoxy)methyl]-1,2-ethanediyl ester

This compound was prepared by the procedure used in Example 113. A combination of 5.94 g (0.03 mole) of S-(+)glycerol guaiacolate, 0.083 mole of sulfamoyl chloride, and 10.8 g (0.083 mole) of diisopropylethylamine gave 4.5 g (41%) of the title compound as a white powder, mp 137.5°–139.0° C. $[\alpha]_D^{22}$ +4.80° (C=2 in MeOH).

Analysis: Calculated for $C_{10}H_{16}N_2O_8S_2$: C, 33.70; H, 4.53; N, 7.86. Found: C, 33.66; H, 4.69; N, 7.76.

EXAMPLE 115

Sulfamic acid 2,6-dichlorophenyl ester

This compound was prepared according to the procedure of Example 75 from a mixture of 16.3 g (0.10 mole) of 2,6-dichlorophenol and 9.1 ml (0.105 mole) of chlorosulfonyl isocyanate in 75 ml of toluene to obtain 17.3 g (71%) of the title compound after recrystallization from benzene, mp 114.5°–116° C.

Analysis: Calculated for $C_6H_5Cl_2NO_3S$: C, 29.77; H, 2.08; N, 5.77. Found: C, 29.62; H, 2.05; N, 5.81.

EXAMPLE 116

Sulfamic acid 3-methylphenyl ester

A solution of 0.25 mole of sulfamoyl chloride in 60 ml of acetonitrile was prepared according to the procedure of Example 17a. The solution was chilled (ice-water bath) and treated dropwise with a solution of 10.8 g (0.10 mole) of 3-methylphenol and 29.7 g (0.23 mole) of diisopropylethylamine in 100 ml of acetonitrile at such a rate that the temperature did not exceed 15° C. The solution was stirred at ambient temperature overnight and then diluted with 200 ml of ethyl acetate and 50 ml of water. The layers were separated and the organic layers washed successively with two 50 ml portions of water, 50 ml of 2N hydrochloric acid solution, 50 ml of water, brine, and dried (sodium sulfate) and concentrated to give a brown gum. The gum was purified by column chromatography (400 g silica gel eluted with methylene chloride). The appropriate fractions were combined and concentrated to give a solid residue which was recrystallized from benzene to yield 9.2 g (48%) of the title compound as white plates, mp 84°–85° C. (reported mp 88° C., Chem. Ber. 105, 2791–2799 (1972)).

Analysis: Calculated for $C_7H_9NO_3S$: C, 44.91; H, 4.84; N, 7.48. Found: C, 44.77; H, 4.88; N, 7.53.

EXAMPLE 117

Sulfamic acid 3-(4-phenyl-1H-imidazol-1-yl)phenyl ester

Using the same procedure of Example 73, 9.36 g (0.04 mole) of 3(4-phenyl-1H-imidazol-1-yl)phenol was converted to the title compound, monohydrochloride in 60% yield, mp 209°–211° C.

Analysis: Calculated for $C_{15}H_{13}N_3O_3S \cdot HCl$: C, 51.21; H, 4.01; N, 11.94. Found: C, 51.17; H, 3.99; N, 11.82.

EXAMPLE 118

Sulfamic acid 3-fluorophenyl ester

To a cooled (ice bath) solution of 11.2 g (0.1 mole) of 3-fluorophenol (98%, Aldrich) in 75 ml of toluene was added 9.1 ml (14.8 g, 0.105 mol) of chlorosulfonyl isocyanate, and the solution heated at reflux overnight. The solution was cooled and cautiously treated dropwise with water until carbon dioxide evolution ceased. An oil separated and ethyl acetate was added to dissolve this oil. The layers were separated and the organic layer was washed with water, dried (sodium sulfate) and concentrated to give an oil which gradually crystallized. The solid was purified by column chromatography on 400 g of silica gel eluted with methylene chloride. The appropriate fractions were combined and concentrated to yield 9.2 g (48%) of the title compound which was recrystallized from benzene to give a white solid, mp 53°–55° C.

Analysis: Calculated for $C_6H_6FNO_3S$: C, 37.70; H, 3.16; N, 7.33. Found: C, 37.70; H, 3.08; N, 7.35.

EXAMPLE 119

Sulfamic acid 3,5-bis(trifluoromethyl)phenyl ester

This compound was prepared using the procedure of Example 75 from a mixture of 9.8 g (0.043 mole) of 3,5-bis(trifluoromethyl)phenol and 3.9 ml (0.095 mole) of chlorosulfonyl isocyanate in 50 ml of toluene. The solid product was recrystallized from benzene to yield 6.4 g (48%) of a pale yellow solid; mp 118°–120° C.

Analysis: Calculated for $C_8H_5F_6NO_3S$: C, 31.08; H, 1.63; N, 4.53. Found: C, 31.11; H, 1.52; N, 4.60.

EXAMPLE 120

Sulfamic acid 3,5-difluorophenyl ester

Using the procedure of Example 75, the title compound was prepared using a mixture of 9.9 g (0.076 mole) of 3,5-difluorophenol and 7.0 ml (0.08 mole) of chlorosulfonyl isocyanate in 50 ml of toluene. The solid product was recrystallized from benzene to yield 11.7 g (74%) of white solid, mp 85°–88° C.

Analysis: Calculated for $C_6H_5F_2NO_3S$: C, 34.45; H, 2.41; N, 6.70. Found: C, 34.53; H, 2.34; N, 6.79.

EXAMPLE 121

Sulfamic acid 4-fluorophenyl ester

Using the procedure of Example 75, a mixture of 11.2 g (0.1 mole) of 4-flurophenol and 9.1 ml (0.105 mole) of chlorosulfonyl isocyanate in 50 ml of toluene gave, after recrystallization from benzene, 15.0 g (79%) of the title compound as a white solid, mp 82.5°–85.5° C.

Analysis: Calculated for $C_6H_6FNO_3S$: C, 37.70; H, 3.16; N, 7.33. Found: C, 37.83; H, 3.11; N, 7.37.

EXAMPLE 122

Sulfamic acid 2-[3(1H-imidazol-1-yl)phenoxy]ethyl ester

A solution of sulfamoyl chloride (0.0275 mole) in 60 ml of acetonitrile was treated dropwise with a solution of 5.1 g (0.025 mole) of 2-[3(1H-imidazol-1-yl)phenoxy]ethanol in 100 ml of acetonitrile. The mixture was stirred at ambient temperature under nitrogen for 20 hr. The mixture was concentrated under vacuum, and the residue was partitioned between ethyl acetate and dilute potassium carbonate solution. The organic fraction was again concentrated under vacuum to a crystalline residue. This residue was dissolved in warm 95% ethanol and treated with 1 equivalent of anhydrous hydrogen chloride. The solution was chilled and the precipitate was collected and dried to give 4.0 g (50%) of the title compound as a pinkish powder, monohydrochloride, mp 149.0°–150.0° C.

Analysis: Calculated for $C_{11}H_{13}N_3O_4S·HCl$: C, 41.32; H, 4.41; N, 13.14. Found: C, 41.25; H, 4.50; N, 12.92.

EXAMPLE 123

Sulfamic acid 3-(2-methoxyphenoxy)propyl ester

A solution of 13.0 g (0.071 mole) of 3-(2-methoxyphenoxy)-1-propanol (prepared in 68% yield from guaiacol (43.2 g, 0.35 mole), 3-bromo-1-propanol (89.3 g, 0.61 mole) and potassium carbonate (112.0 g, 0.81 mole) in 1 l of acetone and 9.0 g (0.089 mole) of triethylamine in 50 ml of methylene chloride was added dropwise (20 min.) to a stirred, cooled (ice-acetone bath) solution of 22 ml (0.0786 mole) of sulfamoyl chloride (3.57M solution in acetonitrile, Preparation 19) in 30 ml methylene chloride at such a rate the temperature was maintained at $\leq 12°$ C. The reaction mixture was stirred at ambient temperature for 3 hr. The solvents were evaporated under reduced pressure and the viscous residue was triturated with 300 ml of ethyl acetate and the solids removed by filtration. The filtrate was washed with three 300 ml portions of water, dried (magnesium sulfate) and the solvent evaporated under reduced pressure to yield 11.7 g (63%) of a colorless, viscous oil that solidified upon standing. The solid was recrystallized from methylene chloride-petroleum ether (30°–60° C.) to give 6.9 g (37%) of the title compound as a white solid, mp 80°–83° C.

Analysis: Calculated for $C_{10}H_{15}NO_5S$: C, 45.97; H, 5.79; N, 5.36. Found: C, 45.85; H, 5.85; N, 5.28.

EXAMPLE 124

Methylsulfamic acid 2-methoxyphenyl ester

A solution of 12.4 g (0.1 mole) of 2-methoxyphenol (guaiacol; Aldrich) and 13.1 g (0.1 mole) of methylsulfamoyl chloride (Preparation 22) in 150 ml of toluene was stirred and treated at reflux for 2 hr. The solvent was evaporated under reduced pressure and the only residue was purified by high pressure liquid chromatography (Waters Associates Prep LC/System 500A, Prep-PAK® 500A silica, ethyl acetate-hexanes, 1:2; flow rate 150 ml/min). Fractions containing the product were combined and the solvents evaporated under reduced pressure to yield an oil that solidified upon standing. The solid was recrystallized from benzene-petroleum-ether (30°–60° C.) to give 14.3 g (66%) of the title compound as a white solid, mp 68°–71° C.

Analysis: Calculated for $C_8H_{11}NO_4S$: C, 44.23; H, 5.10; N, 6.45. Found: C, 44.09; H, 5.12; N, 6.41.

EXAMPLE 125

Sulfamic acid 1,1-dimethyl-2-phenoxy ethyl ester

To a chilled (ice-water bath) solution of 30 ml (0.11 mole) of 3.57M sulfamoyl chloride solution (Preparation 20) in 50 ml of acetonitrile was added dropwise a solution of 0.10 mole of 1,1-dimethyl-2-phenoxyethanol and 0.229 mole of triethylamine in 20 ml of acetonitrile at such a rate as to maintain a temperature less than 15° C. The mixture was then stirred for 3 hr at ambient temperature, filtered, and concentrated to an oil that was purified by preparative high pressure liquid chromatography.

EXAMPLE 126

Sulfamic acid 2-[4-[(1H-imidazol-1-yl)phenoxy]ethyl ester

A stirred mixture of 8.0 g (0.050 mole) of 4(1H-imidazol-1-yl)phenol, 13.5 ml (0.20 mole) of 2-chloroethanol and 28 g (0.2 mole) of potassium carbonate in 200 ml of methyl ethyl ketone was heated at reflux, filtered, and concentrated to obtain 5.1 g of 2-[4-(1H-imidazol-1-yl)phenoxy]ethanol (50%). This alcohol (0.25 mole) and 5.2 g (0.030 mole) of sulfamic acid phenyl ester (Example 33) in 100 ml of dioxane was heated at reflux for 20 minutes, concentrated and the residual solid triturated in acetone. The triturant was acidified with an anhydrous solution of hydrogen chloride in isopropyl alcohol and the solid hydrochloride collected by filtration. The product was recrystallized from isopropyl alcohol-isopropyl ether to yield 4.26 g of solid, monohydrochloride, mp 156°–157° C.

Analysis: Calculated for $C_{11}H_{13}N_3O_4S·HCl$: C, 41.32; H, 4.41; N, 13.14. Found: C, 41.60; H, 4.62; N, 12.87.

EXAMPLE 127

Sulfamic acid 3-[4-(1H-imidazol-1-yl)phenoxy]propyl ester

A solution of 9.0 g (0.041 mole) of 3-[4-(1H-imidazol-1-yl)phenoxy]propanol in 150 ml of acetonitrile was treated with a solution of one equivalent of sulfamoyl chloride in 13 ml of acetonitrile. The mixture was stirred for 20 hr. The reaction mixture was concentrated under vacuum and the residue was dissolved in water. The aqueous solution was filtered and the filtrate was basified to pH 8 with potassium carbonate. The mixture was extracted with ethyl acetate. The organic fraction was concentrated under a stream of nitrogen and the precipitate was collected and dried to give 5.2 g (43%) of tan powder, mp 105.0°–106.0° C.

Analysis: Calculated for $C_{12}H_{15}N_3O_4S$: C, 48.48; H, 5.09; N, 14.13. Found: C, 48.73; H, 5.12; N, 13.95.

EXAMPLE 128

Sulfamic acid 2-[3-(2-methyl-1H-imidazol-1-yl)phenoxy]ethyl ester

A mixture of 17.4 g (0.10 mole) of 3-(2-methyl-1H-imidazol-1-yl)phenol, 40.2 g (0.50 mole) of chloroethanol and 70 g (0.5 mole) of potassium carbonate in 100 ml of methyl ethyl ketone was heated at reflux for 30 hr. The reaction mixture was filtered and the filtrate was concentrated. The residue was partitioned between ethyl acetate and dilute potassium carbonate solution. The organic layer was concentrated and chromatographed on silica gel to give 7 g of desired product of approximately 90% purity. This intermediate was sulfamoylated by treatment in 150 ml of acetonitrile with 1.3 equivalents of sulfamoyl chloride in 13 ml of acetonitrile and 1 g of diisopropylethyl amine. When HPLC indicated all starting material was consumed, the reaction mixture was quenched with water, then concentrated to a syrup. The syrup was partitioned between ethyl acetate and dilute potassium carbonate solution. The organic layer was concentrated and chromatographed on silica gel. The fractions containing desired product were combined and concentrated. The syrup (3.0 g) was dissolved in 40 ml of 2-propanol and treated with 1 equivalent of anhydrous hydrogen chloride. The precipitate was collected and dried to give 2.8 g (9.4%) of an off-white powder. This material was recrystallized from 95% ethanol to give 1.9 g of tan-yellow, monohydrochloride crystals, mp 184°-186° C.

Analysis: Calculated for $C_{12}H_{15}N_3O_4S \cdot HCl$: C, 43.18; H, 4.83; N, 12.59. Found: C, 43.36; H, 4.90; N, 12.41.

EXAMPLE 129

Sulfamic acid 2-[4-(1H-1,2,4-triazol-1-yl)phenoxy]ethyl ester

A solution of 8.2 g (0.04 mole) of 2-[4-(1H-1,2,4-triazol-1-yl)phenoxy]ethanol in 100 ml of acetonitrile was treated with a solution of 1.3 equivalents of sulfamoyl chloride in 19 ml of acetonitrile. One equivalent, 5.2 g (0.04 mole) of diisopropylethylamine was also added in one portion. The mixture was stirred for 2 hr. The precipitate was collected and partitioned between ethyl acetate and a dilute potassium carbonate solution. The organic layer was separated and concentrated to a white powder. The powder was triturated with ethyl ether, collected and dried to give 6.3 g (55%) of white powder, mp 134°-136° C.

Analysis: Calculated for $C_{10}H_{12}N_4O_4S$: C, 42.25; H, 4.26; N, 19.71. Found: C, 42.39; H, 4.31; N, 19.41.

EXAMPLE 130

Sulfamic acid 2-[3-(4-methyl-1H-imidazol-1-yl)phenoxy]ethyl ester

By the same procedure Example 111, 2-[3-(4-methyl-1H-imidazol-1-yl)phenoxy]ethanol monohydrochloride was first converted to its free base and then to the monohydrochloride in 51% overall yield, mp 169°-170° C.

Analysis: Calculated for $C_{12}H_{0.5}N_3O_4S \cdot HCl$: C, 43.18; H, 4.83; N, 12.59. Found: C, 42.74; H, 4.87; N, 12.38.

EXAMPLE 131

Sulfamic acid 3-(2-methyl-1H-imidazol-1-yl)phenyl ester

A slurry of 8.7 g (0.05 mole) of 3-(2-methyl-1H-imidazol-1-yl)phenol in 150 ml of acetonitrile was treated with a solution of 0.05 mole of sulfamoyl chloride in 20 ml of acetonitrile. The mixture dissolved and slowly deposited off-white crystals over the period of 24 hr. The precipitate was collected and triturated with hot absolute ethanol. The slurry was cooled and the precipitate was collected and dried to give 4.0 g (32%) of off-white powder, monohydrochloride, mp 197°-200° C.

Analysis: Calculated for $C_{10}H_{11}N_3O_3S \cdot HCl$: C, 41.46; H, 4.18; N, 14.50. Found: C, 41.28; H, 4.22; N, 14.57.

EXAMPLE 132

Sulfamic acid 2-[3-(diethylamino)phenoxy]ethyl ester 2-(3-Nitrophenoxy)ethanol (13.7 g, 0.075 mole), acetaldehyde (30 ml, 0.52 mole), and 5% Pd-C (1.5 g) in 100 ml methanol and 20 ml ethanol was hydrogenated on a Parr hydrogenator for 3.5 hr whereupon the pressure drop had ceased. The mixture was filtered, and the filtrate concentrated to an oil (18.4 g). This oil was chromatographed on 350 g silica gel eluted with 5% MeOH/CH$_2$Cl$_2$ to give 8.45 g of an almost colorless oil. $^1$H NMR supported the structure of 2-(m-diethylaminophenoxy)ethanol of which 7.45 g (0.036 mole) was converted to the title compound by reacting with the sulfamoyl chloride generated by mixing chlorosulfonylisocyanate (0.09 mole) and formic acid (0.09 mole) in acetonitrile as described in Preparation 19. The product free base was isolated by acid-base transfer extractions. The oily free base solidified upon cooling. It was recrystallized twice from toluene and dried under vacuum overnight at room temperature, mp 105°-6° C.

Analysis: Calculated for $C_{12}H_{20}N_2O_4S$: C, 49.98; H, 6.99; N, 9.71. Found: C, 49.86; H, 7.09; N, 9.72.

EXAMPLE 133

Sulfamic acid 3-(2-hydroxyethyl)-2-(3-phenoxyphenyl)-4-thiazolidinone ester a. 3-(2-hydroxyethyl)-2-(3-phenoxyphenyl)-4-thiazolidinone A mixture of 15.3 g (0.077 mole) of 3-phenoxybenzaldehyde (Fluka), 4.8 g (0.078 mole) of ethanolamine (99%, Aldrich) and 7.5 g (0.077 mole) of mercaptoacetic acid (95%, Aldrich) in 150 ml of benzene was stirred and heated at reflux temperature overnight utilizing a Dean-Stark trap to remove water. The reaction mixture was poured into a solution of 300 ml of water and 20 ml of concentrated ammonium hydroxide solution. The layers were separated and the organic layer was washed twice with 100 ml portions of 2N hydrochloric acid, twice with 100 ml portions of water, dried (magnesium sulfate) and the solvent evaporated under reduced pressure to give 23.6 g (97%) of the alcohol which was used without further purification.

b. Preparation of the title compound

This compound was prepared by the procedure of Example 28. Thus, 20.0 g (0.063 mole) of 3-(2-hydroxyethyl)-2-(3-phenoxyphenyl)-4-thiazolidinone, 22 ml (247.7 mole) of chlorosulfonylisocyanate (98%, Aldrich), 25.6 g (0.254 mole) of triethylamine, and 4.0 g (0.222 mole) of water in 250 ml of acetonitrile gave 16.0 g of a viscous oil. The oil was purified by chromatography (4.5×90 cm glass column; 500 g of silica gel; methylene chloride, then acetone). Desired fractions were combined and th solvents were evaporated under reduced pressure to give 10.2 g of an oily residue. The oil was triturated with methylene chloride-edthyl ether and the resulting solid was collected by filtration. The solid was recrystallized from methylene chloride-ethyl ether to give 6.1 g (24%) of the title compound as a white solid, mp 108°-111° C.

Analysis: Calculated for $C_{17}H_{18}N_2O_5S_2$: C, 51.76; H, 4.60; N, 7.10; Found: C, 51.90; H, 4.66; N, 7.04.

EXAMPLE 134

Sulfamic acid 2-(methoxycarbonyl)propyl ester

A mixture of 5.9 g (0.05 mole) of (S)-(+)methyl 3-hydroxy-2-methyl]propionate, 9.5 g (0.055 mole) of phenyl sulfamate, 25 ml of toluene and 0.5 g of pyridine was heated at reflux for 2 hr. The reaction solution was concentrated under vacuum, and the residue was chromatographed, using silica gel and eluting with 2% methanol in methylene chloride. The desired fractions were concentrated under vacuum to give 3.9 g (40%) of a pale yellow oil.

Analysis: Calculated for $C_5H_{11}NO_5S$: C, 30.45; H, 5.62; N, 7.10. Found: C, 30.23; H, 5.84; N, 6.95.

EXAMPLE 135

Sulfamic acid (4-chlorophenoxy)-1,3-propanediyl ester

To a cooled (ice bath) solution of 7.8 ml (12.7 g, 0.09 mole) of chlorosulfonyl isocyanate in 50 ml of acetonitrile was added portionwise a solution of 3.9 g (0.09 mole; a factor of 0.935 was used to compensate for 4% $H_2O$ present) of 96% formic acid in 20 ml acetonitrile at such a rate that the temperature did not exceed 12° C. After the addition was complete, the solution was stirred at ambient temperature for 3 hr, cooled to 10° C., and treated dropwise with a solution of 8.1 g (0.04 mole) of 2-(4-chlorophenoxy)-1,3-propanediol and 13.9 ml (10.3 g, 0.08 mole) of diisopropylethylamine in 75 ml of acetonitrile at such a rate that the temperature did not exceed 15° C. The solution was stirred at ambient temperature overnight and then concentrated. The residue was dissolved in 200 ml of methylene chloride and 50 ml of ethyl acetate, and washed successively with 50 ml portions of water, 2N hydrochloric acid solution (twice), water and dilute sodium bicarbonate, dried (sodium sulfate), and concentrated to give a gum as residue. The gum was purified by column chromatography on 320 g of silica gel using a gradient elution of 0–35% acetone in benzene. The appropriate fractions were combined and concentrated to give a solid. The solid was recrystallized from benzene-acetonitrile to yield 6.7 g (47%) of white solid, mp 133°–134° C.

Analysis: Calculated for $C_9H_{13}Cl_N2O_7S_2$: C, 29.96; H, 3.63; N, 7.76. Found: C. 30.00; H, 3.67; N, 7.76.

EXAMPLE 136

Methylsulfamic acid 2-(4-chlorophenoxy)-1,3-propanediyl ester

To a solution of 11.7 g (0.09 mole) of freshly distilled methylsulfamoyl chloride in 50 ml of methylene chloride was added dropwise a solution of 8.1 g (0.04 mole) of 2-(4-chlorophenoxy)-1,3-propanediol and 15.6 ml (11.6 g, 0.09 mole) of diisopropylethylamine in 100 ml of methylene chloride. The solution was stirred at ambient temperature for 24 hr and then washed successively wiht 50 ml portions of water, 2N hydrochloric acid solution (twice), water, dilute aqueous sodium bicarbonate and brine, dried (sodium sulfate), and concentrated to give a gum as residue. The gum was purified by column chromatography on 360 g of silica gel using a gradient elution with 0–20% acetone in benzene. The appropriate fractions were combined and concentrated to yield 13.8 g (88%) of the title compound as a clear gum.

Analysis: Calculated for $C_{11}H_{17}ClN_2O_7S_2$: C, 33.98; H, 4.41; N, 7.20. Found: C, 33.51; H, 4.40; N, 7.31.

EXAMPLE 137

Dimethylsulfamic acid 2-[4-(1H-imidazol-1-yl)phenoxy]ethyl ester

To a solution of 15.0 g (0.074 mol) of 2-[4-(1H-imidazol-1-yl)phenoxy]ethanol in 100 mL of N,N-dimethylformamide (DMF) was added 3.8 g (0.1 mol) of sodium hydride (60% oil dispersion) portionwise and the mixture was stirred at ambient temperature for 3 h. To this mixture was added 13.7 g (0.1 mol) of dimethylsulfamoyl chloride and the mixture was stirred at ambient temperature overnight. The reaction mixture was poured into 1.2 L of water and its pH was adjusted to 10 with sodium carbonate. The mixture was extracted with three 400-mL portions of ethyl acetate. The combined organic layers were washed twice with 400-mL portions of water, dried ($MgSO_4$), and the solvent was evaporated under reduced pressure to give a viscous residue. The residue was purified by high pressure liquid chromatography (Waters Associates Prep LC/System 500 A; PrepPAK 500 silica; ethyl acetate; flow rate 150 mL/min). Fractions containing the product were combined and the solvent was evaporated under reduced pressure to give the title compound, a viscous oil. The oil was converted to the hydrochloride (2-propanol; ethereal HCl) and the white solid was collected by filtration to yield 5.9 g (26%), mp 120°–123° C.

Analysis: Calc. for $C_{13}H_{17}N_3O_4S.HCl.H_2O$: C, 42.68; H, 5.51; N, 11.49. Found: C, 42.84; H, 5.41; N, 11.49.

INTRAOCULAR PRESSURE

The intraocular pressure (IOP) of normotensive, male, New Zealand rabbits is measured by standard procedures (Maren, T. H. et al., J. Pharmacol. Exp. Ther. 241, 56 (1987)). The rabbits are acclimated to handling and to use of the IOP measuring device (Digilab Modular One Tonometer, Biorad, Cambridge, Mass.) prior to the testing of drugs. To measure the IOP, unanesthetized, unrestrained rabbits are placed on the counter top and one drop of local anesthetic (Ophthetic, 0.5%, Allergan, Irvine Calif.) placed onto each eye just prior to testing. The pressure sensing stylus of the Digilab Modular One tonometer is applanted on the cornea of the eye and the IOP is digitally recorded. Usually, 2–4 readings are made at each time point, and the average IOP recorded. Readings of the IOP are made at various times prior to and after drug application. For topical studies, the drug (50 microliters of 0.5–5% wt/vol solution or suspension in aqueous 0.5% hydroxyethyl cellulose solution) is applied to one eye and vehicle to the contralateral eye. In these studies (topical), the difference in IOP between the treated and control eye is determined. Changes in IOP or differences in IOP between the treated and untreated eyes are determined. For oral administration studies, the drug is dissolved or suspended in 0.5% Tween 80 aqueous solution and the rabbits are dosed at 10 ml/kg.

Table II shows the effect of representative compounds of Formula I on IOP as determined in the above procedure.

TABLE II

| Change in Intraocular Pressure | | | |
|---|---|---|---|
| Example | Applied As[1] | pH | Time (hr) | IOP change (mmHg) |
| 126 | solution | 4.6 | 1 | −2.6 |
|  |  |  | 2 | −2.2 |
|  |  |  | 4 | −1.5 |
| 73 | oral* |  — | 2 | −4.45 |
|  | solution | 4.4 | 1 | −0.3 |
|  |  |  | 2 | −1.0 |
|  |  |  | 3 | −1.3 |
| 102 | solution | 4.1 | 2 | −1.5 |
|  |  | 5.2 | 2 | −0.8 |
| 3 | suspension | 7.4 | 1 | −1.2 |
| 12 | suspension | 7.4 | 1 | −1.0 |
|  | suspension | 7.4 | 1 | −0.8 |

[1]Drug administered topically to eye except as noted (50 μl of 2% solution or suspension).
*Oral dose given at 3.16 mg/kg, change in IOP is average for both eyes compared to IOP prior to drug administration.

PHARMACEUTICAL COMPOSITION

It is particularly advantageous to use topical administration of an agent to reduce intraocular pressure, because the amount administered can be reduced markedly from the amount necessary when administration is oral. Moreover, topical administration minimizes or eliminates potentially adverse side effects which may result when the agent is administered systemically.

Thus, the compounds of the invention will generally be administered as topical ophthalmic formulations such as ointment, suspension, solution or insert. One skilled in the art is familiar with such formulations. A compound of formula I will typically be present in an amount of about 0.01 to 15 percent by weight based on the total weight of the formulations. Most preferable, about 0.1 to 3 percent of a compound of Formula I will be present in the formulations. The objective is to administer a dose of from 0.1 to 10 mg per eye per day to the patient, with treatment continuing so long as the condition being treated persists. It is only necessary that the active ingredient constitute an effective amount such that a suitable effective dosage will be obtained consistent with the dosage form employed. The exact individual dosages, as well as daily dosages, will, of course, be determined according to standard medical principles under the direction of a physician or veterinarian.

An ophthalmic solution is a preferred ophthalmic formulation. In such a presentation, a compound of Formula I is dissolved in a physiologically acceptable, isotonic solution such as an isotonic boric acid solution, an isotonic sodium chloride solution, an isotonic sodium borate solution or the like.

The ophthalmic solution may further comprise a non-ionic surfactant to aid in dissolving the compound of Formula I, suitable surfactants being polyoxyethylene sorbitan monooleate, polyoxyethylene stearoyl triglyceride, polyethylene glycol, alpha- or beta-cyclodextrin, and the like.

The ophthalmic solution may further comprise a preservative such as p-hydroxybenzoate ester such as methyl or ethyl p-hydroxybenzoate, a cationic surfactant such as benzalkonium chloride, or an alcohol such as benzyl alcohol, chlorbutanol or phenethyl alcohol.

Ointments containing a compound of Formula I may be prepared in the conventional way using known excipients such as polyethylene glycol, a cellulose derivative, petroleum jelly, fluid paraffin, polyoxyethylene sorbitan monooleate, polyoxyethylene stearoyl triglyceride or the like. A preservative such as one of those described above may also be included.

The ophthalmic solution and ointment will typically have a Ph of about 4 to 8. Beyond these extremes the ophthalmic formulation is not generally physiologically acceptable.

Various modifications and equivalents will be apparent to one skilled in the art and may be made in the compounds, method, and compositions of the present invention without departing from the spirit or scope thereof, and it is therefore to be understood that the invention is to be limited only the scope of the appended claims.

What is claimed is:

1. A method for reducing intraocular pressure in a mammal, comprising administering to said mammal an effective amount of a compound having the formula:

$$(HO)_p\text{—}A\text{—}[\text{—}OS(O)_2NR^1R^2]_z$$

wherein

A is aryloxy-alkyl, in which the aryl moiety is a substituted phenyl group of the formula:

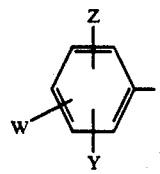

where

X is hydrogen, halo, $CF_3$, nitro-, $-SO_2NR_1R_2$, loweralkoxy, hydroxy, amino, loweralkylamino, diloweralkylamino, methylcarbonylamino, loweralkyl, methyloxycarbonyl, 1H-imidazol-1-yl, 3-thiazole, 1-pyrrole, phenyl, 1H-triazol-1-yl, cyano, 2-loweralkyl-1H-imidazol-1-yl, 4-loweralkyl-1H-imidazol-1-yl, 4-phenyl-1H-imidazol-1-yl, —COOH, —COOM wherein M is a pharmaceutically acceptable metal cation, aryloxy or aroyl;

Y is hydrogen, halo, loweralkoxy, hydroxy or loweralkyl; and

W is hydrogen, loweralkoxy or loweralkyl;

and said alkyl portion of A being substituted on one or more carbon atoms by the depicted sulfamyloxy group, where Z is the number of $-OS(O)_2NR^1R^2$ groups present on the alkyl moiety of A and is always at least one;

p is the number of hydroxyl groups present on the alkyl moiety of A which have not been converted to $-OS(O)_2NR^1R^2$ groups, including zero;

$R^1$ is hydrogen or loweralkyl;

$R^2$ is hydrogen, loweralkyl, $-CO_2R^1$, or $-CO_2-M+$ wherein M is defined above;

and the pharmaceutically acceptable salts thereof when they can be formed and the optical isomers thereof, when they can be formed.

2. A method of claim 1 in which the compound having the formula:

$$(HO)_p\text{—}A\text{—}[OS(O)_2NH_2]_z$$

is water soluble and is administered topically to the eye of said mammal; and

X is amino, loweralkylamino, diloweralkylamino, 1H-imidazol-1-yl, 2-loweralkyl-1H-imidazol-1-yl, 4-loweralkyl-1H-imidazol-1-yl, 1H-triazol-1-yl, COOH or COOM wherein M is a pharmaceutically acceptable cation;

Y is hydrogen, halo, loweralkoxy, hydroxy or loweralkyl;

W is hydrogen, loweralkoxy, or loweralkyl;

and the pharmaceutically acceptable salts thereof when they can be formed and the optical isomers thereof when they can be formed.

3. The method of claim 1 wherein the compound used is sulfamic acid 1-[(2-methoxyphenoxy)methyl]-1,2-ethanediyl ester.

4. The method of claim 1 wherein the compound used is sulfamic acid 2-phenoxy-1,3-propanediyl ester.

5. The method of claim 1 wherein the compound used is sulfamic acid 2-(4-chlorophenoxy)ethyl ester.

6. The method of claim 1 wherein the compound used is methylsulfamic acid 2-(4-chlorophenoxy)ethyl ester.

7. The method of claim 1 wherein the compound used is methylsulfamic acid-3-phenoxy-1,2-propanediyl ester.

8. The method of claim 1 wherein the compound used is methylsulfamic acid 2-[4-(1H-imidazol-1-yl)phenoxy]ethyl ester, or a pharmaceutically acceptable salt thereof.

9. The method of claim 1 wherein the compound used is methylsulfamic acid 2-phenoxy-1,3-propanediyl ester.

10. The method of claim 1 wherein the compound used is sulfamic acid 2-[3-(1H-imidazol-1-yl)phenoxy]ethyl ester, or a pharmaceutically acceptable salt thereof.

11. The method of claim 1 wherein the compound used is sulfamic acid 2-[3-(2-methyl-1H-imidazol-1-yl)phenoxy]ethyl ester, or a pharmaceutically acceptable salt thereof.

12. The method of claim 1 wherein the compound used is sulfamic acid 2-[3-(diethylamino)phenoxy]ethyl ester, or a pharmaceutically acceptable salt thereof.

13. The method of claim 1 wherein the compound used is sulfamic acid 2-(4-chlorophenoxy)-1,3-propanediyl ester.

14. The method of claim 1 wherein the compound used is methylsulfamic acid 2-(4-chlorophenoxy)-1,3-propanediyl ester.

15. The method of claim 1 wherein the compound used is sulfamic acid 2-[4-(1H-imidazol-1-yl)phenoxy]ethyl ester, or a pharmaceutically acceptable salt thereof.

16. The method of claim 1 wherein the compound used is dimethyl sulfamic acid 2-[4-(1H-imidazol-1-yl)phenoxy]ethyl ester, or a pharmaceutically acceptable salt thereof.

17. A pharmaceutical composition for lowering intraocular pressure in a mammal comprising an effective amount of a compound of the formula:

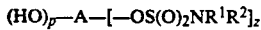

wherein
A is aryloxy-alkyl, in which the aryl moiety is a substituted phenyl group of the formula:

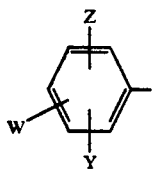

where
X is hydrogen, halo, $CF_3$, nitro-, $-SO_2NR_1R_2$, loweralkoxy, hydroxy, amino, loweralkylamino, diloweralkylamino, methylcarbonylamino, loweralkyl, methyloxycarbonyl, 1H-imidazol-1-yl, 3-thiazole, 1-pyrrole, phenyl, 1H-triazol-1-yl, cyano, 2-loweralkyl-1H-imidazol-1-yl, 4-loweralkyl-1H-imidazol-1-yl, 4-phenyl-1H-imidazol-1-yl, —COOH, —COOM wherein M is a pharmaceutically acceptable metal cation, aryloxy or aroyl;

Y is hydrogen, halo, loweralkoxy, hydroxy or loweralkyl; and

W is hydrogen, loweralkoxy or loweralkyl; and said alkyl portion of A being substituted on one or more carbon atoms by the depicted sulfamyloxy group, where Z is the number of $-OS(O)_2NR^1R^2$ groups present on the alkyl moiety of A and is always at least one;

p is the number of hydroxyl groups present of the alkyl moiety of A which have not been converted to $-OS(O)_2NR^1R^2$ groups, including zero;

$R^1$ is hydrogen or loweralkyl;

$R^2$ is hydrogen, loweralkyl, $-CO_2R^1$, or $-CO_2M+-$ wherein M is defined above;

and the pharmaceutically acceptable salts thereof when they can be formed and the optical isomers thereof, when they can be formed, and a pharmaceutically acceptable carrier.

18. A pharmaceutical composition for topical administration to the eye of a mammal in need thereof comprising an effective amount of a water soluble compound having the formula:

$$(HO)_p-[OSO_2NH_2]_2$$

wherein:
A is aryloxy-alkyl in which the aryl moiety is a substituted phenyl group of the formula:

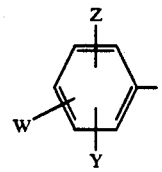

wherein
X is amino, loweralkylamino, diloweralkylamino, 1H-imidazol-1-yl, 4-loweralkyl-1H-imidazol-1-yl, 1H-triazol-1-yl, —COOH or —COOM wherein M is a pharmaceutically acceptable cation;

Y is hydrogen, halo, loweralkoxy, hydroxy or loweralkyl;

W is hydrogen, loweralkoxy or loweralkyl; and said alkyl portion of A being substituted on one or more carbon atoms by the depicted sulfamoyloxy group, where Z is the number of $-OS(O)_2NH_2$ groups present and is always at least one;

p is the number of hydroxygroups present on the alkyl moiety of A which have not been converted to $-OS(O)_2NH_2$ groups, including zero;

or a pharmaceutically acceptable salt thereof when they can be formed; the optical isomers thereof when they can be formed; and a pharmaceutically acceptable carrier.

19. A pharmaceutical composition comprised of a pharmaceutically acceptable carrier and a therapeutically effective amount of a compound which is a pharmaceutically acceptable salt of sulfamic acid 2-[4(1H-imidazol-1-yl)phenoxy]ethyl ester.

20. A pharmaceutical composition comprised of a pharmaceutically acceptable carrier and a therapeutically effective amount of methylsulfamic acid 1-[(2-methoxyphenoxy)-methyl]-1,2-ethanediyl ester.

* * * * *